(12) United States Patent
Brink et al.

(10) Patent No.: US 9,232,703 B2
(45) Date of Patent: Jan. 12, 2016

(54) PLANT GENOMIC DNA FLANKING SPT EVENT AND METHODS FOR IDENTIFYING SPT EVENT

(75) Inventors: Kent Brink, Newark, DE (US); Erin Crowgey, Wilmington, DE (US); Nina Dietrich, Middletown, DE (US); David Hondred, Altoona, IA (US); Joshua K Young, Johnston, IA (US); Cathy Xiaoyan Zhong, Wilmington, DE (US)

(73) Assignees: PIONEER HI BRED INTERNATIONAL INC, Johnston, IA (US); E I DU PONT DE NEMOURS AND COMPANY, Wilmington, DE (US)

( * ) Notice: Subject to any disclaimer, the term of this patent is extended or adjusted under 35 U.S.C. 154(b) by 405 days.

(21) Appl. No.: 13/567,743

(22) Filed: Aug. 6, 2012

(65) Prior Publication Data
US 2013/0031674 A1    Jan. 31, 2013

Related U.S. Application Data

(63) Continuation of application No. 12/371,800, filed on Feb. 16, 2009, now Pat. No. 8,257,930.

(60) Provisional application No. 61/028,680, filed on Feb. 14, 2008, provisional application No. 61/110,018, filed on Oct. 31, 2008, provisional application No. 61/111,892, filed on Nov. 6, 2008.

(51) Int. Cl.
*A01H 1/04* (2006.01)
*A01H 5/10* (2006.01)
*A01H 5/00* (2006.01)
*C12N 15/82* (2006.01)

(52) U.S. Cl.
CPC .............. *A01H 5/00* (2013.01); *C12N 15/8245* (2013.01); *C12N 15/8289* (2013.01)

(58) Field of Classification Search
None
See application file for complete search history.

(56) References Cited

U.S. PATENT DOCUMENTS

| 5,981,840 A * | 11/1999 | Zhao et al. ................. 800/294 |
| 2004/0123352 A1 | 6/2004 | Plaisted et al. |
| 2005/0246796 A1 | 11/2005 | Cigan et al. |
| 2006/0070139 A1 | 3/2006 | Bing et al. |
| 2006/0288440 A1 | 12/2006 | Albertsen et al. |
| 2009/0038026 A1 | 2/2009 | Albertsen et al. |

FOREIGN PATENT DOCUMENTS

| WO | 03013224 A2 | 2/2003 |
| WO | 2004099447 A2 | 11/2004 |

OTHER PUBLICATIONS

Unger et al. Transgenic Research 10: 409-422 (2001).*
Yang, L., et al.; "Event Specific Qualitative and Quantitative Polymerase Chain Reaction Detection of Genetically Modified MON863 Maize Based on the 5'-Transgene Integration Sequence"; Journal of Agricultural and Food Chemistry (2005) 53:9312-9318; American Chemical Society; US.
EMBL Accession Number: X66692; *Z. mays* gene for polygalacturonase; Jul. 13, 1992.
EMBL Accession Number: Q94KI9_Maize; *Zea maize* Ms45; Mar. 2001.

* cited by examiner

*Primary Examiner* — David T Fox
(74) *Attorney, Agent, or Firm* — Pioneer Hi-Bred Int'l Inc.

(57) ABSTRACT

Compositions and methods related to transgenic plants comprising seed production technology are provided. Specifically, maize plants having a E6611.32.1.38 event which confers seed production technology are provided. The plant harboring the E6611.32.1.38 event at the recited chromosomal location comprises the genomic/transgene junctions described. The plant genomic DNA flanking the integrated E6611.32.1.38 event can be used to design assays that will be specific for the E6611.32.1.38 event. The characterization of the genomic insertion site of the E6611.32.1.38 event provides for an enhanced breeding efficiency and enables the use of molecular markers to track the transgene insert in the breeding populations and progeny thereof. Various methods and compositions for the identification, detection, and use of the maize E6611.32.1.38 event are provided.

5 Claims, 19 Drawing Sheets

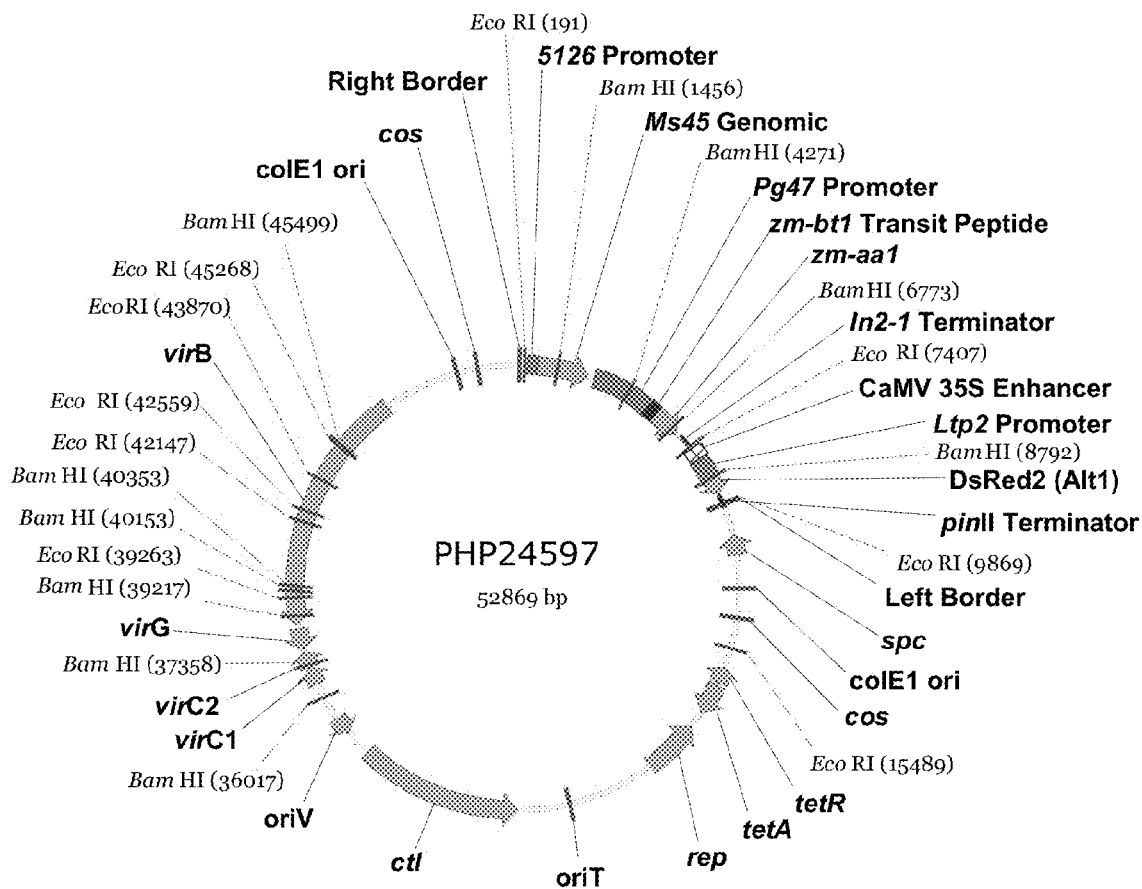
Figure 1: Schematic plasmid map of PHP24597. Plasmid size is 52869 bp.

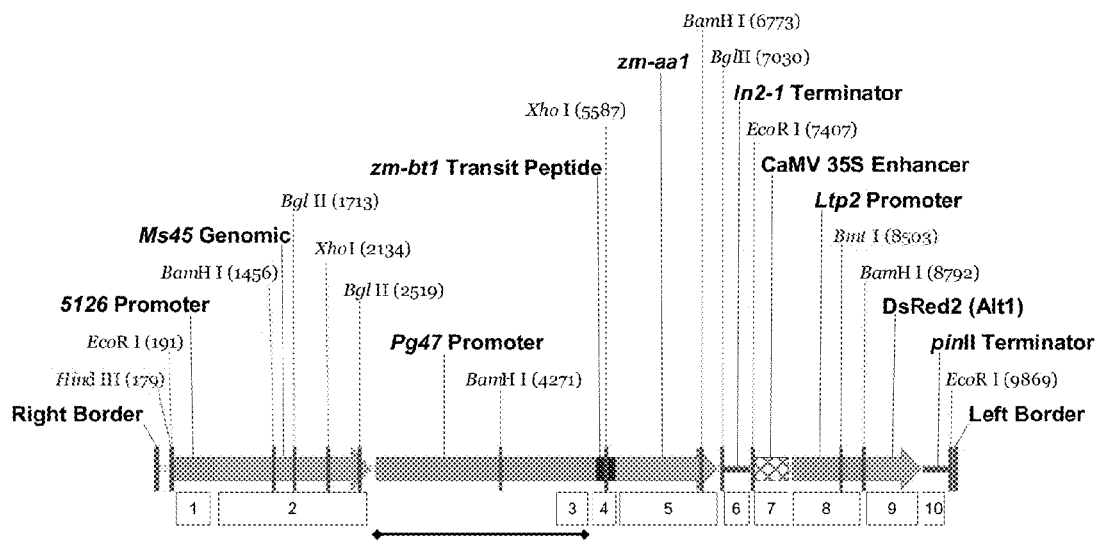
Figure 2:  Map of T-DNA Region from Plasmid PHP24597
Schematic map of T-DNA from PHP24597. T-DNA size is 9950 bp.
The locations of the probes used are shown as boxes in the lower part of the map and are identified below:
| Number | Probe Name |
|---|---|
| 1 | 5126 promoter |
| 2 | Ms45 |
| 3 | Pg47 promoter |
| 4 | zm-bt1 |
| 5 | zm-aa1 |
| 6 | In2-1 terminator |
| 7 | 35S enhancer |
| 8 | Ltp2 promoter |
| 9 | DsRed2 |
| 10 | pinII terminator |

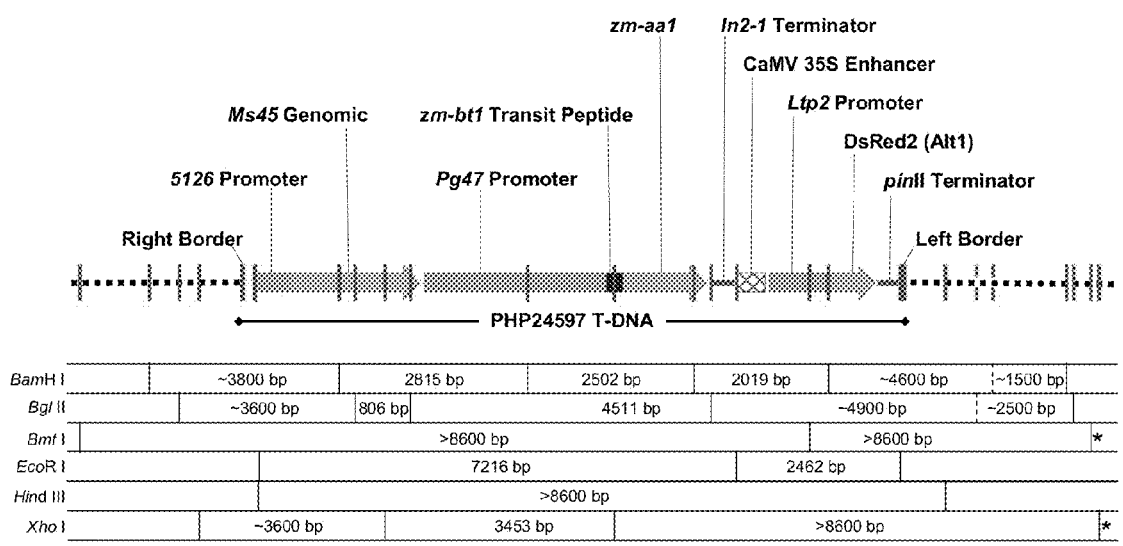
Figure 3: Schematic Map of the Insertion in DP-32138-1 Maize

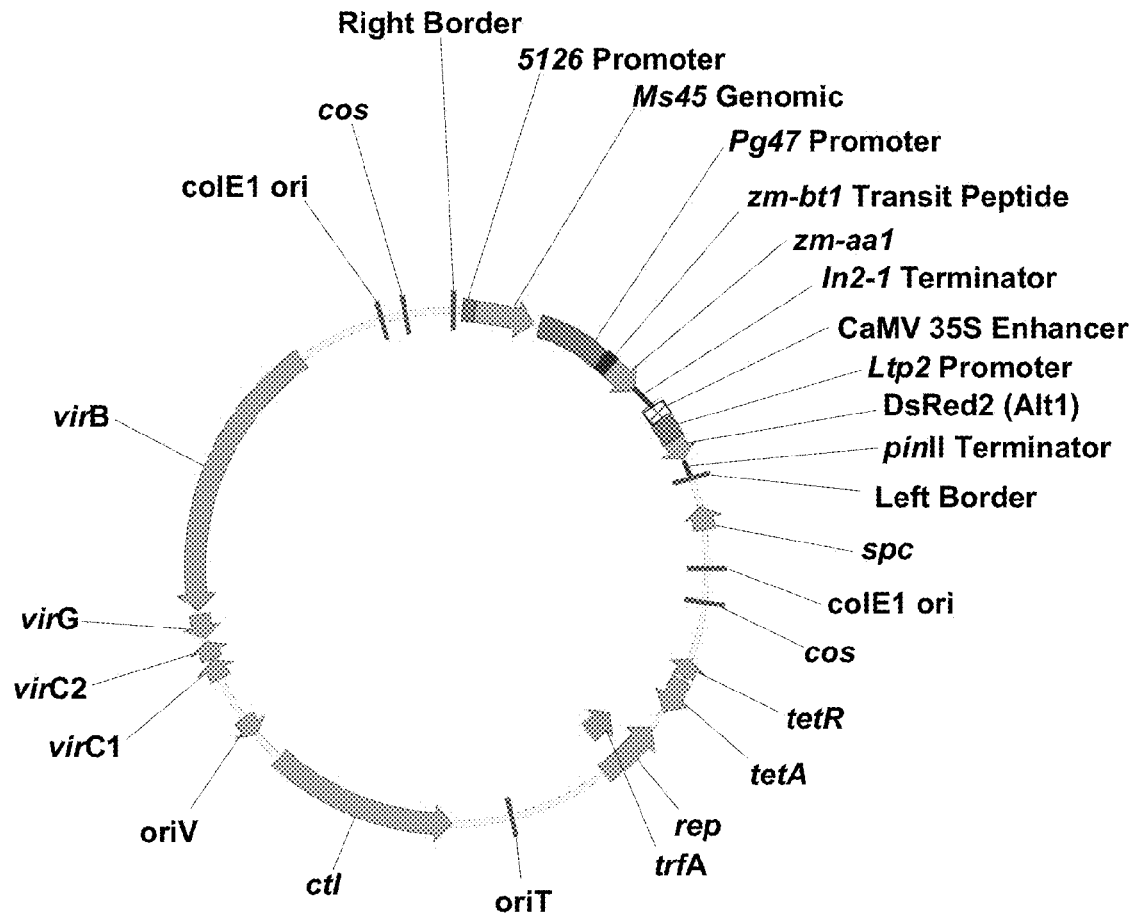
Figure 4: Schematic Diagram of Plasmid PHP24597
Schematic diagram of plasmid PHP24597 with genetic elements indicated. Plasmid size is 52869 bp.

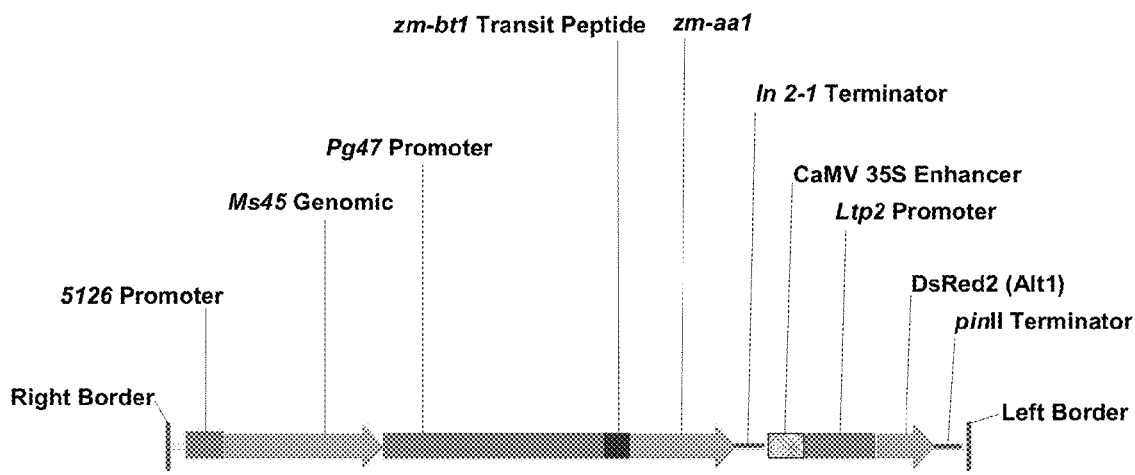
Figure 5: Schematic Diagram of the T-DNA region from Plasmid PHP24597
Schematic diagram of the T-DNA indicating the *Ms45* genomic region, *zm-aa1* gene and the *DsRed2(Alt1)* gene along with their respective regulatory elements. The size of the T-DNA is 9950 bp.

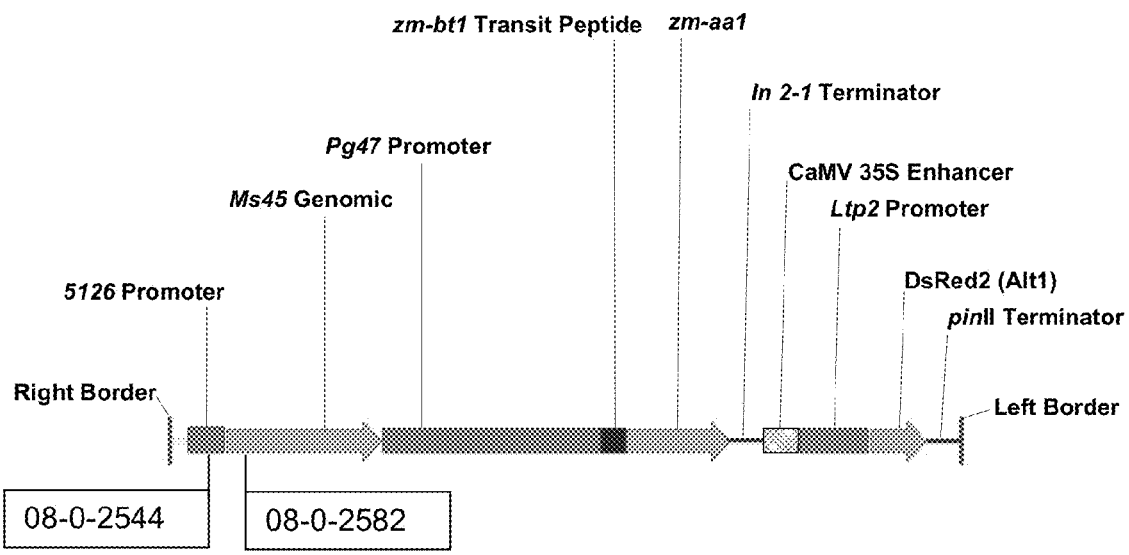
FIGURE 6. MAP OF T-DNA FROM PHP24597
Schematic map of T-DNA from plasmid PHP24597 genetic elements with location of primers (08-0-2544/08-0-2582) used for construct-specific PCR. The figure is not drawn to scale. T-DNA size is 9950 bp.

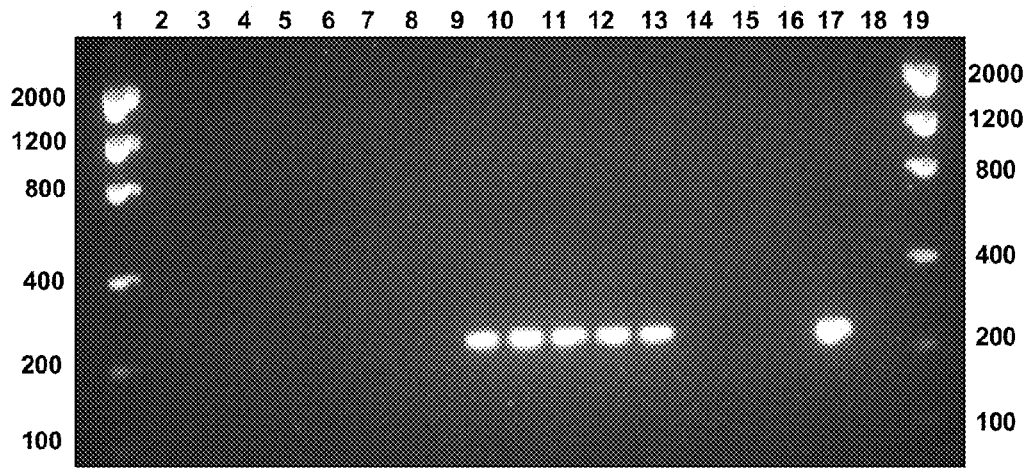

FIGURE 7: PCR AMPLIFICATION WITH PRIMER SET 08-0-2544/08-0-2582 TARGETING THE UNIQUE PROMOTER/GENE JUNCTION OF PHP24597 T-DNA PRESENT IN 32138 MAIZE. EXPECTED AMPLICON SIZE IS 233 BP. SAMPLES WERE LOADED AS FOLLOWS.

Lane Assignments:

| Lane | Sample | Lane | Sample |
| --- | --- | --- | --- |
| 1 | Low DNA Mass Ladder | 11 | 32138 maize plant 3 |
| 2 | Blank | 12 | 32138 maize plant 4 |
| 3 | Control plant 1 | 13 | 32138 maize plant 5 |
| 4 | Control plant 2 | 14 | Blank |
| 5 | Control plant 3 | 15 | No-template control |
| 6 | Control plant 4 | 16 | Blank |
| 7 | Control plant 5 | 17 | PHP24597 |
| 8 | Blank | 18 | Blank |
| 9 | 32138 maize plant 1 | 19 | Low DNA Mass Ladder |
| 10 | 32138 maize plant 2 | | |

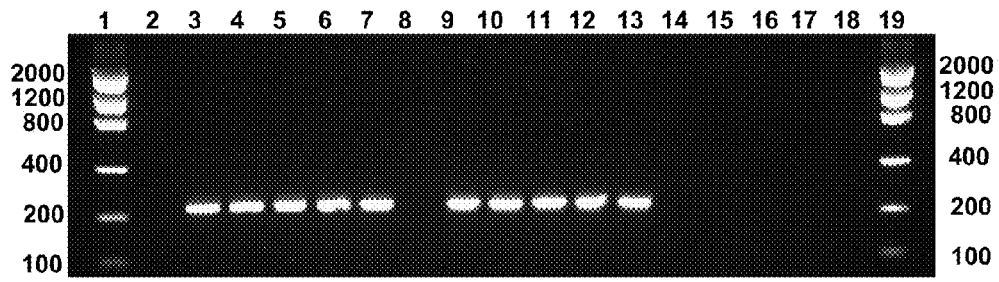

FIGURE 8: MAIZE INVERTASE GENE PCR ANALYSIS OF LEAF DNA FROM 32138 MAIZE AND NON-GENETICALLY MODIFIED CONTROL MAIZE

PCR amplification of endogenous maize invertase gene with primer set 02-O-197/02-O-198 as positive control for PCR amplification. Expected amplicon size is 225 bp. Samples were loaded as follows.

Lane Assignments:

| Lane | Sample | Lane | Sample |
|---|---|---|---|
| 1 | Low DNA Mass Ladder | 11 | 32138 maize plant 3 |
| 2 | Blank | 12 | 32138 maize plant 4 |
| 3 | Control plant 1 | 13 | 32138 maize plant 5 |
| 4 | Control plant 2 | 14 | Blank |
| 5 | Control plant 3 | 15 | No-template control |
| 6 | Control plant 4 | 16 | Blank |
| 7 | Control plant 5 | 17 | PHP24597 |
| 8 | Blank | 18 | Blank |
| 9 | 32138 maize plant 1 | 19 | Low DNA Mass Ladder |
| 10 | 32138 maize plant 2 | | |

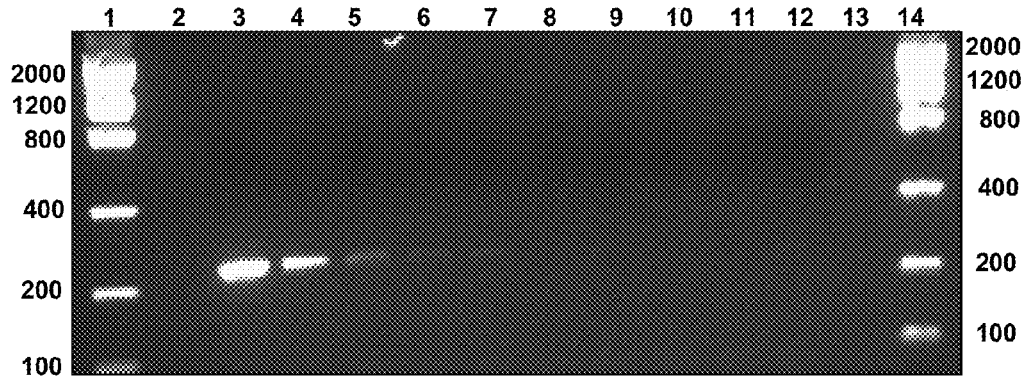
FIGURE 9: SENSITIVITY OF PCR ANALYSIS FOR 32138 MAIZE FOR LEAF DNA SAMPLES
Lane Assignments:
| Lane | Sample | Lane | Sample |
|---|---|---|---|
| 1 | Low DNA Mass Marker | 8 | 10 pg of 32138 maize |
| 2 | Blank | 9 | 5 pg of 32138 maize |
| 3 | 50 ng of 32138 maize | 10 | 500 fg of 32138 maize |
| 4 | 5 ng of 32138 maize | 11 | No-template control |
| 5 | 500 pg of 32138 maize | 12 | 50 ng of Control DNA |
| 6 | 100 pg of 32138 maize | 13 | Blank |
| 7 | 50 pg of 32138 maize | 14 | Low DNA Mass Marker |

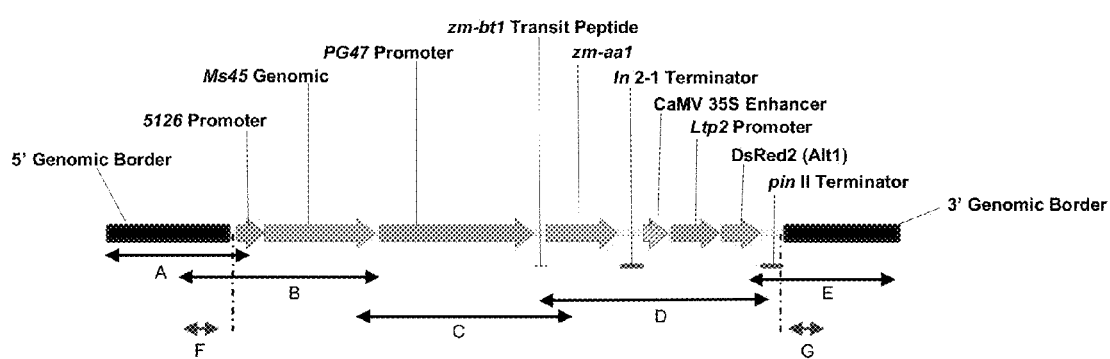
Figure 10: Schematic Representation of Insert and Genomic Border Regions Sequenced in 32138 Maize Figure 11. Complete Sequence of T-DNA Insert and Genomic Border Regions in 32138 Maize.

The 5' and 3' genomic border regions are underlined: bp 1 to 2114 and bp 11997 to 13998, respectively.

```
   1    CGAGACTTCA CTGCCAGTTG ATCGTCCCAT GAGGTTGTCA GAAATTCATG
  51    TTGCAGCTGA GCATGCACTG AAACAAACGA TATCAGATCC TGATTTTATG
 101    ACATCACTTT CATCACTAGA AGAATTTGAG GTAGTACATT CTTGCACATC
 151    ACAATTTTTT TTGAAACAAT GGCAAGAGTT CTGCCTTTCA ACCAAGGCGA
 201    AATGAATTTT TTATACAAGA AGGGGTAGCC AAACGTGATG CCTACCACAA
 251    GACACTCAAA TGGCTAACCC ACCCACGCGA CGTGGCAGAG TACAAAACTA
 301    CTATGAGTCA TTGTTGCTGA GCATGGTTGC ATAGCAGCCA ACATGTCCGG
 351    CTTACCATGG CTGATCCAGA CGACCCACTC TAATGATGTT GGGCACTCGA
 401    GCCAGAATTA AGAGTCCACT ACAGGTCATC GTTGCCAATG TCAAGCGTGC
 451    CACATAAGAG CAGCTTTGAC TTTTTATTTC GAACCCTTGG TGCCGCATAA
 501    GAGCAGCCTA TTGTGGTTCC TGCTGATGTG CCATTTCAGA TTGCATAATC
 551    TTGCTCCTAT TCCTGGTACT GAGTCTTTTA TGGGATGGTG GGAGAAGATT
 601    GACAAAAGTT CTGGAGATTG GCTATGAGGG GTCTCAATTC TCTTATTGCC
 651    TTGGGCGCCT GGATTCTTTG GAATCATTGG AATCGAATTG TCTTTGATGG
 701    ATTATCCCCT ACCCCTAGTG TTTCCGCAGC TCTCTGTCAG GCAAGGGAGA
 751    AACAACAGTT GTGGGAAATG GCAGGAGCTA AGGGTCTCTC CTTTCTTGCC
 801    GCCACCAACA GTGTCCCATA GCTGCTTGTT GTAGGGTTGT ATTTGTTTAT
 851    CATGGATCGT TTTCTTTTTC TTTGTTTTAA ACTTCCTTAG GGTTTTTTTT
 901    TGTGTGTACT GGGGTCTATT TTGGACCTTC TTTTCCTAAT ACTTAATATA
 951    ATGATGCGTA GTTCTCCTGC GCTTTCGAGA AAAAAAATCA CCACTATTGT
1001    CATCATTGTC CTATCACCCT GTAGAAGTCT CTCTAGAGGG CCATCAACGG
1051    TAGCTGCACA CAACAAACGC ATAGCTGCAT CGGCTGCCAG CCCCTCCAAT
1101    CGGGCATCAC ATGGAATCAG ATTTGATCCT GCTGCACACG TACACCACCA
1151    CACCCATAGC CATTGTCCTC ACATGTGCGC CCCGCCACAG AGGGCACCAC
1201    CCCCTGCCCT TGTGTCGCCG GATTTTCCCG CTAGGTCCTC GGCCTCGGCG
1251    CCCCGGATCG ATGCCGCTGC CATCGCCTGG GCATGGACAC CAGTGCGCCG
1301    TGCATCCGGT CCTGAGACTG AATTTTGGAC CCCAGACAAG GAAGCAGCCA
1351    TGGGCACCGT CCTGGTGGCG CCTGAGCCGC CGCAGCGACA GCATACGACA
1401    GATCCATACC AAGGGCCATC GGACCCACAC TCAAGGATGG CAGAATCCAT
1451    TCCGCTGGCG CTAGAGCCAA TGATGGCAAT GTCCCGGCAG GCCGGCATAG
1501    CTGCGCTTGC GTGCTCTCAT CGTGACCCCC AGCCTTTGGT GGCATGCTCC
1551    GGCGGTGGCG AGGGGGAGGG GTAGGGAGGA GGCTCAACGG TGCGTGCGAT
1601    GGGCTTCGCT CTAACCGTCT AGGCAGGCAA CGCAGGGGTT GGGGGGGGAA
1651    TTGCGATGCT CATCACAATA TATACACATT ATGGACTTTA ATTTTCGTAA
1701    TAATGCTTCT GTGTTTTCTT TGAACTATTT TTGTGTTACA GAAAAGATAT
1751    ATGGAGCTTA CTAAAGGTGC AGCTGACAAT TACCACCGAT CTTGGTGGAA
1801    AAGACATGGA GTTGTTCTTG ATGGAGAGAT CGCAGCTCTG TTCTTTAAGC
1851    ATGGAAATTA TGACCTGGCT GTGAAATCCT ATGAGAAAGT TTGTGCTCTC
1901    TATTCTGCAG AAGGCTGGGA AGAGCTGTTG GCAGATGTTC TTCCTGATCT
1951    TGCAGAATGC CAGAAGATTC TTAATGATGA AGCTGGTTAT TTGGCTTCTT
2001    GTGTAAAGTT ACTATCGCTG GACAGTGGCT TGTTTTCATC TAAAGAGCGG
2051    CAAGGTTTCC AGTCAGAAGT TGTTCGACTT GCTCACAGTG AAATCTGATC
2101    ATGAGCGGAG AATTAAGGCG GGAAACGACA ATCTGATCAT GAGCGGAGAA
2151    TTAAGGGAGT CACGTTATGA CCCCCGCCGA TGACGCGGGA CAAGCCGTTT
2201    TACGTTTGGA ACTGACAGAA CCGCAACGTT GAAGGAGCCA CTCAGCAAGC
2251    TTGATATCGA ATTCCTGCAG CCCTATGATT TAGAATAATA TACAAATATA
2301    TTACATAAAA AATATATTAA TTGAATTAGT GTTGTCTAAT TTATAATTAT
2351    TAGAATGTAA TTCAATTCCA ACGAAACAAC GGGGCCTTAG GTTAATATC
2401    TTCCTTACAC TGCGAAAATG TTGTTACACT TGCCAAAAAA AATCAATCGC
2451    ATATTTACCT TACAAGGACA TATTTTAGCA AAATGCTATA GACATGAATC
2501    CAACGTAATC AATAGAGTGA GATTTACTGG TAAACTACCA ATTGCTCATC
2551    TGCTCGGTAC CAACCAGCCT TTCCTATTAC CATGCACATG TTGCCTCTCA
2601    ACTGCAGCAT CTTTCAAGCC GTGAGCAGAC ATGTTGCAGA TCGAAGTAAG
```

FIG. 11A

```
2651  GTATATATGT GCATAGTCTC CTAATTCTTC ATCTTCAACC TCTAGCTGAT
2701  TGATCTCTGG TATTTACCAC TCTTTCCTTC CTTCCTTCCT TCAATTCTAA
2751  ATACCACAAA TCAAAGTTGC TTTGCCATGG AGAAGAGGAA CCTGCAGTGG
2801  CGGCGAGGGC GTGATGGCAT CGTGCAGTAC CCTCACCTCT TCTTCGCGGC
2851  CCTGGCGCTG GCCCTCCTAG TCGCGGACCC GTTCGGCCTC AGTCCGCTGG
2901  CCGAGGTCGA CTACCGGCCG GTGAAGCACG AGCTCGCGCC GTACGGGGAG
2951  GTCATGGGCA GCTGGCCCAG AGACAATGCC AGCCGGCTCA GGCGCGGGAG
3001  GCTGGAGTTC GTCGGCGAGG TGTTCGGGCC GGAGTCTATC GAGTTCGATC
3051  TCCAGGGCCG CGGGCCGTAC GCCGGCCTCG CCGACGGCCG CGTCGTGCGG
3101  TGGATGGGCG AGGAGGCCGG GTGGGAGACG TTCGCCCGTCA TCAATCCTGA
3151  CTGGTAAGTG CTCGATATCG CTCCGGCGTC CACTCGTTAC ATGCTATAAT
3201  ATAGTAGTAC TAAGATATTT TGATCTGATT TTTTGCATTC TTGGGAGAAA
3251  CGTCATGCAA AATTTGTTGT TTCTTGGCAA AGGTCAGAAG AAGTCTGTGC
3301  CAATGGAGTG AACTCAACGA CGAGGAAGCA GCACGAGAAG GAGGAGTTCT
3351  GCGGCCGGCC GCTCGGCCTG AGGTTCCACG GGGAGACCGG CGAGCTCTAC
3401  GTCGCCGACG CGTACTACGG TCTCATGGTC GTTGGCCAGA GCGGCGGCGT
3451  GGCGTCCTCC GTCGCGAGGG AAGCCGACGG GGACCCCATC CGGTTCGCGA
3501  ACGACCTCGA TGTGCACAGG AATGGATCCG TATTCTTCAC TGACACGAGC
3551  ATGAGATACA GCAGAAAGTG AGCAAAGCGA CGTAACAATC CGGCTTCTCA
3601  TTTTCAAACG CCTCTGTATT CTCTGCTGAA AGAGTAGCTC ACCAGACAAG
3651  AGCTGAATTT GCAGGGACCA TCTGAACATC CTGTTAGAAG GAGAAGGCAC
3701  CGGGAGGCTG CTCAGGTATG ATCCAGAAAC AAGCGGTGTC CATGTCGTGC
3751  TCAAGGGGCT GGTGTTCCCA ACGGCGTGC AGATCTCAGA GGACCATCAG
3801  TTTCTTCTCT TCTCCGAGAC AACAAACTGC AGGTAACAAA AATACTATCT
3851  GACGATGCTC ATGATTCTAC CGTATCCATA GTCATGAACA CAAACCACAC
3901  GAATCTGGCC TTGACCAGGA TAATGAGGTA CTGGCTGGAA GGCCCAAGAG
3951  CGGGCGAGGT AGAGGTGTTC GCGAACCTGC CGGGCTTCCC CGACAACGTG
4001  CGCTCCAACG GCAGGGGCCA GTTCTGGGTG GCGATCGACT GCTGCCGGAC
4051  GCCGGCGCAG GAGGTGTTCG CCAAGAGGCC GTGGCTCCGG ACCCTGTACT
4101  TCAAGTTCCC GCTGTCGCTC AAGGTGCTCA CTTGGAAGGC CGCCAGGAGG
4151  ATGCACACGG TGCTCGCGCT CCTCGACGGC GAAGGGCGCG TCGTGGAGGT
4201  GCTCGAGGAC CGGGGCCACG AGGTGATGAA GCTGGTGAGC GAGGTGCGGG
4251  AGGTGGGCCG CAAGCTGTGG ATCGGAACCG TGGCGCACAA CCACATCGCC
4301  ACCATCCCCT ACCCTTTAGA GGACTAACCA TGATCTATGC TGTTTCAATG
4351  CCTCCTAATC TGTGTACGTC TATAAATGTC TAATGCAGTC ACTGGTTGTA
4401  ATCTTGTTTG TGTTTGGCAA ATTGGCATAA TAATGGACAG ATTCAATGGG
4451  CATTGGTGCT GTAGTCGCAT CACACTAATT GAATGGGATC ATGTTGAGCT
4501  CTCACTTTGC TACAATTTGC TCCAGCTTGT ACGGTTGTAC CCTCTTGCTC
4551  GTCTATAGTA AGGGCCATCT AAAAAAAACT CAAATTAGAT CTGCAATACA
4601  AGTATGATTG GGCCGAATTT GGATTGTCAC GGGTCCGCGA CCGCGAATTG
4651  GGCTCGGTTT GATTTAGCCG ACATAGTAGT GACCGACCCG AGCCGGCGGC
4701  GAGCCAAACC GAGCGGACGC CGCCATGATC AAGCTATCGG ACGGCCGCTC
4751  TAGAACTAGT GGATCAGCTT GCATGCCTGC AGGTCGACTC TAGAGGATCT
4801  GCACCGGACA CTGTCTGGTG GCATACCAGA CAGTCCGGTG TGCCAGATCA
4851  GGGCACCCTT CGGTTCCTTT GCTCCTTTGC TTTTGAACCC TAACTTTGAT
4901  CGTTTATTGG TTTGTGTTGA ACCTTTATGC ACCTGTGGAA TATATAATCT
4951  AGAACAAACT AGTTAGTCCA ATCATTTGTG TTGGGCATTC AACCACCAAA
5001  ATTATTTATA GGAAAAGGTT AAACCTTATT TCCCTTTCAA TCTCCCCCTT
5051  TTTGGTGATT GATGCCAACA CAAACCAAAG AAAATATATA ACTGCAGAAT
5101  TGAACTAGTT TGCATAAGGT AAGTGCATAG GTTACTTAGA ATTAAATCAA
5151  TTTATACTTT TACTTGATAT GCATGGTTGC TTTCTTTTAT TTAACATTT
5201  TGGACCACAT TTGCACCACT TGTTTGTTT TTGCAAATC TTTTTGGAAA
5251  TTCTTTTTCA AAGTCTTTTG CAAATAGTCA AAGGTATATG AATAAGATTG
5301  TAAGAAGCAT TTTCAAGATT TGAAATTTCT CCCCCTGTTT CAAATGCTTT
5351  TCCTTTGACT AAACAAAACT CCCCCTGAAT AAAATTCTCC TCTTAGCTTT
5401  CAAGAGGGTT TTAAATAGAT ATCAATTGGA AATATATTTA GATGCTAATT
5451  TTGAAAATAT ACCAATTGAA AATCAACATA CCAATTTGAA ATTAAACATA
5501  CCAATTTAAA AAATTTCAAA AAGTGGTGGT GCGGTCCTTT TGCTTTGGGC
```

FIG. 11B

```
5551  TTAATATTTC TCCCCCTTTG GCATTAATCG CCAAAAACGG AGACTTTGTG
5601  AGCCATTTAT ACTTTCTCCC CATTGGTAAA TGAAATATGA GTGAAAGATT
5651  ATACCAAATT TGGACAGTGA TGCGGAGTGA CGGCGAAGGA TAAACGATAC
5701  CGTTAGAGTG GAGTGGAAGC CTTGTCTTCG CCGAAGACTC CATTTCCCTT
5751  TCAATCTACG ACTTAGCATA GAAATACACT TGAAAACACA TTAGTCGTAG
5801  CCACGAAAGA GATATGATCA AAGGTATACA AATGAGCTAT GTGTGTAATG
5851  TTTCAATCAA AGTTTCGAGA ATCAAGAATA TTTAGCTCAT TCCTAAGTTT
5901  GCTAAAGGTT TTATCATCTA ATGGTTTGGT AAAGATATCG ACTAATTGTT
5951  CTTTGGTGCT AACATAAGCA ATCTCGATAT CACCCCTTTG TTGGTGATCC
6001  CTCAAAAAGT GATACCGAAT GTCTATGTGC TTAGTGCGGC TGTGTTCAAC
6051  GGGATTATCC GCCATGCAGA TAGCACTCTC ATTGTCACAT AGGAGAGGGA
6101  CTTTGCTCAA TTTGTAGCCA TAGTCCCTAA GGTTTTGCCT CATCCAAAGT
6151  AATTGCACAC AACAATGTCC TGCGGCAATA TACTTGGCTT CGGCGGTAGA
6201  AAGAGCTATT GAGTTTTGTT CTTTGAAGT CCAAGACACC AGGGATCTCC
6251  CTAGAAACTG ACAAGTCCCT GATGTGCTCT TCCTATCAAT TTTACACCCT
6301  GCCCAATCGG CATCTGAATA TCCTATTAAA TCAAAGGTGG ATCCCTTGGG
6351  GTACCAAAGA CCAAATTTAG GAGTGTAAAC TAAATATCTC ATGATTCTTT
6401  TCACGGCCCT AAGGTGAACT TCCTTAGGAT CGGCTTGGAA TCTTGCACAC
6451  ATGCATATAG AAAGCATACT ATCTGGTCGA GATGCACATA AATAGAGTAA
6501  AGATCCTATC ATCGACCGGT ATACCTTTTG GTCTACGGAT TTACCTCCCG
6551  TGTCGAGGTC GAGATGCCCA TTAGTTCCCA TGGGTGTCCT GATGGGCTTG
6601  GCATCCTTCA TTCCAAACTT GTTGAGTATG TCTTGAATGT ACTTTGTTTG
6651  GCTGATGAAG GTGCCATCTT GGAGTTGCTT GACTTGAAAT CCTAGAAAAT
6701  ATTTCAACTT CCCCATCATA GACATCTCGA ATTTCGGAAT CATGATCCTA
6751  CTAAACTCTT CACAAGTAGA TTTGTTAGTA GACCCAAATA TAATATCATC
6801  AACATAAATT TGGCATACAA ACAAAACTTT TGAAATGGTT TTAGTAAAGA
6851  GAGTAGGATC GGCTTTACTG ACTCTGAAGC CATTAGTGAT AAGAAAATCT
6901  CTTAGGCATT CATACCATGC TGTTGGGCT TGCTTGAGCC CATAAAGCGC
6951  CTTTGAGAGT TTATAAACAT GGTTAGGGTA CTCACTATCT TCAAAGCCGA
7001  GAGGTTGCTC AACATAGACC TATTCACCCC ATTTGATCAC TTTTTTGGTC
7051  CTTCAGGATC TAATAGTTAT GTATAATTTA GAGTCTCTTG TTTAATGGCC
7101  AGATATTTCT AATTAATCTA AGAATTTATG ATATTTTTA ATTTTTTATC
7151  ATGTCTGATG AGAATTAACA TAAAGGCTCA ATTGGGTCCT GAATTAATAA
7201  TAGAGTGAAA ATTAATCCAG AGGCTCTATT AGAACCTTCA ATTAGTAATA
7251  CCAAGATATA TATAAGATAG TAGAGTATAG TTTAAATGTT GGCATTGTTC
7301  ATTCTTTCTT TTGTTATTTA ATTTATGCTT TCCACGGTGG TTAGTGGTTA
7351  CTTCTGAAGG GTCCAAATAA TGCATGAAGA GTTTGAGGAC AAGAAGTCTG
7401  CCCTAAAAAT AGCGATGCAA AGGCATGGTG TCCAAGCCAT ACATATAGCG
7451  CACTAATTTT ATCAGCAGAA CAATGGTATT TATAGGTCCT AGTGCCCAGG
7501  CAACAAGAGA CACGAATAAA GCATCGATCA CGACACCATG GCGGCGACAA
7551  TGGCAGTGAC GACGATGGTG ACGAGGAGCA AGGAGAGCTG GTCGTCATTG
7601  CAGGTCCCGG CGGTGGCATT CCCTTGGAAG CCACGAGGTG GCAAGACCGG
7651  CGGCCTCGAG TTCCCTCGCC GGGCGATGTT CGCCAGCGTC GGCCTCAACG
7701  TGTGCCCGGG CGTCCCGGCG GGGCGCGACC CGCGGGAGCC CGATCCCAAG
7751  GTCGTCCGGG CGGCCTGCGG CCTGGTCCAG GCACAAGTCC TCTTCCAGGG
7801  GTTTAACTGG GAGTCGTGCA AGCAGCAGGG AGGCTGGTAC AACAGGCTCA
7851  AGGCCCAGGT CGACGACATC GCCAAGGCCG GCGTCACGCA CGTCTGGCTG
7901  CCTCCACCCT CGCACTCCGT CTCGCCACAA GGCTACATGC AGGCCGCCT
7951  ATACGACCTG GACGCGTCCA GTACGGCAC GGCGGCGGAG CTCAAGTCCC
8001  TGATAGCGGC GTTCCACGGC AGGGGCGTGC AGTGCGTGGC GGACATCGTC
8051  ATCAACCACC GGTGCGCGGA AAAGAAGGAC GCGCGCGGCG TGTACTGCAT
8101  CTTCGAGGGC GGGACTCCCG ACGACCGCCT GGACTGGGGC CCCGGGATGA
8151  TCTGCAGCGA CGACACGCAG TACTCGGACG GACGGGGCA CCGCGACACG
8201  GGCGAGGGGT TCGCGGCGGC GCCCGACATC GACCACCTCA ACCCGCGCGT
8251  GCAGCGGGAG CTCTCCGCCT GGCTCAACTG GCTCAGGTCC GACGCCGTGG
8301  GGTTCGACGG CTGGCGCCTC GACTTCGCCA AGGGCTACTC GCCGGCCGTC
8351  GCCAGAATGT ACGTGGAGAG CACGGGGCCG CCGAGCTTCG TCGTCGCGGA
8401  GATATGGAAC TCGCTGAGCT ACAGCGGGGA CGGCAAGCCG GCGCCCAACC
```

FIG. 11C

```
8451  AGGACCAGTG CCGGCAGGAG CTGCTGGACT GGACGCGGGC CGTCGGCGGG
8501  CCCGCCATGG CGTTCGACTT CCCCACCAAG GGCCTGCTGC AGGCGGGCGT
8551  GCAGGGGGAG CTGTGGCGGC TGCGCGACAG CTCCGGCAAC GCGGCCGGCC
8601  TGATCGGGTG GGCGCCCGAG AAGGCCGTCA CCTTCGTCGA CAACCATGAC
8651  ACCGGGTCGA CGCAGAAGCT CTGGCCGTTC CCATCCGACA AGGTCATGCA
8701  GGGCTACGCC TACATCCTCA CCCATCCAGG AGTCCCCTGC ATTTTCTACG
8751  ACCACATGTT CGACTGGAAC CTGAAGCAGG AGATATCCAC GCTGTCTGCC
8801  ATCAGGGCGC GGAACGGCAT CCGCGCCGGG AGCAAGCTGC GGATCCTCGT
8851  GGCGGACGCG GACGCGTACG TGGCCGTCGT CGACGAGAAG GTCATGGTGA
8901  AGATCGGGAC AAGGTACGGC GTGAGCAGCG TGGTCCCGTC GGATTTCCAC
8951  CCGGCGGCGC ACGGCAAGGA CTACTGCGTC TGGGAGAAAG CGAGCCTCCG
9001  CGTCCCGGCG GGGCGCCACC TCTAGCAGCT CAGATTCCTC AGTCTTGTGC
9051  TGCATTGCAA ACACAGCAGC ACGACACTGC ATAACGTCTT TTCCTTGAGA
9101  TCTGACAAAG CAGCATTAGT CCGTTGATCG GTGGAAGACC ACTCGTCAGT
9151  GTTGAGTTGA ATGTTTGATC AATAAAATAC GGCAATGCTG TAAGGGTTGT
9201  TTTTTATGCC ATTGATAATA CACTGTACTG TTCAGTTGTT GAACTCTATT
9251  TCTTAGCCAT GCCAAGTGCT TTTCTTATTT TGAATAACAT TACAGCAAAA
9301  AGTTGAAAGA CAAAAAAAAA AACCCCCGAA CAGAGTGCTT TGGGTCCCAA
9351  GCTACTTTAG ACTGTGTTCG GCGTTCCCCC TAAATTTCTC CCCCTATATC
9401  TCACTCACTT GTCACATCAG CGTTCTCTTT CCCCTATATC TCCACGTCGA
9451  CGCGGCCGAT CCCCCGGGCT GCAGGAATTC CCATGGAGTC AAAGATTCAA
9501  ATAGAGGACC TAACAGAACT CGCCGTAAAG ACTGGCGAAC AGTTCATACA
9551  GAGTCTCTTA CGACTCAATG ACAAGAAGAA AATCTTCGTC AACATGGTGG
9601  AGCACGACAC GCTTGTCTAC TCCAAAAATA TCAAAGATAC AGTCTCAGAA
9651  GACCAAAGGG CAATTGAGAC TTTTCAACAA AGGGTAATAT CCGGAAACCT
9701  CCTCGGATTC CATTGCCCAG CTATCTGTCA CTTTATTGTG AAGATAGTGG
9751  AAAAGGAAGG TGGCTCCTAC AAATGCCATC ATTGCGATAA AGGAAAGGCC
9801  ATCGTGAAG ATGCCTCTGC CGACAGTGGT CCCAAAGATG GACCCCCACC
9851  CACGAGGAGC ATCGTGGAAA AAGAAGACGT TCCAACCACG TCTTCAAAGC
9901  AAGTGGATTG ATGTGATATC TCCACTGACG TAAGGGATGA CGCACAATCC
9951  CACTAAGCTG ACCGAAGCTG GCCGCTCTAG AACTAGTGGA TCTCGATGTG
10001 TAGTCTACGA GAAGGGTTAA CCGTCTCTTC GTGAGAATAA CCGTGGCCTA
10051 AAAATAAGCC GATGAGGATA ATAAAATGT GGTGGTACAG TACTTCAAGA
10101 GGTTTACTCA TCAAGAGGAT GCTTTTCCGA TGAGCTCTAG TAGTACATCG
10151 GACCTACAT ACCTCCATTG TGGTGAAATA TTTTGTGCTC ATTTAGTGAT
10201 GGGTAAATTT TGTTTATGTC ACTCTAGGTT TTGACATTTC AGTTTTGCCA
10251 CTCTTAGGTT TTGACAAATA ATTTCCATTC CGCGGCAAAA GCAAACAAT
10301 TTTATTTTAC TTTTACCACT CTTAGCTTTC ACAATGTATC ACAAATGCCA
10351 CTCTAGAAAT TCTGTTTATG CCACAGAATG TGAAAAAAAA CACTCACTTA
10401 TTTGAAGCCA AGGTGTTCAT GGCATGAAA TGTGACATAA AGTAACGTTC
10451 GTGTATAAGA AAAAATTGTA CTCCTCGTAA CAAGAGACGG AAACATCATG
10501 AGACAATCGC GTTTGGAAGG CTTTGCATCA CCTTTGGATG ATGCGCATGA
10551 ATGGAGTCGT CTGCTTGCTA GCCTTCGCCT ACCGCCCACT GAGTCCGGGC
10601 GGCAACTACC ATCGGCGAAC GACCCAGCTG ACCTCTACCG ACCGGACTTG
10651 AATGCGCTAC CTTCGTCAGC GACGATGGCC GCGTACGCTG GCGACGTGCC
10701 CCCGCATGCA TGGCGGCACA TGGCGAGCTC AGACCGTGCG TGGCTGGCTA
10751 CAAATACGTA CCCCGTGAGT GCCCTAGCTA GAAACTTACA CCTGCAACTG
10801 CGAGAGCGAG CGTGTGAGTG TAGCCGAGTA GATCCCCCGG GCTGCAGGTC
10851 GACTCTAGAG GATCCACCGG TCGCCACCAT GGCCTCCTCC GAGAACGTCA
10901 TCACCGAGTT CATGCGCTTC AAGGTGCGCA TGGAGGGCAC CGTGAACGGC
10951 CACGAGTTCG AGATCGAGGG CGAGGGCGAG GCCGCCCCT ACGAGGGCCA
11001 CAACACCGTG AAGCTGAAGG TGACGAAGGG CGGCCCCCTG CCCTTCGCCT
11051 GGGACATCCT GTCCCCCCAG TTCCAGTACG GCTCCAAGCT GTACGTGAAG
11101 CACCCCGCCG ACATCCCCGA CTACAAGAAG CTGTCCTTCC CCGAGGGCTT
11151 CAAGTGGGAG CGCGTGATGA ACTTCGAGGA CGGCGGCGTG GCGACCGTGA
11201 CCCAGGACTC CTCCCTGCAG GACGGCTGCT TCATCTACAA GGTGAAGTTC
11251 ATCGGCGTGA ACTTCCCCTC CGACGGCCCC GTGATGCAGA AGAAGACCAT
11301 GGGCTGGGAG GCCTCCACCG AGCGCCTGTA CCCCCGCGAC GGCGTGCTGA
```

FIG. 11D

```
11351   AGGGCGAGAC CCACAAGGCC CTGAAGCTGA AGGACGGCGG CCACTACCTG
11401   GTGGAGTTCA AGTCCATCTA CATGGCCAAG AAGCCCGTGC AGCTGCCCGG
11451   CTACTACTAC GTGGACGCCA AGCTGGACAT CACCTCCCAC AACGAGGACT
11501   ACACCATCGT GGAGCAGTAC GAGCGCACCG AGGGCCGCCA CCACCTGTTC
11551   CTGTAGCGGC CCATGGATAT TCGAACGCGT AGGTACCACA TGGTTAACCT
11601   AGACTTGTCC ATCTTCTGGA TTGGCCAACT TAATTAATGT ATGAAATAAA
11651   AGGATGCACA CATAGTGACA TGCTAATCAC TATAATGTGG GCATCAAAGT
11701   TGTGTGTTAT GTGTAATTAC TAGTTATCTG AATAAAAGAG AAAGAGATCA
11751   TCCATATTTC TTATCCTAAA TGAATGTCAC GTGTCTTTAT AATTCTTTGA
11801   TGAACCAGAT GCATTTCATT AACCAAATCC ATATACATAT AAATATTAAT
11851   CATATATAAT TAATATCAAT TGGGTTAGCA AAACAAATCT AGTCTAGGTG
11901   TGTTTTGCGA ATGCGGCCGC CACCGCGGTG GAGCTCGAAT TCAGTACATT
11951   AAAAACGTCC GCAATGTGTT ATTAAGTTGT CTAAGCGTCA ATTTGTGATG
12001   GAGATCCTGG TACACTATCT GTAGCAGTTT GGAATGGCTT CCCAGATGAC
12051   ATCACACTGG AGTCTCTCAG TTTAAGGTTG TCAGCTTCTT CTAGTGCAGA
12101   TGAAGGTATC AAGGTACAAG TACTGTGTTA GCATTACTGA TTGCTACCCT
12151   TTTCCTCTGT GGCATGTCTT ATTCTGTTAT TCATGGTTTG GATGCACTAA
12201   TATGTTTTCA AGTAAAATTC AGTTCCATCC TTGCAGAACA GATTTCATAA
12251   ATCAAAACTA CTATGATAAA GTATATCAAA CTCTAGAGAA ATGACCGCAC
12301   ATAACATATT CTTCAGTCAC CTAATGGTTT AATGTTGTCA TCCATGCAGG
12351   CAATTAAAAG TTCAGATTCT CATGTTCTAG TACCAGGTAG AAATATCATC
12401   TCTTTTGACA TTCCTCGTCA AAAGCCTGGC TCCTATGTGT TGGGTGCTCT
12451   CACTGGACAG ATTGGCAAGC TGTCATTCAG ATCACATGGA TTTTCCCAAG
12501   ATGGTCCAGT TGAAACTGAT GAATTATGA GCTTTGAGAA ACCGACAAGA
12551   CCTGTTTTGA AGGTAATTGC TAAAATGAGC TGAAGATTAC TTAGAAGTTT
12601   TCGTGGGGC ATGACTGGAG CTAGATCCCT TAGAAGTTTC TGGCCTTAAG
12651   TTTTTGGGG TTTCCCCTTA AGATTTTTTT TTTCTTTTTC CCCATTTTTC
12701   CATAACTGGC ACCTTGTATT GGGTCTATTT TAGGCCTTTC TTTCTCTTCT
12751   TAATATATTG ATGTACAGTT CTCCTACAGT TCGAGAAAAA AAGAGCTGAC
12801   GATCTGAACT GTTTTATAAA ATCGTAGCCC TACCCCATGT CACTAAACTG
12851   CCATAAGAGA TACTATCCAT ACTTTCAAAA CAAAACCGGA GCATAGTTTC
12901   CTCTAATTAG TGAACATGGT CAGTTATATT GTTAAGACA GATATGTTCT
12951   CATTGCATTT GTTTCTCTGT TGTAGGTGAG AAAACCAAGG GCTTTAGTTG
13001   ATATTACACC TGCTGTGTCC TCTGCTTTGC TTATGAATGA GCTCCAATGG
13051   ATTGGATTAA TCGTTAAGCC TATAGACTAT TCTTTAAAAG GTGGAATATT
13101   GCATATCGAT GCTGGCGCTG AACTGAAAAT TGAGGAGTCT CAGATGATTG
13151   AAATAGAAAT TTACGTAAGT GATATGGAGT GTGCTAATTC TGCCAACAGC
13201   TCCATCAAAG CTGGAAAGGT TGAAAAGGTA CCTATTGAAA ATGGAAAGAT
13251   AGAACTTCCT GATTGGGCTA GTGATGTGAC TACTCTTGTT TGGTTTCCTG
13301   TTCGTGCTAT TGATGACACA ATTGCAAGAG GAGAATCCCT AGGTCTGTAT
13351   GTAACAAGTC ATAAATTCAC TATGTTATGT TTCAATCAGT TAGTTGACCT
13401   TTCTTTGTCC TTGTTTCAGT GTCTCAGAAA CAGAGCGTTG TAGATGGGAT
13451   GAGAATGATT GCTCTCAAGC TTGAGTTTGG AGTTTTCCGT AACCAAGTGT
13501   TTGAAAGGTA TCTCTCTGTT TTTCCCCTCA ACATGCAGA AGAGCTGTGT
13551   CATGTCTGCC ATTGTATAAG AAAAGATGAG ATACTTCGAT ACATTGAACT
13601   TTAGATATAG ATACTCAACA AATTTATTAT TATGATTTTC AGGACCATTG
13651   CAGTTCATTT TACTAACCCA TTCCATGTAA GCACACGCGT CGTGGACAAG
13701   TGCAATGATG GAGCTCTACT CTACAGGTA AAGTTCTTTC TTGTCTGGCA
13751   CATGATTGTC ATTGTTGTAT TCCTAGATTT AAAACACACA CACACACACA
13801   CATATATATA CAGGGATATT GGGAGCCCTG CTCTTCCAAA CATATATACT
13851   AGAAGCCCCA GCCGTGCCCT GCACCACCCG ACCGGCTTGG CCACCTAGAT
13901   CCCGTGCACA CGTCCATCCC CTGCATGCGG ATATTTGTTT CCATTTGCAT
13951   GTGCGAAAAA TTTGGAAGGT GTATCTGTTT CCTGCTGCAT GCGCATAA
```

FIG. 11E

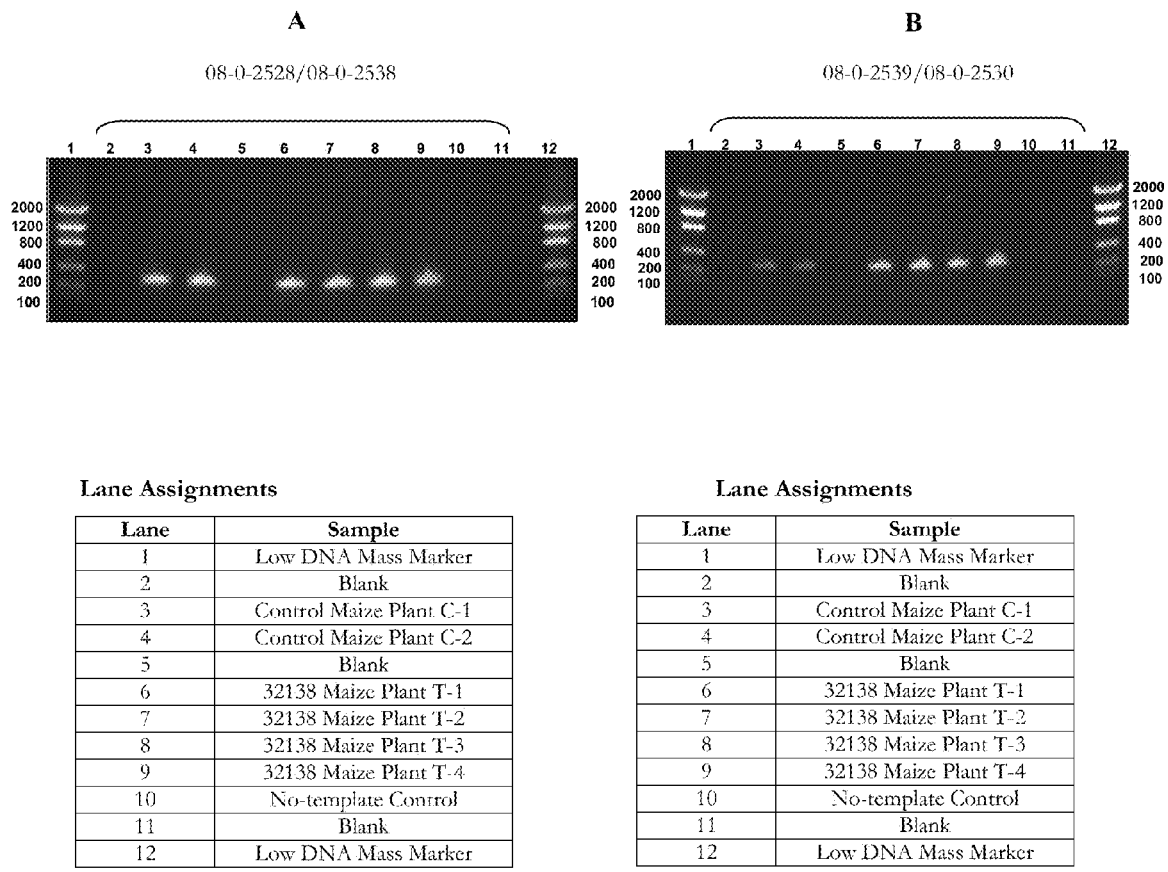
Figure 12: PCR Analysis of the 5' and 3' Genomic Border Regions in 32138 Maize and Control Maize Plants.
12A: Primer pair 08-0-2528/08-0-2538 amplifies a PCR product (294 bp) from within the 5' flanking genomic DNA. 12B: Primer pair 08-0-2539/08-0-2530 amplifies a PCR product (297 bp) from within the 3' genomic border region.

Figure 13. Plasmid map of PHP24597
The location of the probes used for Southern analysis is indicated as lettered boxes inside the plasmid map. A: RB probe; B: LB probe; C: *spc* probe; D: *virG* probe; E: *tet* probe.
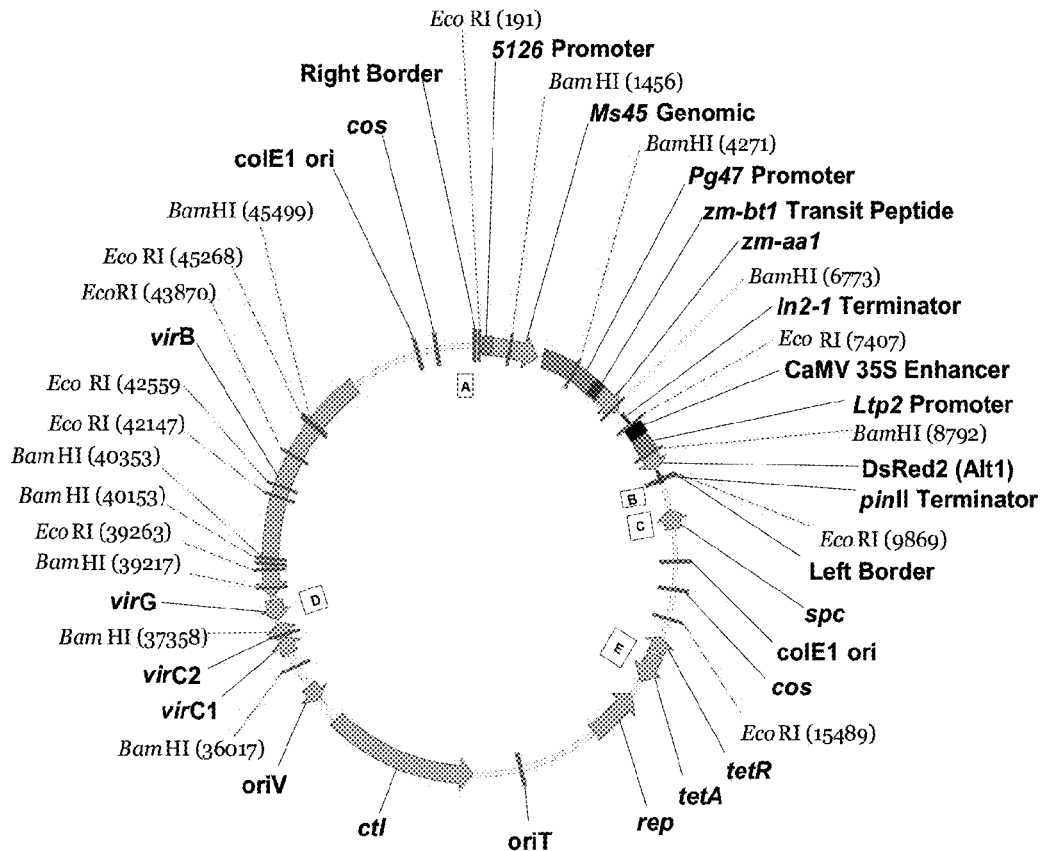
The locations of additional enzymes used for analysis are given below:
| Enzyme | Locations (bp) |
|---|---|
| Bmt I | 8503, 36160, 38359, 39502, 45917 |
| Hind III | 179, 34837, 45900, 46809, 47930, 49445 |

Figure 14. Map of T-DNA Region from Plasmid PHP24597
The locations of the probes used are shown as numbered boxes below the map and are identified below:
| Number | Probe Name |
|--------|------------|
| 1 | *5126* promoter |
| 2 | *Ms45* |
| 3 | *Pg47* promoter |
| 4 | *zm-bt1* |
| 5 | *zm-aa1* |
| 6 | *In2-1* terminator |
| 7 | 35S enhancer |
| 8 | *Ltp2* promoter |
| 9 | *DsRed2(Alt1)* |
| 10 | *pinII* terminator |
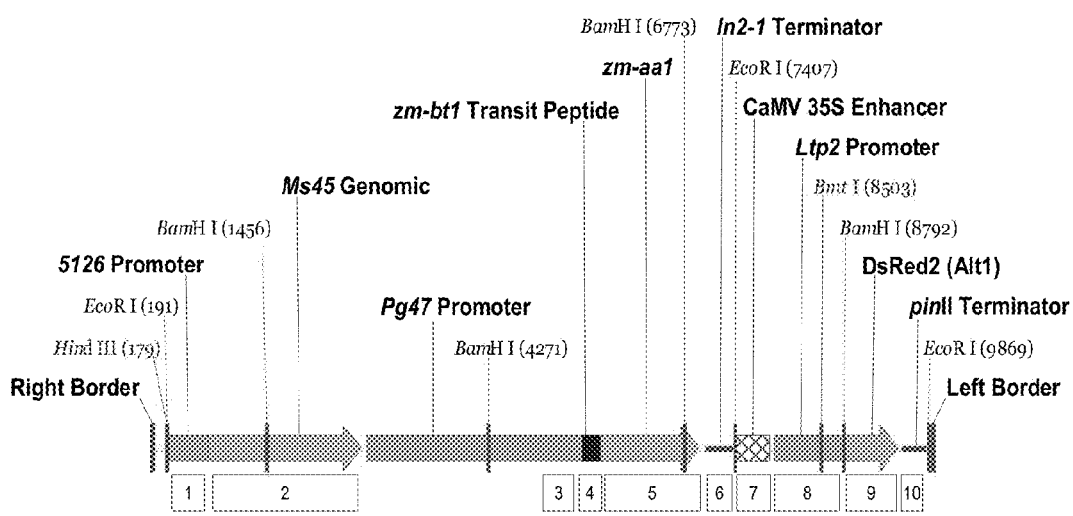

SEQUENCE LISTING

```
<160> NUMBER OF SEQ ID NOS: 37

<210> SEQ ID NO 1
<211> LENGTH: 13998
<212> TYPE: DNA
<213> ORGANISM: Complete Artificial Sequence
<220> FEATURE:
<223> OTHER INFORMATION: complete sequence of T-DNA insert and genomic
      borders regions in 32138 Zea mays
<220> FEATURE:
<221> NAME/KEY: misc_feature
<222> LOCATION: (1)...(2114)
<223> OTHER INFORMATION: flanking sequence
<220> FEATURE:
<221> NAME/KEY: misc_feature
<222> LOCATION: (11997)...(13998)
<223> OTHER INFORMATION: flanking sequence
<220> FEATURE:
<221> NAME/KEY: misc_feature
<222> LOCATION: (2115)...(11996)
<223> OTHER INFORMATION: T-DNA insert

<400> SEQUENCE: 1
cgagacttca ctgccagttg atcgtcccat gaggttgtca gaaattcatg ttgcagctga      60
gcatgcactg aaacaaacga tatcagatcc tgattttatg acatcacttt catcactaga     120
agaatttgag gtagtacatt cttgcacatc acaatttttt ttgaaacaat ggcaagagtt     180
```

```
ctgcctttca accaaggcga aatgaattt  ttatacaaga aggggtagcc aaacgtgatg    240
cctaccacaa gacactcaaa tggctaaccc acccacgcga cgtggcagag tacaaaacta    300
ctatgagtca ttgttgctga gcatggttgc atagcagcca acatgtccgg cttaccatgg    360
ctgatccaga cgacccactc taatgatgtt gggcactcga gccagaatta agagtccact    420
acaggtcatc gttgccaatg tcaagcgtgc cacataagag cagctttgac ttttatttc     480 gaacccttgg tgccgcataa gagcagccta ttgtggttcc tgctgatgtg ccatttcaga    540
ttgcataatc ttgctcctat tcctggtact gagtctttta tgggatggtg ggagaagatt    600
gacaaaagtt ctggagattg gctatgaggg gtctcaattc tcttattgcc ttgggcgcct    660
ggattctttg gaatcattgg aatcgaattg tctttgatgg attatcccct accctagtg     720 tttccgcagc tctctgtcag gcaagggaga acaacagtt gtgggaaatg gcaggagcta    780
agggtctctc ctttcttgcc gccaccaaca gtgtcccata gctgcttgtt gtagggttgt    840
atttgtttat catggatcgt tttctttttc tttgttttaa acttccttag gttttttt      900 tgtgtgtact ggggtctatt ttggacccttc ttttcctaat acttaatata atgatgcgta   960
gttctcctgc gctttcgaga aaaaaaatca ccactattgt catcattgtc ctatcaccct    1020
gtagaagtct ctctagaggg ccatcaacgg tagctgcaca caacaaacgc atagctgcat    1080
cggctgccag cccctccaat cgggcatcac atggaatcag atttgatcct gctgcacacg    1140
tacaccacca cacccatagc cattgtcctc acatgtgcgc cccgccacag agggcaccac    1200
cccctgccct tgtgtcgccg gatttccccg ctaggtcctc ggcctcggcg ccccggatcg    1260
atgccgctgc catcgcctgg gcatggacac cagtgcgccg tgcatccggt cctgagactg    1320
aattttggac cccagacaag gaagcagcca tgggcaccgt cctggtggcg cctgagccgc    1380
cgcagcgaca gcatacgaca gatccatacc aagggccatc ggacccacac tcaaggatgg    1440
cagaatccat tccgctggcg ctagagccaa tgatggcaat gtcccggcag gccggcatag    1500
ctgcgcttgc gtgctctcat cgtgaccccc agcctttggt ggcatgctcc ggcggtggcg    1560
agggggaggg gtagggagga ggctcaacgg tgcgtgcgat gggcttcgct ctaaccgtct    1620
aggcaggcaa cgcaggggtt ggggggggaa ttgcgatgct catcacaata tatacacatt    1680
atggacttta atttcgtaa taatgcttct gtgttttctt tgaactattt ttgtgttaca     1740
gaaaagatat atggagctta ctaaaggtgc agctgacaat taccaccgat cttggtggaa    1800
aagacatgga gttgttcttg atggagagat cgcagctctg ttctttaagc atggaaatta    1860
tgacctggct gtgaaatcct atgagaaagt ttgtgctctc tattctgcag aaggctggga    1920
agagctgttg gcagatgttc ttcctgatct tgcagaatgc cagaagattc ttaatgatga    1980
agctggttat ttggcttctt gtgtaaagtt actatcgctg acagtggct tgttttcatc     2040 taaagagcgg caaggtttcc agtcagaagt tgttcgactt gctcacagtg aaatctgatc    2100
atgagcggag aattaaggcg ggaaacgaca atctgatcat gagcggagaa ttaagggagt    2160
cacgttatga ccccgccga tgacgcggga caagccgttt acgtttgga actgacagaa      2220 ccgcaacgtt gaaggagcca ctcagcaagc ttgatatcga attcctgcag ccctatgatt    2280
tagaataata tacaaatata ttacataaaa aatatattaa ttgaattagt gttgtctaat    2340
ttataattat tagaatgtaa ttcaattcca acgaaacaac ggggccttag gtttaatatc    2400
ttccttacac tgcgaaaatg ttgttacact tgccaaaaaa aatcaatcgc atatttacct    2460
tacaaggaca tattttagca aaatgctata gacatgaatc caacgtaatc aatagagtga    2520
gatttactgg taaactacca attgctcatc tgctcggtac caaccagcct ttcctattac    2580
```

```
catgcacatg ttgcctctca actgcagcat ctttcaagcc gtgagcagac atgttgcaga    2640
tcgaagtaag gtatatatgt gcatagtctc ctaattcttc atcttcaacc tctagctgat    2700
tgatctctgg tatttaccac tctttccttc cttccttcct tcaattctaa ataccacaaa    2760
tcaaagttgc tttgccatgg agaagaggaa cctgcagtgg cggcgagggc gtgatggcat    2820
cgtgcagtac cctcacctct tcttcgcggc cctggcgctg ccctcctag tcgcggaccc     2880 gttcggcctc agtccgctgg ccgaggtcga ctaccggccg gtgaagcacg agctcgcgcc    2940
gtacggggag gtcatgggca gctggcccag agacaatgcc agccggctca ggcgcgggag    3000
gctggagttc gtcggcgagg tgttcgggcc ggagtctatc gagttcgatc tccagggccg    3060
cgggccgtac gccggcctcg ccgacggccg cgtcgtgcgg tggatgggcg aggaggccgg    3120
gtgggagacg ttcgccgtca tgaatcctga ctggtaagtg ctcgatatcg ctccggcgtc    3180
cactcgttac atgctataat atagtagtac taagatattt tgatctgatt ttttgcattc    3240
ttgggagaaa cgtcatgcaa aatttgttgt ttcttggcaa aggtcagaag aagtctgtgc    3300
caatggagtg aactcaacga cgaggaagca gcacgagaag gaggagttct gcggccggcc    3360
gctcggcctg aggttccacg gggagaccgg cgagctctac gtcgccgacg cgtactacgg    3420
tctcatggtc gttggccaga gcggcggcgt ggcgtcctcc gtcgcgaggg aagccgacgg    3480
ggaccccatc cggttcgcga acgacctcga tgtgcacagg aatggatccg tattcttcac    3540
tgacacgagc atgagataca gcagaaagtg agcaaagcga cgtaacaatc cggcttctca    3600
ttttcaaacg cctctgtatt ctctgctgaa agagtagctc accagacaag agctgaattt    3660
gcagggacca tctgaacatc ctgttagaag gagaaggcac cgggaggctg ctcaggtatg    3720
atccagaaac aagcggtgtc catgtcgtgc tcaaggggct ggtgttccca aacggcgtgc    3780
agatctcaga ggaccatcag tttcttctct tctccgagac aacaaactgc aggtaacaaa    3840
aatactatct gacgatgctc atgattctac cgtatccata gtcatgaaca caaaccacac    3900
gaatctggcc ttgaccagga taatgaggta ctggctggaa ggcccaagag cgggcgaggt    3960
agaggtgttc gcgaacctgc cgggcttccc cgacaacgtg cgctccaacg gcaggggcca    4020
gttctgggtg gcgatcgact gctgccggac gccggcgcag gaggtgttcg ccaagaggcc    4080
gtggctccgg accctgtact tcaagttccc gctgtcgctc aaggtgctca cttggaaggc    4140
cgccaggagg atgcacacgg tgctcgcgct cctcgacggc gaagggcgcg tcgtggaggt    4200
gctcgaggac cggggccacg aggtgatgaa gctggtgagc gaggtgcggg aggtgggccg    4260
caagctgtgg atcggaaccg tggcgcacaa ccacatcgcc accatcccct accctttaga    4320
ggactaacca tgatctatgc tgtttcaatg cctcctaatc tgtgtacgtc tataaatgtc    4380
taatgcagtc actggttgta atcttgtttg tgtttggcaa attggcataa taatggacag    4440
attcaatggg cattggtgct gtagtcgcat cacactaatt gaatgggatc atgttgagct    4500
ctcactttgc tacaatttgc tccagcttgt acgttgtac cctcttgctc gtctatagta     4560
agggccatct aaaaaaaact caaattagat ctgcaataca agtatgattg ggccgaattt    4620
ggattgtcac gggtccgcga ccgcgaattg ggctcggttt gatttagccg acatagtagt    4680
gaccgacccg agccggcggc gagccaaacc gagcggacgc cgccatgatc aagctatcgg    4740
acggccgctc tagaactagt ggatcagctt gcatgcctgc aggtcgactc tagaggatct    4800
gcaccggaca ctgtctggtg gcataccaga cagtccggtg tgccagatca gggcacccct    4860
cggttccttt gctcctttgc ttttgaaccc taactttgat cgtttattgg tttgtgttga    4920
```

```
accctttatgc acctgtggaa tatataatct agaacaaact agttagtcca atcatttgtg    4980
ttgggcattc aaccaccaaa attatttata ggaaaaggtt aaaccttatt tcccttcaa      5040 tctcccccctt tttggtgatt gatgccaaca caaaccaaag aaaatatata agtgcagaat    5100
tgaactagtt tgcataaggt aagtgcatag gttacttaga attaaatcaa tttatacttt     5160
tacttgatat gcatggttgc tttctttat tttaacattt tggaccacat ttgcaccact      5220
tgttttgttt tttgcaaatc ttttttggaaa ttcttttttca aagtcttttg caaatagtca   5280
aaggtatatg aataagattg taagaagcat tttcaagatt tgaaatttct cccctgttt      5340 caaatgcttt tcctttgact aaacaaaact ccccctgaat aaaattctcc tcttagctt      5400 caagagggtt ttaaatagat atcaattgga aatatattta gatgctaatt ttgaaaatat     5460
accaattgaa atcaacata ccaatttgaa attaaacata ccaatttaaa aaatttcaaa      5520
aagtggtggt gcggtccttt tgctttgggc ttaatatttc tcccccttg gcattaatcg      5580 ccaaaaacgg agactttgtg agccatttat actttctccc cattggtaaa tgaaatatga    5640
gtgaaagatt ataccaaatt tggacagtga tgcggagtga cggcgaagga taaacgatac    5700
cgttagagtg gagtggaagc cttgtcttcg ccgaagactc catttcctt tcaatctacg     5760 acttagcata gaaatacact tgaaaacaca ttagtcgtag ccacgaaaga gatatgatca    5820
aaggtataca aatgagctat gtgtgtaatg tttcaatcaa agtttcgaga atcaagaata    5880
tttagctcat tcctaagttt gctaaaggtt ttatcatcta atggtttggt aaagatatcg    5940
actaattgtt ctttggtgct aacataagca atctcgatat cacccctttg ttggtgatcc    6000 ctcaaaagt gataccgaat gtctatgtgc ttagtgcggc tgtgttcaac gggattatcc      6060
gccatgcaga tagcactctc attgtcacat aggagaggga ctttgctcaa tttgtagcca    6120
tagtccctaa ggttttgcct catccaaagt aattgcacac aacaatgtcc tgcggcaata    6180
tacttggctt cggcggtaga aagagctatt gagttttgtt tctttgaagt ccaagacacc    6240
agggatctcc ctagaaactg acaagtccct gatgtgctct tcctatcaat tttacaccct    6300
gcccaatcgg catctgaata tcctattaaa tcaaggtgg atcccttggg gtaccaaaga    6360
ccaaatttag gagtgtaaac taaatatctc atgattcttt tcacggcct aaggtgaact     6420 tccttaggat cggcttggaa tcttgcacac atgcatatag aaagcatact atctggtcga    6480
gatgcacata aatagagtaa agatcctatc atcgaccggt ataccttttg gtctacggat    6540
ttacctcccg tgtcgaggtc gagatgccca ttagttccca tgggtgtcct gatgggcttg    6600
gcatccttca ttccaaactt gttgagtatg tcttgaatgt actttgttg gctgatgaag     6660 gtgccatctt ggagttgctt gacttgaaat cctagaaaat atttcaactt ccccatcata    6720
gacatctcga atttcggaat catgatccta ctaaactctt cacaagtaga tttgttagta    6780
gacccaaata taatatcatc aacataaatt tggcatacaa acaaaacttt tgaaatggtt    6840
ttagtaaaga gagtaggatc ggcttttactg actctgaagc cattagtgat aagaaaatct    6900
cttaggcatt cataccatgc tgttggggct tgcttgagcc cataaagcgc ctttgagagt    6960
ttataaacat ggttagggta ctcactatct tcaaagccga gaggttgctc aacatagacc    7020
tattcacccc atttgatcac ttttttggtc cttcaggatc taatagttat gtataattta    7080
gagtctcttg tttaatggcc agatatttct aattaatcta agaatttatg atattttta    7140 atttttattatc atgtctgatg agaattaaca taaaggctca attgggtcct gaattaataa    7200
tagagtgaaa attaatccag aggctctatt agaaccttca attagtaata ccaagatata    7260
tataagatag tagagtatag tttaaatgtt ggcattgttc attctttctt tgttatttta    7320
```

```
atttatgctt tccacggtgg ttagtggtta cttctgaagg gtccaaataa tgcatgaaga    7380
gtttgaggac aagaagtctg ccctaaaaat agcgatgcaa aggcatggtg tccaagccat    7440
acatatagcg cactaatttt atcagcagaa caatggtatt tataggtcct agtgcccagg    7500
caacaagaga cacgaataaa gcatcgatca cgacaccatg gcggcgacaa tggcagtgac    7560
gacgatggtg acgaggagca aggagagctg gtcgtcattg caggtcccgg cggtggcatt    7620
cccttggaag ccacgaggtg gcaagaccgg cggcctcgag ttccctcgcc gggcgatgtt    7680
cgccagcgtc ggcctcaacg tgtgcccggg cgtcccggcg gggcgcgacc cgcgggagcc    7740
cgatcccaag gtcgtccggg cggcctgcgg cctggtccag gcacaagtcc tcttccaggg    7800
gtttaactgg gagtcgtgca agcagcaggg aggctggtac aacaggctca aggcccaggt    7860
cgacgacatc gccaaggccg gcgtcacgca cgtctggctg cctccaccct cgcactccgt    7920
ctcgccacaa ggctacatgc caggccgcct atacgacctg gacgcgtcca agtacggcac    7980
ggcggcggag ctcaagtccc tgatagcggc gttccacggc aggggcgtgc agtgcgtggc    8040
ggacatcgtc atcaaccacc ggtgcgcgga aaagaaggac gcgcgcggcg tgtactgcat    8100
cttcgagggc gggactcccg acgaccgcct ggactgggc cccgggatga tctgcagcga    8160
cgacacgcag tactcggacg ggacggggca ccgcgacacg ggcgaggggt tcgcggcggc    8220
gcccgacatc gaccacctca acccgcgcgt gcagcgggag ctctccgcct ggctcaactg    8280
gctcaggtcc gacgccgtgg ggttcgacgg ctggcgcctc gacttcgcca agggctactc    8340
gccgccgtc gccagaatgt acgtggagag cacggggccg ccgagcttcg tcgtcgcgga    8400
gatatggaac tcgctgagct acagcgggga cggcaagccg gcgcccaacc aggaccagtg    8460
ccggcaggag ctgctggact ggacgcgggc cgtcggcggg cccgccatgg cgttcgactt    8520
ccccaccaag ggcctgctgc aggcgggcgt gcaggggag ctgtggcggc tgcgcgacag    8580
ctccggcaac gcggccggcc tgatcgggtg ggcgcccgag aaggccgtca ccttcgtcga    8640
caaccatgac accgggtcga cgcagaagct ctggccgttc ccatccgaca aggtcatgca    8700
gggctacgcc tacatcctca cccatccagg agtcccctgc atttctacg accacatgtt    8760
cgactggaac ctgaagcagg agatatccac gctgtctgcc atcagggcgc ggaacggcat    8820
ccgcgccggg agcaagctgc ggatcctcgt ggcggacgcg gacgcgtacg tggccgtcgt    8880
cgacgagaag gtcatggtga agatcgggac aaggtacggc gtgagcagcg tggtcccgtc    8940
ggatttccac ccggcggcgc acggcaagga ctactgcgtc tgggagaaag cgagcctccg    9000
cgtcccggcg gggcgccacc tctagcagct cagattgctc agtcttgtgc tgcattgcaa    9060
acacagcagc acgacactgc ataacgtctt ttccttgaga tctgacaaag cagcattagt    9120
ccgttgatcg gtggaagacc actcgtcagt gttgagttga atgtttgatc aataaaatac    9180
ggcaatgctg taagggttgt tttttatgcc attgataata cactgtactg ttcagttgtt    9240
gaactctatt tcttagccat gccaagtgct tttcttattt tgaataacat tacagcaaaa    9300
agttgaaaga caaaaaaaaa aaccccccgaa cagagtgctt tgggtcccaa gctactttag    9360
actgtgttcg gcgttccccc taaatttctc cccctatatc tcactcactt gtcacatcag    9420
cgttctcttt cccctatatc tccacgtcga cgcggccgat ccccccgggct gcaggaattc    9480
ccatggagtc aaagattcaa atagaggacc taacagaact cgccgtaaag actggcgaac    9540
agttcataca gagtctctta cgactcaatg acaagaagaa atcttcgtc aacatggtgg    9600
agcacgacac gcttgtctac tccaaaaata tcaaagatac agtctcagaa gaccaaaggg    9660
```

```
caattgagac ttttcaacaa agggtaatat ccggaaacct cctcggattc cattgcccag    9720
ctatctgtca ctttattgtg aagatagtgg aaaaggaagg tggctcctac aaatgccatc    9780
attgcgataa aggaaaggcc atcgttgaag atgcctctgc cgacagtggt cccaaagatg    9840
gaccccacc cacgaggagc atcgtggaaa agaagacgt tccaaccacg tcttcaaagc      9900
aagtggattg atgtgatatc tccactgacg taagggatga cgcacaatcc cactaagctg    9960
accgaagctg gccgctctag aactagtgga tctcgatgtg tagtctacga gaagggttaa   10020
ccgtctcttc gtgagaataa ccgtggccta aaaataagcc gatgaggata aataaaatgt   10080
ggtggtacag tacttcaaga ggtttactca tcaagaggat gcttttccga tgagctctag   10140
tagtacatcg gacctcacat acctccattg tggtgaaata ttttgtgctc atttagtgat   10200
gggtaaattt tgtttatgtc actctaggtt ttgacatttc agttttgcca ctcttaggtt   10260
ttgacaaata atttccattc cgcggcaaaa gcaaacaat tttatttac ttttaccact    10320
cttagctttc acaatgtatc acaaatgcca ctctagaaat tctgtttatg ccacagaatg   10380
tgaaaaaaa cactcactta tttgaagcca aggtgttcat ggcatggaaa tgtgacataa    10440
agtaacgttc gtgtataaga aaaaattgta ctcctcgtaa caagagacgg aaacatcatg   10500
agacaatcgc gtttggaagg cttttgcatca cctttggatg atgcgcatga atggagtcgt  10560
ctgcttgcta gccttcgcct accgcccact gagtccgggc ggcaactacc atcggcgaac   10620
gacccagctg acctctaccg accggacttg aatgcgctac cttcgtcagc gacgatggcc   10680
gcgtacgctg gcgacgtgcc cccgcatgca tggcggcaca tggcgagctc agaccgtgcg   10740
tggctggcta caaatacgta ccccgtgagt gccctagcta gaaacttaca cctgcaactg   10800
cgagagcgag cgtgtgagtg tagccgagta gatccccccgg gctgcaggtc gactctagag   10860
gatccaccg tcgccaccat ggcctcctcc gagaacgtca tcaccgagtt catgcgcttc    10920
aaggtgcgca tggagggcac cgtgaacggc cacgagttcg agatcgaggg cgagggcgag   10980
ggccgcccct acgagggcca caacaccgtg aagctgaagg tgacgaaggg cggcccctg    11040
cccttcgcct gggacatcct gtccccccag ttccagtacg gctccaaggt gtacgtgaag   11100
caccccgccg acatccccga ctacaagaag ctgtccttcc ccgagggctt caagtgggag   11160
cgcgtgatga acttcgagga cggcggcgtg gcgaccgtga cccaggactc ctccctgcag   11220
gacggctgct tcatctacaa ggtgaagttc atcggcgtga acttcccctc cgacggcccc   11280
gtgatgcaga agaagaccat gggctgggag gcctccaccg agcgcctgta ccccgcgac    11340
ggcgtgctga agggcgagac ccacaaggcc ctgaagctga aggacggcgg ccactacctg   11400
gtggagttca gtccatccta catggccaag aagcccgtgc agctgcccgg ctactactac   11460
gtggacgcca agctggacat caccctccac aacgaggact acaccatcgt ggagcagtac   11520
gagcgcaccg agggccgcca ccacctgttc ctgtagcggc ccatggatat tcgaacgcgt   11580
aggtaccaca tggttaacct agacttgtcc atcttctgga ttggccaact taattaatgt   11640
atgaaataaa aggatgcaca catagtgaca tgctaatcac tataatgtgg gcatcaaagt   11700
tgtgtgttat gtgtaattac tagttatctg aataaaagag aaagagatca tccatatttc   11760
ttatcctaaa tgaatgtcac gtgtctttat aattctttga tgaaccagat gcatttcatt   11820
aaccaaatcc atatacatat aaatattaat catatataat taatatcaat tgggttagca   11880
aaacaaatct agtctaggtg tgttttgcga atgcggccgc caccgcggtg gagctcgaat   11940
tcagtacatt aaaaacgtcc gcaatgtgtt attaagttgt ctaagcgtca atttgtgatg   12000
gagatcctgg tacactatct gtagcagttt ggaatggctt cccagatgac atcacactgg   12060
```

```
agtctctcag tttaaggttg tcagcttctt ctagtgcaga tgaaggtatc aaggtacaag  12120
tactgtgtta gcattactga ttgctaccct tttcctctgt ggcatgtctt attctgttat  12180
tcatggtttg gatgcactaa tatgttttca agtaaaattc agttccatcc ttgcagaaca  12240
gatttcataa atcaaaacta ctatgataaa gtatatcaaa ctctagagaa atgaccgcac  12300
ataacatatt cttcagtcac ctaatggttt aatgttgtca tccatgcagg caattaaaag  12360
ttcagattct catgttctag taccaggtag aaatatcatc tcttttgaca ttcctcgtca  12420
aaagcctggc tcctatgtgt tgggtgctct cactggacag attggcaagc tgtcattcag  12480
atcacatgga tttttcccaag atggtccagt tgaaactgat gaatttatga gctttgagaa  12540
accgacaaga cctgttttga aggtaattgc taaaatgagc tgaagattac ttagaagttt  12600
ttcgtggggc atgactggag ctagatccct tagaagtttc tggccttaag tttttttggg  12660 tttccccttaa agatttttt tttcttttc cccatttttc cataactggc accttgtatt  12720
gggtctattt taggccttc tttctcttct taatatattg atgtacagtt ctcctacagt  12780
tcgagaaaaa aagagctgac gatctgaact gttttataaa atcgtagccc taccccatgt  12840
cactaaactg ccataagaga tactatccat actttcaaaa caaaaccgga gcatagtttc  12900
ctctaattag tgaacatggt cagttatatt gtttaagaca gatatgttct cattgcattt  12960
gtttctctgt tgtaggtgag aaaaccaagg gctttagttg atattacacc tgctgtgtcc  13020
tctgctttgc ttatgaatga gctccaatgg attggattaa tcgttaagcc tatagactat  13080
tctttaaaag gtggaatatt gcatatcgat gctggcgctg aactgaaaat tgaggagtct  13140
cagatgattg aaatagaaat ttacgtaagt gatatggagt gtgctaattc tgccaacagc  13200
tccatcaaag ctggaaaggt tgaaaaggta cctattgaaa atggaaagat agaacttcct  13260
gattgggcta gtgatgtgac tactcttgtt tggtttcctg ttcgtgctat tgatgacaca  13320
attgcaagag gagaatccct aggtctgtat gtaacaagtg ataaattcac tatgttatgt  13380
ttcaatcagt tagttgacct ttctttgtcc ttgtttcagt gtctcagaaa cagagcgttg  13440
tagatgggat gagaatgatt gctctcaagc ttgagtttgg agttttccgt aaccaagtgt  13500
ttgaaaggta tctctctgtt tttcccctca aacatgcaga agagctgtgt catgtctgcc  13560
attgtataag aaaagatgag atacttcgat acattgaact ttagatatag atactcaaca  13620
aatttattat tatgattttc aggaccattg cagttcattt tactaaccca ttccatgtaa  13680
gcacacgcgt cgtggacaag tgcaatgatg gagctctact tctacaggta aagttctttc  13740
ttgtctggca catgattgtc attgttgtat tcctagattt aaaacacaca cacacacaca  13800
catatatata cagggatatt gggagccctg ctcttccaaa catatatact agaagcccca  13860
gccgtgccct gcaccacccg accggcttgg ccacctagat cccgtgcaca cgtccatccc  13920
ctgcatgcgg atatttgttt ccatttgcat gtgcgaaaaa tttggaaggt gtatctgttt  13980
cctgctgcat gcgcataa                                                 13998
```

<210> SEQ ID NO 2
<211> LENGTH: 26
<212> TYPE: DNA
<213> ORGANISM: Artificial Sequence
<220> FEATURE:
<223> OTHER INFORMATION: primer 08-0-2544

<400> SEQUENCE: 2
tcaagccgtg agcagacatg ttgcag                                          26

```
<210> SEQ ID NO 3
<211> LENGTH: 26
<212> TYPE: DNA
<213> ORGANISM: priArtificial Sequence
<220> FEATURE:
<223> OTHER INFORMATION: primer

<400> SEQUENCE: 3
cgaagaagag gtgagggtac tgcacg                                              26

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
ccgctgtatc acaagggctg gtacc                                               25

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
ggagcccgtg tagagcatga cgatc                                               25

<210> SEQ ID NO 6
<211> LENGTH: 24
<212> TYPE: DNA
<213> ORGANISM: pArtificial Sequence
<220> FEATURE:
<223> OTHER INFORMATION: primer

<400> SEQUENCE: 6
cgagacttca ctgccagttg atcg                                                24

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
acggcttgtc ccgcgtcatc                                                     20

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
ggtgcagctg acaattacca ccgatcttgg tg                                       32

<210> SEQ ID NO 9
<211> LENGTH: 23
<212> TYPE: DNA
<213> ORGANISM: Artificial Sequence
<220> FEATURE:
<223> OTHER INFORMATION: primer
```

```
<400> SEQUENCE: 9
cagacagtgt ccggtgcaga tcc                                              23

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tccgcgaccg cgaattgggc                                                  20

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
tcccgtccga gtactgcgtg tc                                               22

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
agcatcgatc acgacaccat ggcg                                             24

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
catgtggtac ctacgcgttc gaatatcca                                        29

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
caccgagcgc ctgtaccccc g                                                21

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
ttatgcgcat gcagcaggaa acagatacac c                                     31

<210> SEQ ID NO 16
```

```
<210> SEQ ID NO 16
<211> LENGTH: 29
<212> TYPE: DNA
<213> ORGANISM: Artificial Sequence
<220> FEATURE:
<223> OTHER INFORMATION: primer

<400> SEQUENCE: 16
ttcttgatgg agagatcgca gctctgttc                                  29

<210> SEQ ID NO 17
<211> LENGTH: 28
<212> TYPE: DNA
<213> ORGANISM: Artificial Sequence
<220> FEATURE:
<223> OTHER INFORMATION: primer

<400> SEQUENCE: 17
ccgctcatga tcagatttca ctgtgagc                                   28

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
ggagatcctg gtacactatc tgtagcagtt tgg                             33

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
ggtcatttct ctagagtttg atatacttta tcatag                          36

<210> SEQ ID NO 20
<211> LENGTH: 412
<212> TYPE: PRT
<213> ORGANISM: Zea mays

<400> SEQUENCE: 20

Met Glu Lys Arg Asn Leu Gln Trp Arg Arg Gly Arg Asp Gly Ile Val
 1               5                  10                  15

Gln Tyr Pro His Leu Phe Phe Ala Ala Leu Ala Leu Ala Leu Leu Val
                20                  25                  30

Ala Asp Pro Phe Gly Leu Ser Pro Leu Ala Glu Val Asp Tyr Arg Pro
            35                  40                  45

Val Lys His Glu Leu Ala Pro Tyr Gly Glu Val Met Gly Ser Trp Pro
        50                  55                  60

Arg Asp Asn Ala Ser Arg Leu Arg Arg Gly Arg Leu Glu Phe Val Gly
 65                  70                  75                  80

Glu Val Phe Gly Pro Glu Ser Ile Glu Phe Asp Leu Gln Gly Arg Gly
                 85                  90                  95

Pro Tyr Ala Gly Leu Ala Asp Gly Arg Val Val Arg Trp Met Gly Glu
            100                 105                 110

Glu Ala Gly Trp Glu Thr Phe Ala Val Met Asn Pro Asp Trp Ser Glu
        115                 120                 125

Glu Val Cys Ala Asn Gly Val Asn Ser Thr Thr Arg Lys Gln His Glu
```

```
            130                 135                 140
Lys Glu Glu Phe Cys Gly Arg Pro Leu Gly Leu Arg Phe His Gly Glu
145                 150                 155                 160

Thr Gly Glu Leu Tyr Val Ala Asp Ala Tyr Tyr Gly Leu Met Val Val
                165                 170                 175

Gly Gln Ser Gly Gly Val Ala Ser Ser Val Ala Arg Glu Ala Asp Gly
            180                 185                 190

Asp Pro Ile Arg Phe Ala Asn Asp Leu Asp Val His Arg Asn Gly Ser
                195                 200                 205

Val Phe Phe Thr Asp Thr Ser Met Arg Tyr Ser Arg Lys Asp His Leu
210                 215                 220

Asn Ile Leu Leu Glu Gly Gly Thr Gly Arg Leu Leu Arg Tyr Asp
225                 230                 235                 240

Pro Glu Thr Ser Gly Val His Val Val Leu Lys Gly Leu Val Phe Pro
                245                 250                 255

Asn Gly Val Gln Ile Ser Glu Asp His Gln Phe Leu Leu Phe Ser Glu
                260                 265                 270

Thr Thr Asn Cys Arg Ile Met Arg Tyr Trp Leu Glu Gly Pro Arg Ala
                275                 280                 285

Gly Glu Val Glu Val Phe Ala Asn Leu Pro Gly Phe Pro Asp Asn Val
                290                 295                 300

Arg Ser Asn Gly Arg Gly Gln Phe Trp Val Ala Ile Asp Cys Cys Arg
305                 310                 315                 320

Thr Pro Ala Gln Glu Val Phe Ala Lys Arg Pro Trp Leu Arg Thr Leu
                325                 330                 335

Tyr Phe Lys Phe Pro Leu Ser Leu Lys Val Leu Thr Trp Lys Ala Ala
                340                 345                 350

Arg Arg Met His Thr Val Leu Ala Leu Leu Asp Gly Glu Gly Arg Val
                355                 360                 365

Val Glu Val Leu Glu Asp Arg Gly His Glu Val Met Lys Leu Val Ser
                370                 375                 380

Glu Val Arg Glu Val Gly Arg Lys Leu Trp Ile Gly Thr Val Ala His
385                 390                 395                 400

Asn His Ile Ala Thr Ile Pro Tyr Pro Leu Glu Asp
                405                 410

<210> SEQ ID NO 21
<211> LENGTH: 495
<212> TYPE: PRT
<213> ORGANISM: Artificial Sequence
<220> FEATURE:
<223> OTHER INFORMATION: Zm-bt1 transit peptide plus Zm-aa1 region from
      PHP24597

<400> SEQUENCE: 21

Met Ala Ala Thr Met Ala Val Thr Thr Met Val Thr Arg Ser Lys Glu
1               5                   10                  15

Ser Trp Ser Ser Leu Gln Val Pro Ala Val Ala Phe Pro Trp Lys Pro
                20                  25                  30

Arg Gly Gly Lys Thr Gly Gly Leu Glu Phe Pro Arg Arg Ala Met Phe
            35                  40                  45

Ala Ser Val Gly Leu Asn Val Cys Pro Gly Val Pro Ala Gly Arg Asp
        50                  55                  60

Pro Arg Glu Pro Asp Pro Lys Val Val Arg Ala Ala Cys Gly Leu Val
65                  70                  75                  80
```

```
Gln Ala Gln Val Leu Phe Gln Gly Phe Asn Trp Glu Ser Cys Lys Gln
                85                  90                  95
Gln Gly Gly Trp Tyr Asn Arg Leu Lys Ala Gln Val Asp Asp Ile Ala
            100                 105                 110
Lys Ala Gly Val Thr His Val Trp Leu Pro Pro Ser His Ser Val
        115                 120                 125
Ser Pro Gln Gly Tyr Met Pro Gly Arg Leu Tyr Asp Leu Asp Ala Ser
    130                 135                 140
Lys Tyr Gly Thr Ala Ala Glu Leu Lys Ser Leu Ile Ala Ala Phe His
145                 150                 155                 160
Gly Arg Gly Val Gln Cys Val Ala Asp Ile Val Ile Asn His Arg Cys
                165                 170                 175
Ala Glu Lys Lys Asp Ala Arg Gly Val Tyr Cys Ile Phe Glu Gly Gly
            180                 185                 190
Thr Pro Asp Asp Arg Leu Asp Trp Gly Pro Gly Met Ile Cys Ser Asp
        195                 200                 205
Asp Thr Gln Tyr Ser Asp Gly Thr Gly His Arg Asp Thr Gly Glu Gly
    210                 215                 220
Phe Ala Ala Ala Pro Asp Ile Asp His Leu Asn Pro Arg Val Gln Arg
225                 230                 235                 240
Glu Leu Ser Ala Trp Leu Asn Trp Leu Arg Ser Asp Ala Val Gly Phe
                245                 250                 255
Asp Gly Trp Arg Leu Asp Phe Ala Lys Gly Tyr Ser Pro Ala Val Ala
            260                 265                 270
Arg Met Tyr Val Glu Ser Thr Gly Pro Pro Ser Phe Val Val Ala Glu
        275                 280                 285
Ile Trp Asn Ser Leu Ser Tyr Ser Gly Asp Gly Lys Pro Ala Pro Asn
    290                 295                 300
Gln Asp Gln Cys Arg Gln Glu Leu Leu Asp Trp Thr Arg Ala Val Gly
305                 310                 315                 320
Gly Pro Ala Met Ala Phe Asp Phe Pro Thr Lys Gly Leu Leu Gln Ala
                325                 330                 335
Gly Val Gln Gly Glu Leu Trp Arg Leu Arg Asp Ser Ser Gly Asn Ala
            340                 345                 350
Ala Gly Leu Ile Gly Trp Ala Pro Glu Lys Ala Val Thr Phe Val Asp
        355                 360                 365
Asn His Asp Thr Gly Ser Thr Gln Lys Leu Trp Pro Phe Pro Ser Asp
    370                 375                 380
Lys Val Met Gln Gly Tyr Ala Tyr Ile Leu Thr His Pro Gly Val Pro
385                 390                 395                 400
Cys Ile Phe Tyr Asp His Met Phe Asp Trp Asn Leu Lys Gln Glu Ile
                405                 410                 415
Ser Thr Leu Ser Ala Ile Arg Ala Arg Asn Gly Ile Arg Ala Gly Ser
            420                 425                 430
Lys Leu Arg Ile Leu Val Ala Asp Ala Asp Ala Tyr Val Ala Val Val
        435                 440                 445
Asp Glu Lys Val Met Val Lys Ile Gly Thr Arg Tyr Gly Val Ser Ser
    450                 455                 460
Val Val Pro Ser Asp Phe His Pro Ala Ala His Gly Lys Asp Tyr Cys
465                 470                 475                 480
Val Trp Glu Lys Ala Ser Leu Arg Val Pro Ala Gly Arg His Leu
                485                 490                 495
```

```
<210> SEQ ID NO 22
<211> LENGTH: 28
<212> TYPE: DNA
<213> ORGANISM: Artificial Sequence
<220> FEATURE:
<223> OTHER INFORMATION: forward primer DP-32138-1_3_193F for PCR
      detection system

<400> SEQUENCE: 22
tccgcaatgt gttattaagt tgtctaag                                          28

<210> SEQ ID NO 23
<211> LENGTH: 23
<212> TYPE: DNA
<213> ORGANISM: Artificial Sequence
<220> FEATURE:
<223> OTHER INFORMATION: reverse primer DP-32138-1_3_289R for PCR
      detection system

<400> SEQUENCE: 23
tgatgtcatc tgggaagcca ttc                                               23

<210> SEQ ID NO 24
<211> LENGTH: 28
<212> TYPE: DNA
<213> ORGANISM: Artificial Sequence
<220> FEATURE:
<223> OTHER INFORMATION: probe DP-32138-1_3_221T:FAM:TAM for PCR
      detection system

<400> SEQUENCE: 24
cgtcaatttg tgatggagat cctggtac                                          28

<210> SEQ ID NO 25
<211> LENGTH: 97
<212> TYPE: DNA
<213> ORGANISM: Artificial Sequence
<220> FEATURE:
<223> OTHER INFORMATION: amplicon

<400> SEQUENCE: 25
tccgcaatgt gttattaagt tgtctaagcg tcaatttgtg atggagatcc tggtacacta       60
tctgtagcag tttggaatgg cttcccagat gacatca                                97

<210> SEQ ID NO 26
<211> LENGTH: 22
<212> TYPE: DNA
<213> ORGANISM: Artificial Sequence
<220> FEATURE:
<223> OTHER INFORMATION: forward primer DP-32138-1-3-F2 for gel-based
      detection system

<400> SEQUENCE: 26
gtggagctcg aattcagtac at                                                22

<210> SEQ ID NO 27
<211> LENGTH: 26
<212> TYPE: DNA
<213> ORGANISM: Artificial Sequence
<220> FEATURE:
<223> OTHER INFORMATION: reverse primer DP-32138-1_3_273R for gel-based
      detection system

<400> SEQUENCE: 27
gccattccaa actgctacag atagtg                                            26
```

```
<210> SEQ ID NO 28
<211> LENGTH: 111
<212> TYPE: DNA
<213> ORGANISM: Artificial Sequence
<220> FEATURE:
<223> OTHER INFORMATION: amplicon

<400> SEQUENCE: 28
gtggagctcg aattcagtac attaaaaacg tccgcaatgt gttattaagt tgtctaagcg      60
tcaatttgtg atggagatcc tggtacacta tctgtagcag tttggaatgg c             111

<210> SEQ ID NO 29
<211> LENGTH: 27
<212> TYPE: DNA
<213> ORGANISM: Artificial Sequence
<220> FEATURE:
<223> OTHER INFORMATION: forward primer 07-O-2134

<400> SEQUENCE: 29
cgcaatgtgt tattaagttg tctaagc                                         27

<210> SEQ ID NO 30
<211> LENGTH: 24
<212> TYPE: DNA
<213> ORGANISM: Artificial Sequence
<220> FEATURE:
<223> OTHER INFORMATION: reverse primer 07-O-2135

<400> SEQUENCE: 30
agccattcca aactgctaca gata                                            24

<210> SEQ ID NO 31
<211> LENGTH: 19
<212> TYPE: DNA
<213> ORGANISM: Artificial Sequence
<220> FEATURE:
<223> OTHER INFORMATION: probe 07-QP63 (FAM-MGB) for real-time PCR

<400> SEQUENCE: 31
caatttgtga tggagatcc                                                  19

<210> SEQ ID NO 32
<211> LENGTH: 80
<212> TYPE: DNA
<213> ORGANISM: Artificial Sequence
<220> FEATURE:
<223> OTHER INFORMATION: amplicon

<400> SEQUENCE: 32
cgcaatgtgt tattaagttg tctaagcgtc aatttgtgat ggagatcctg gtacactatc     60
tgtagcagtt tggaatggct                                                 80

<210> SEQ ID NO 33
<211> LENGTH: 225
<212> TYPE: PRT
<213> ORGANISM: Discosoma sp.

<400> SEQUENCE: 33

Met Ala Ser Ser Glu Asn Val Ile Thr Glu Phe Met Arg Phe Lys Val
  1               5                  10                  15

Arg Met Glu Gly Thr Val Asn Gly His Glu Phe Glu Ile Glu Gly Glu
             20                  25                  30

Gly Glu Gly Arg Pro Tyr Glu Gly His Asn Thr Val Lys Leu Lys Val
         35                  40                  45
```

Thr Lys Gly Gly Pro Leu Pro Phe Ala Trp Asp Ile Leu Ser Pro Gln
 50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Ala Thr Val Thr Gln Asp Ser Ser
                100                 105                 110

Leu Gln Asp Gly Cys Phe Ile Tyr Lys Val Lys Phe Ile Gly Val Asn
            115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
                180                 185                 190

Tyr Tyr Val Asp Ala Lys Leu Asp Ile Thr Ser His Asn Glu Asp Tyr
                195                 200                 205

Thr Ile Val Glu Gln Tyr Glu Arg Thr Glu Gly Arg His His Leu Phe
210                 215                 220

Leu
225

<210> SEQ ID NO 34
<211> LENGTH: 9950
<212> TYPE: DNA
<213> ORGANISM: Artificial Sequence
<220> FEATURE:
<223> OTHER INFORMATION: T-DNA of PHP24597
<220> FEATURE:
<221> NAME/KEY: misc_feature
<222> LOCATION: (1)...(25)
<223> OTHER INFORMATION: right border repeat
<220> FEATURE:
<221> NAME/KEY: misc_feature
<222> LOCATION: (9926)...(9950)
<223> OTHER INFORMATION: left border repeat

<400> SEQUENCE: 34
gtttacccgc caatatatcc tgtcaaacac tgatagttta aactgaaggc gggaaacgac     60
aatctgatca tgagcggaga attaagggag tcacgttatg accccgccg atgacgcggg    120 acaagccgtt ttacgtttgg aactgacaga accgcaacgt tgaaggagcc actcagcaag    180
cttgatatcg aattcctgca gcccctatgat ttagaataat atacaaatat attacataaa    240
aaatatatta attgaattag tgttgtctaa tttataatta ttagaatgta attcaattcc    300
aacgaaacaa cggggcctta ggtttaatat cttccttaca ctgcgaaaat gttgttacac    360
ttgccaaaaa aaatcaatcg catatttacc ttacaaggac atattttagc aaaatgctat    420
agacatgaat ccaacgtaat caatagagtg agatttactg gtaaactacc aattgctcat    480
ctgctcggta ccaaccagcc tttcctatta ccatgcacat gttgcctctc aactgcagca    540 tcttcaagc cgtgagcaga catgttgcag atcgaagtaa ggtatatatg tgcatagtct    600
cctaattctt catcttcaac ctctagctga ttgatctctg gtatttacca ctcttttcctt    660 ccttccttcc ttcaattcta aataccacaa atcaaagttg ctttgccatg gagaagagga    720

```
acctgcagtg gcggcgaggg cgtgatggca tcgtgcagta ccctcacctc ttcttcgcgg    780
ccctggcgct ggccctccta gtcgcggacc cgttcggcct cagtccgctg gccgaggtcg    840
actaccggcc ggtgaagcac gagctcgcgc cgtacgggga ggtcatgggc agctggccca    900
gagacaatgc cagccggctc aggcgcggga ggctggagtt cgtcggcgag gtgttcgggc    960
cggagtctat cgagttcgat ctccagggcc gcggccgta cgccggcctc gccgacggcc   1020
gcgtcgtgcg gtggatgggc gaggaggccg ggtgggagac gttcgccgtc atgaatcctg   1080
actggtaagt gctcgatatc gctccggcgt ccactcgtta catgctataa tatagtagta   1140
ctaagatatt ttgatctgat tttttgcatt cttgggagaa acgtcatgca aaatttgttg   1200
tttcttggca aaggtcagaa gaagtctgtg ccaatggagt gaactcaacg acgaggaagc   1260
agcacgagaa ggaggagttc tgcggccggc cgctcggcct gaggttccac ggggagaccg   1320
gcgagctcta cgtcgccgac gcgtactacg gtctcatggt cgttggccag agcggcggcg   1380
tggcgtcctc cgtcgcgagg gaagccgacg gggaccccat ccggttcgcg aacgacctcg   1440
atgtgcacag gaatggatcc gtattcttca ctgacacgag catgagatac agcagaaagt   1500
gagcaaagcg acgtaacaat ccggcttctc attttcaaac gcctctgtat tctctgctga   1560
aagagtagct caccagacaa gagctgaatt tgcaggacc atctgaacat cctgttagaa   1620
ggagaaggca ccgggaggct gctcaggtat gatccagaaa caagcggtgt ccatgtcgtg   1680
ctcaaggggc tggtgttccc aaacggcgtg cagatctcag aggaccatca gtttcttctc   1740
ttctccgaga caacaaactg caggtaacaa aaatactatc tgacgatgct catgattcta   1800
ccgtatccat agtcatgaac acaaaccaca cgaatcggc cttgaccagg ataatgaggt   1860
actggctgga aggcccaaga gcgggcgagg tagaggtgtt cgcgaacctg ccgggcttcc   1920
ccgacaacgt gcgctccaac ggcaggggcc agttctgggt ggcgatcgac tgctgccgga   1980
cgccggcgca ggaggtgttc gccaagaggc cgtggctccg gaccctgtac ttcaagttcc   2040
cgctgtcgct caaggtgctc acttggaagg ccgccaggag gatgcacacg gtgctcgcgc   2100
tcctcgacgg cgaagggcgc gtcgtggagg tgctcgagga ccggggccac gaggtgatga   2160
agctggtgag cgaggtgcgg gaggtgggcc gcaagctgtg gatcggaacc gtggcgcaca   2220
accacatcgc caccatcccc tacccttttag aggactaacc atgatctatg ctgtttcaat   2280
gcctcctaat ctgtgtacgt ctataaatgt ctaatgcagt cactggttgt aatcttgttt   2340
gtgtttggca aattggcata ataatggaca gattcaatgg gcattggtgc tgtagtcgca   2400
tcacactaat tgaatgggat catgttgagc tctcactttg ctacaatttg ctccagcttg   2460
tacggttgta ccctcttgct cgtctatagt aagggccatc taaaaaaaac tcaaattaga   2520
tctgcaatac aagtatgatt gggccgaatt tggattgtca cgggtccgcg accgcgaatt   2580
gggctcggtt tgatttagcc gacatagtag tgaccgaccc gagccggcgg cgagccaaac   2640
cgagcggacg ccgccatgat caagctatcg gacggccgct ctagaactag tggatcagct   2700
tgcatgcctg caggtcgact ctagaggatc tgcaccggac actgtctggt ggcataccag   2760
acagtccggt gtgccagatc agggcaccct tcggttcctt tgctcctttg cttttgaacc   2820
ctaactttga tcgtttattg gtttgtgttg aaccttatg cacctgtgga atatataatc   2880
tagaacaaac tagttagtcc aatcatttgt gttgggcatt caaccaccaa aattatttat   2940
aggaaaaggt taaaccttat ttcccttttca atctcccct ttttggtgat tgatgccaac   3000
acaaaccaaa gaaaatatat aagtgcagaa ttgaactagt ttgcataagg taagtgcata   3060
ggttacttag aattaaatca atttatactt ttacttgata tgcatggttg ctttctttta   3120
```

-continued

```
ttttaacatt ttggaccaca tttgcaccac ttgttttgtt ttttgcaaat cttttttggaa    3180 attcttttc  aaagtctttt gcaaatagtc aaaggtatat gaataagatt gtaagaagca    3240
ttttcaagat ttgaaatttc tcccctgtt  tcaaatgctt ttcctttgac taaacaaaac    3300
tccccctgaa taaaattctc ctcttagctt tcaagagggt tttaaataga tatcaattgg    3360
aaatatattt agatgctaat tttgaaaata taccaattga aaatcaacat accaatttga    3420
aattaaacat accaatttaa aaaatttcaa aaagtggtgg tgcggtcctt ttgctttggg    3480
cttaatattt ctcccccttt ggcattaatc gccaaaaacg gagactttgt gagccattta    3540
tactttctcc ccattggtaa atgaaatatg agtgaaagat tataccaaat ttggacagtg    3600
atgcggagtg acggcgaagg ataaacgata ccgttagagt ggagtggaag ccttgtcttc    3660
gccgaagact ccatttccct ttcaatctac gacttagcat agaaatacac ttgaaaacac    3720
attagtcgta gccacgaaag agatatgatc aaaggtatac aaatgagcta tgtgtgtaat    3780
gtttcaatca aagtttcgag aatcaagaat atttagctca ttcctaagtt tgctaaaggt    3840
tttatcatct aatggtttgg taaagatatc gactaattgt tctttggtgc taacataagc    3900
aatctcgata tcacccettt gttggtgatc cctcaaaaag tgataccgaa tgtctatgtg    3960
cttagtgcgg ctgtgttcaa cgggattatc cgccatgcag atagcactct cattgtcaca    4020
taggagaggg actttgctca atttgtagcc atagtcccta aggttttgcc tcatccaaag    4080
taattgcaca caacaatgtc ctgcggcaat atacttggct tcggcggtag aaagagctat    4140
tgagttttgt ttcttttgaag tccaagacac caggggatctc cctagaaact gacaagtccc    4200
tgatgtgctc ttcctatcaa ttttacaccc tgcccaatcg gcatctgaat atcctattaa    4260
atcaaaggtg gatcccttgg ggtaccaaag accaaattta ggagtgtaaa ctaaatatct    4320
catgattctt ttcacggccc taaggtgaac ttccttagga tcggcttgga atcttgcaca    4380
catgcatata gaaagcatac tatctggtcg agatgcacat aaatagagta aagatcctat    4440
catcgaccgg tataccttt  ggtctacgga tttacctccc gtgtcgaggt cgagatgccc    4500
attagttccc atgggtgtcc tgatgggctt ggcatccttc attccaaact tgttgagtat    4560
gtcttgaatg tactttgttt ggctgatgaa ggtgccatct tggagttgct tgacttgaaa    4620
tcctagaaaa tatttcaact tccccatcat agacatctcg aatttcggaa tcatgatcct    4680
actaaactct tcacaagtag atttgttagt agacccaaat ataatatcat caacataaat    4740
ttggcataca aacaaaactt tgaaatggt  tttagtaaag agagtaggat cggctttact    4800
gactctgaag ccattagtga taagaaaatc tcttaggcat tcataccatg ctgttggggc    4860
ttgcttgagc ccataaagcg cctttgagag tttataaaca tggttagggt actcactatc    4920
ttcaaagccg agaggttgct caacatagac ctattcaccc catttgatca ctttttttggt    4980 ccttcaggat ctaatagtta tgtataattt agagtctctt gtttaatggc cagatatttc    5040
taattaatct aagaatttat gatatttttt aattttttat catgtctgat gagaattaac    5100
ataaaggctc aattgggtcc tgaattaata atagagtgaa aattaatcca gaggctctat    5160
tagaaccttc aattagtaat accaagatat atataagata gtagagtata gtttaaatgt    5220
tggcattgtt cattctttct tttgttattt aatttatgct ttccacggtg gttagtggtt    5280
acttctgaag ggtccaaata atgcatgaag agtttgagga caagaagtct gccctaaaaa    5340
tagcgatgca aaggcatggt gtccaagcca tacatatagc gcactaattt tatcagcaga    5400
acaatggtat ttataggtcc tagtgcccag gcaacaagag acacgaataa agcatcgatc    5460
```

```
acgacaccat ggcggcgaca atggcagtga cgacgatggt gacgaggagc aaggagagct    5520
ggtcgtcatt gcaggtcccg gcggtggcat tcccttggaa gccacgaggt ggcaagaccg    5580
gcggcctcga gttccctcgc cgggcgatgt tcgccagcgt cggcctcaac gtgtgcccgg    5640
gcgtcccggc ggggcgcgac ccgcgggagc ccgatcccaa ggtcgtccgg gcggcctgcg    5700
gcctggtcca ggcacaagtc ctcttccagg ggtttaactg ggagtcgtgc aagcagcagg    5760
gaggctggta caacaggctc aaggcccagg tcgacgacat cgccaaggcc ggcgtcacgc    5820
acgtctggct gcctccaccc tcgcactccg tctcgccaca aggctacatg ccaggccgcc    5880
tatacgacct ggacgcgtcc aagtacggca cggcggcgga gctcaagtcc ctgatagcgg    5940
cgttccacgg caggggcgtg cagtgcgtgg cggacatcgt catcaaccac cggtgcgcgg    6000
aaaagaagga cgcgcgcggc gtgtactgca tcttcgaggg cgggactccc gacgaccgcc    6060
tggactgggg ccccgggatg atctgcagcg acgacacgca gtactcggac gggacggggc    6120
accgcgacac gggcgagggg ttcgcggcg cgcccgacat cgaccacctc aacccgcgcg    6180
tgcagcggga gctctccgcc tggctcaact ggctcaggtc cgacgccgtg gggttcgacg    6240
gctggcgcct cgacttcgcc aagggctact cgccggccgt cgccagaatg tacgtggaga    6300
gcacggggcc gccgagcttc gtcgtcgcgg agatatggaa ctcgctgagc tacagcgggg    6360
acggcaagcc ggcgcccaac caggaccagt gccggcagga gctgctggac tggacgcggg    6420
ccgtcggcgg gcccgccatg gcgttcgact cccccaccaa gggcctgctg caggcgggcg    6480
tgcaggggga gctgtggcgg ctgcgcgaca gctccggcaa gcgggccggc ctgatcgggt    6540
gggcgcccga gaaggccgtc accttcgtcg acaaccatga caccgggtcg acgcagaagc    6600
tctggccgtt cccatccgac aaggtcatgc agggctacgc ctacatcctc acccatccag    6660
gagtcccctg catttttctac gaccacatgt tcgactggaa cctgaagcag gagatatcca    6720
cgctgtctgc catcagggcg cggaacggca tccgcgccgg gagcaagctg cggatcctcg    6780
tggcggacgc ggacgcgtac gtggccgtcg tcgacgagaa ggtcatggtg aagatcggga    6840
caaggtacgg cgtgagcagc gtggtcccgt cggatttcca cccggcggcg cacggcaagg    6900
actactgcgt ctgggagaaa gcgagcctcc gcgtcccggc ggggcgccac ctctagcagc    6960
tcagattgct cagtcttgtg ctgcattgca aacacagcag cacgacactg cataacgtct    7020
tttccttgag atctgacaaa gcagcattag tccgttgatc ggtggaagac cactcgtcag    7080
tgttgagttg aatgtttgat caataaaata cggcaatgct gtaagggttg ttttttatgc    7140
cattgataat acactgtact gttcagttgt tgaactctat ttcttagcca tgccaagtgc    7200
ttttcttatt ttgaataaca ttacagcaaa aagttgaaag acaaaaaaaa aaaccccga    7260
acagagtgct ttgggtccca agctacttta gactgtgttc ggcgttcccc ctaaatttct    7320
ccccctatat ctcactcact tgtcacatca gcgttctctt tccctatat ctccacgtcg    7380
acgcggccga tccccggc tgcaggaatt cccatggagt caaagattca aatagaggac    7440
ctaacagaac tcgccgtaaa gactggcgaa cagttcatac agagtctctt acgactcaat    7500
gacaagaaga aaatcttcgt caacatggtg gagcacgaca cgcttgtcta ctccaaaaat    7560
atcaaagata cagtctcaga agaccaaagg gcaattgaga cttttcaaca aagggtaata    7620
tccggaaacc tcctcggatt ccattgccca gctatctgtc actttattgt gaagatagtg    7680
gaaaggaag gtggctccta caaatgccat cattgcgata aaggaaaggc catcgttgaa    7740
gatgcctctg ccgacagtgg tcccaaagat ggacccccac ccacgaggag catcgtggaa    7800
aaagaagacg ttccaaccac gtcttcaaag caagtggatt gatgtgatat ctccactgac    7860
```

```
gtaagggatg acgcacaatc ccactaagct gaccgaagct ggccgctcta gaactagtgg    7920
atctcgatgt gtagtctacg agaagggtta accgtctctt cgtgagaata accgtggcct    7980
aaaaataagc cgatgaggat aaataaaatg tggtggtaca gtacttcaag aggtttactc    8040
atcaagagga tgcttttccg atgagctcta gtagtacatc ggacctcaca tacctccatt    8100
gtggtgaaat attttgtgct catttagtga tgggtaaatt ttgtttatgt cactctaggt    8160
tttgacattt cagttttgcc actcttaggt tttgacaaat aatttccatt ccgcggcaaa    8220
agcaaaacaa ttttatttta cttttaccac tcttagcttt cacaatgtat cacaaatgcc    8280
actctagaaa ttctgtttat gccacagaat gtgaaaaaaa acactcactt atttgaagcc    8340
aaggtgttca tggcatggaa atgtgacata agtaacgtt cgtgtataag aaaaaattgt     8400
actcctcgta acaagagacg gaaacatcat gagacaatcg cgtttggaag gctttgcatc    8460
acctttggat gatgcgcatg aatggagtcg tctgcttgct agccttcgcc taccgcccac    8520
tgagtccggg cggcaactac catcggcgaa cgacccagct gacctctacc gaccggactt    8580
gaatgcgcta ccttcgtcag cgacgatggc cgcgtacgct ggcgacgtgc ccccgcatgc    8640
atggcggcac atggcgagct cagaccgtgc gtggctggca caaatacgt accccgtgag    8700 tgccctagct agaaacttac acctgcaact gcgagagcga gcgtgtgagt gtagccgagt    8760 agatccccg gctgcaggt cgactctaga ggatccaccg gtcgccacca tggcctcctc      8820
cgagaacgtc atcaccgagt tcatgcgctt caaggtgcgc atggagggca ccgtgaacgg    8880
ccacgagttc gagatcgagg cgagggcga gggccgcccc tacgagggcc acaacaccgt    8940
gaagctgaag gtgacgaagg gcggcccct gcccttcgcc tgggacatcc tgtcccccca     9000
gttccagtac ggctccaagg tgtacgtgaa gcaccccgcc gacatccccg actacaagaa    9060
gctgtccttc cccgagggct tcaagtggga gcgcgtgatg aacttcgagg acggcggcgt    9120
ggcgaccgtg acccaggact cctccctgca ggacggctgc ttcatctaca aggtgaagtt    9180
catcggcgtg aacttcccct ccgacggccc cgtgatgcag aagaagacca tgggctggga    9240
ggcctccacc gagcgcctgt accccgcga cggcgtgctg aagggcgaga cccacaaggc    9300
cctgaagctg aaggacggcg gccactacct ggtggagttc aagtccatct acatggccaa    9360
gaagcccgtg cagctgcccg gctactacta cgtggacgcc aagctggaca tcacctccca    9420
caacgaggac tacaccatcg tggagcagta cgagcgcacc gagggccgcc accacctgtt    9480
cctgtagcgg cccatggata ttcgaacgcg taggtaccac atggttaacc tagacttgtc    9540
catcttctgg attggccaac ttaattaatg tatgaaataa aaggatgcac acatagtgac    9600
atgctaatca ctataatgtg ggcatcaaag ttgtgtgtta tgtgtaatta ctagttatct    9660
gaataaaaga gaaagagatc atccatattt cttatcctaa atgaatgtca cgtgtctta    9720 taattctttg atgaaccaga tgcatttcat taaccaaatc catatacata taaatattaa    9780
tcatatataa ttaatatcaa ttgggttagc aaaacaaatc tagtctaggt gtgttttgcg    9840
aatgcggccg ccaccgcggt ggagctcgaa ttcagtacat taaaaacgtc cgcaatgtgt    9900
tattaagttg tctaagcgtc aatttgttta caccacaata tatcctgcca                9950
```

<210> SEQ ID NO 35  
<211> LENGTH: 685  
<212> TYPE: DNA  
<213> ORGANISM: Discosoma sp.  
<220> FEATURE:  
<221> NAME/KEY: CDS  
<222> LOCATION: (8)...(685)

<400> SEQUENCE: 35

```
cgccacc atg gcc tcc tcc gag aac gtc atc acc gag ttc atg cgc ttc        49
        Met Ala Ser Ser Glu Asn Val Ile Thr Glu Phe Met Arg Phe
        1               5                   10 aag gtg cgc atg gag ggc acc gtg aac ggc cac gag ttc gag atc gag        97
Lys Val Arg Met Glu Gly Thr Val Asn Gly His Glu Phe Glu Ile Glu
15                  20                  25                  30 ggc gag ggc gag ggc cgc ccc tac gag ggc cac aac acc gtg aag ctg       145
Gly Glu Gly Glu Gly Arg Pro Tyr Glu Gly His Asn Thr Val Lys Leu
                35                  40                  45 aag gtg acg aag ggc ggc ccc ctg ccc ttc gcc tgg gac atc ctg tcc       193
Lys Val Thr Lys Gly Gly Pro Leu Pro Phe Ala Trp Asp Ile Leu Ser
            50                  55                  60 ccc cag ttc cag tac ggc tcc aag gtg tac gtg aag cac ccc gcc gac       241
Pro Gln Phe Gln Tyr Gly Ser Lys Val Tyr Val Lys His Pro Ala Asp
        65                  70                  75 atc ccc gac tac aag aag ctg tcc ttc ccc gag ggc ttc aag tgg gag       289
Ile Pro Asp Tyr Lys Lys Leu Ser Phe Pro Glu Gly Phe Lys Trp Glu
    80                  85                  90 cgc gtg atg aac ttc gag gac ggc ggc gtg gcg acc gtg acc cag gac       337
Arg Val Met Asn Phe Glu Asp Gly Gly Val Ala Thr Val Thr Gln Asp
95                  100                 105                 110 tcc tcc ctg cag gac ggc tgc ttc atc tac aag gtg aag ttc atc ggc       385
Ser Ser Leu Gln Asp Gly Cys Phe Ile Tyr Lys Val Lys Phe Ile Gly
                115                 120                 125 gtg aac ttc ccc tcc gac ggc ccc gtg atg cag aag aag acc atg ggc       433
Val Asn Phe Pro Ser Asp Gly Pro Val Met Gln Lys Lys Thr Met Gly
            130                 135                 140 tgg gag gcc tcc acc gag cgc ctg tac ccc cgc gac ggc gtg ctg aag       481
Trp Glu Ala Ser Thr Glu Arg Leu Tyr Pro Arg Asp Gly Val Leu Lys
        145                 150                 155 ggc gag acc cac aag gcc ctg aag ctg aag gac ggc ggc cac tac ctg       529
Gly Glu Thr His Lys Ala Leu Lys Leu Lys Asp Gly Gly His Tyr Leu
    160                 165                 170 gtg gag ttc aag tcc atc tac atg gcc aag aag ccc gtg cag ctg ccc       577
Val Glu Phe Lys Ser Ile Tyr Met Ala Lys Lys Pro Val Gln Leu Pro
175                 180                 185                 190 ggc tac tac tac gtg gac gcc aag ctg gac atc acc tcc cac aac gag       625
Gly Tyr Tyr Tyr Val Asp Ala Lys Leu Asp Ile Thr Ser His Asn Glu
                195                 200                 205 gac tac acc atc gtg gag cag tac gag cgc acc gag ggc cgc cac cac       673
Asp Tyr Thr Ile Val Glu Gln Tyr Glu Arg Thr Glu Gly Arg His His
            210                 215                 220 ctg ttc ctg tag                                                       685
Leu Phe Leu *
        225
```

<210> SEQ ID NO 36
<211> LENGTH: 1340
<212> TYPE: DNA
<213> ORGANISM: Artificial Sequence
<220> FEATURE:
<223> OTHER INFORMATION: partial insert and border of 32138
<220> FEATURE:
<221> NAME/KEY: misc_feature
<222> LOCATION: (1)...(654)
<223> OTHER INFORMATION: partial insert
<220> FEATURE:
<221> NAME/KEY: misc_feature
<222> LOCATION: (655)...(1340)
<223> OTHER INFORMATION: left border flanking sequence

<400> SEQUENCE: 36

```
cgtgctgaag ggcgagaccc acaaggccct gaagctgaag gacggcggcc actacctggt      60
ggagttcaag tccatctaca tggccaagaa gcccgtgcag ctgcccggct actactacgt     120
ggacgccaag ctggacatca cctcccacaa cgaggactac accatcgtgg agcagtacga     180
gcgcaccgag ggccgccacc acctgttcct gtagcggccc atggatattc gaacgcgtag     240
gtaccacatg gttaacctag acttgtccat cttctggatt ggccaactta attaatgtat     300
gaaataaaag gatgcacaca tagtgacatg ctaatcacta taatgtgggc atcaaagttg     360
tgtgttatgt gtaattacta gttatctgaa taaaagagaa agagatcatc catatttctt     420
atcctaaatg aatgtcacgt gtcttttataa ttctttgatg aaccagatgc atttcattaa     480
ccaaatccat atacatataa atattaatca tatataatta atatcaattg ggttagcaaa     540
acaaatctag tctaggtgtg ttttgcgaat gcggccgcca ccgcggtgga gctcgaattc     600
agtacattaa aaacgtccgc aatgtgttat taagttgtct aagcgtcaat ttgtgatgga     660
gatcctggta cactatctgt agcagtttgg aatggcttcc cagatgacat cacactggag     720
tctctcagtt taaggttgtc agcttcttct agtgcagatg aaggtatcaa ggtacaagta     780
ctgtgttagc attactgatt gctacccttt tcctctgtgg catgtcttat tctgttattc     840
atggtttgga tgcactaata tgttttcaag taaaattcag ttccatcctt gcagaacaga     900
tttcataaat caaaactact atgataaagt atatcaaact ctagagaaat gaccgcacat     960
aacatattct tcagtcacct aatggtttaa tgttgtcatc catgcaggca attaaaagtt    1020
cagattctca tgttctagta ccaggtagaa atatcatctc ttttgacatt cctcgtcaaa    1080
agcctggctc ctatgtgttg ggtgctctca ctggacagat tggcaagctg tcattcagat    1140
cacatggatt ttcccaagat ggtccagttg aaactgatga atttatgagc tttgagaaac    1200
cgacaagacc tgttttgaag gtaattgcta aaatgagctg aagattactt agaagttttt    1260
cgtggggcat gactggagct agatccctta gaagtttctg gccttaagtt ttttgggtt     1320
tccccttaag attttttttt                                                 1340
```

<210> SEQ ID NO 37
<211> LENGTH: 1700
<212> TYPE: DNA
<213> ORGANISM: Artificial Sequence
<220> FEATURE:
<223> OTHER INFORMATION: partial insert and border of 32138
<220> FEATURE:
<221> NAME/KEY: misc_feature
<222> LOCATION: (1)...(843)
<223> OTHER INFORMATION: right border flanking sequence
<220> FEATURE:
<221> NAME/KEY: misc_feature
<222> LOCATION: (844)...(1700)
<223> OTHER INFORMATION: partial 32138 insert

<400> SEQUENCE: 37

```
cgccccggat cgatgccgct gccatcgcct gggcatggac accagtgcgc cgtgcatccg      60
gtcctgagac tgaattttgg acccccagaca aggaagcagc catgggcacc gtcctggtgg    120
cgcctgagcc gccgcagcga cagcatacga cagatcccata ccaagggcca tcggacccac    180
actcaaggat ggcagaatcc attccgctgg cgctagagcc aatgatggca atgtcccggc    240
aggccggcat agctgcgctt gcgtgctctc atcgtgaccc ccagcctttg gtggcatgct    300
ccggcggtgg cgagggggag gggtagggag gaggctcaac ggtgcgtgcg atgggcttcg    360
ctctaaccgt ctaggcaggc aacgcagggg ttgggggggg aattgcgatg ctcatcacaa    420
```

-continued

```
tatatacaca ttatggactt taattttcgt aataatgctt ctgtgttttc tttgaactat    480
ttttgtgtta cagaaaagat atatggagct tactaaaggt gcagctgaca attaccaccg    540
atcttggtgg aaaagacatg gagttgttct tgatggagag atcgcagctc tgttctttaa    600
gcatggaaat tatgacctgg ctgtgaaatc ctatgagaaa gtttgtgctc tctattctgc    660
agaaggctgg gaagagctgt tggcagatgt tcttcctgat cttgcagaat gccagaagat    720
tcttaatgat gaagctggtt atttggcttc ttgtgtaaag ttactatcgc tggacagtgg    780
cttgttttca tctaaagagc ggcaaggttt ccagtcagaa gttgttcgac ttgctcacag    840
tgaaatctga tcatgagcgg agaattaagg cgggaaacga caatctgatc atgagcggag    900
aattaaggga gtcacgttat gacccccgcc gatgacgcgg gacaagccgt tttacgtttg    960
gaactgacag aaccgcaacg ttgaaggagc cactcagccc aagcttgata tcgaattcct   1020
gcagccctat gatttagaat aatatacaaa tatattacat aaaaaatata ttaattgaat   1080
tagtgttgtc taatttataa ttattagaat gtaattcaat tccaacgaaa caacggggcc   1140
ttaggtttaa tatcttcctt acactgcgaa aatgttgtta cacttgccaa aaaaaatcaa   1200
tcgcatattt accttacaag gacatatttt agcaaaatgc tatagacatg aatccaacgt   1260
aatcaataga gtgagattta ctggtaaact accaattgct catctgctcg gtaccaacca   1320
gcctttccta ttaccatgca catgttgcct ctcaactgca gcatctttca agccgtgagc   1380
agacatgttg cagatcgaag taaggtatat atgtgcatag tctcctaatt cttcatcttc   1440
aacctctagc tgattgatct ctggtattta ccactctttc cttccttcct tccttcaatt   1500
ctaaatacca caaatcaaag ttgctttgcc atggagaaga ggaacctgca gtggcggcga   1560
gggcgtgatg gcatcgtgca gtaccctcac ctcttcttcg cggccctggc gctggccctc   1620
ctagtcgcgg acccgttcgg cctcagtccg ctggccgagg tcgactaccg gccggtgaag   1680
cacgagctcg cgccgtacgg                                               1700
```

PLANT GENOMIC DNA FLANKING SPT EVENT AND METHODS FOR IDENTIFYING SPT EVENT

CROSS REFERENCE

This utility application is a continuation of U.S. Utility application Ser. No. 12/371,800 filed Feb. 16, 2009 which claims the benefit of U.S. Provisional Application Ser. No. 61/028,680, filed Feb. 14, 2008; U.S. Provisional Application Ser. No. 61/110,018 filed Oct. 31, 2008 and U.S. Provisional Application Ser. No. 61/111,892 filed Nov. 6, 2008, all of which are incorporated herein by reference.

FIELD OF THE INVENTION

Embodiments of the present invention relate to the field of plant molecular biology. More specifically, embodiments of this invention relate to transgenic maize plants containing a seed production technology (SPT) event and plant genomic DNA flanking the transgenic sequence.

BACKGROUND OF THE INVENTION

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising, et al., (1988) *Ann. Rev. Genet* 22:421-477). At the same time the presence of the transgene at different locations in the genome influences the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. It is also observed that the transgene insertion can affect the endogenous gene expression. For these reasons, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence or absence of a particular event in a plant or seed, or progeny of such plants or seeds, not only with respect to the transgene itself, but also with respect to its location in the genome of a host plant or seed. It would be particularly advantageous to be able to detect the presence of an event in order to determine whether progeny of a sexual cross contain a transgene of interest. In addition, a method for detecting a particular event would be helpful for complying with regulations requiring the pre-market approval and labeling of foods derived from recombinant crop plants, or for use in environmental monitoring, monitoring traits in crops in the field, or monitoring products derived from a crop harvest, as well as, for use in ensuring compliance of parties subject to regulatory or contractual terms. Event-specific detection methods can identify a unique junction between the inserted DNA and the recipient genome.

BRIEF SUMMARY OF THE INVENTION

Maize has been modified by the insertion of the SPT event as described herein. Relevant descriptions were also provided in US Patent Application Publication Number 2009/0038026; and in US Patent Application Publication Number 2006/0288440. The genetic elements in the T-DNA of PHP24597, used to create Event E6611.32.1.38, are summarized in Table 12.

Provided are compositions and methods related to transgenic maize plants containing the specific exogenous DNA that was introduced via standard maize transformation, referred to herein as "Seed Production Technology (SPT) event" or "Event E6611.32.1.38" or "E6611.32.1.38" or "Event DP-32138-1" or "DP-32138-1" or "Event 32138" or "32138". The transformed plants or seeds may also be referred to as "32138" or "32138 maize". Also provided are constructs useful for generating transgenic events, and materials and methods useful for identifying particular transgenic events that result in transgenic plants that comprise the SPT event.

Further provided are the seeds deposited as ATCC Patent Deposit Number PTA-9158 and plants, plant cells, plant parts, grain and plant products derived therefrom. Applicant(s) have made a deposit of at least 2500 seeds of maize event 32138 (designated as E6611.32.1.38) with the American Type Culture Collection (ATCC®), Manassas, Va. 20110-2209 USA, on Apr. 15, 2008, and the deposits were assigned ATCC Deposit Number PTA-9158. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112. The seeds deposited with the ATCC on Apr. 15, 2008, were taken from the deposit maintained by Pioneer Hi-Bred International, Inc., 7250 NW $62^{nd}$ Avenue, Johnston, Iowa 50131-1000. Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. §1.808, sample(s) of the deposit made. This deposit of seed of maize event 32138 will be maintained in the ATCC depository, which is a public depository, for a period of 30 years, or 5 years following the most recent request, or for the enforceable life of the patent, whichever is longer, and will be replaced if it becomes nonviable during that period. Additionally, Applicant(s) have satisfied all the requirements of 37 C.F.R. §§1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to event 32138 under the Plant Variety Protection Act (7 USC 2321, et seq.). Unauthorized seed multiplication prohibited. The seed may be regulated.

An additional embodiment of the invention relates to the specific flanking sequences described herein, which can be used to develop specific identification methods for E6611.32.1.38 in biological samples. Further embodiments relate to the left border and/or right border flanking regions of E6611.32.1.38, which can be used for the development of specific primers and probes. A further embodiment of the invention relates to identification methods for the presence of E6611.32.1.38 in biological samples based on the use of such specific primers or probes.

According to another embodiment of the invention, methods of detecting the presence of DNA corresponding to Event E6611.32.1.38 in a sample are provided. In a particular embodiment, methods comprise: (a) contacting the sample comprising DNA with a DNA primer set that, when used in a nucleic acid amplification reaction with genomic DNA extracted from a plant comprising event E6611.32.1.38, produces an amplicon that is diagnostic for event E6611.32.1.38; (b) performing a nucleic acid amplification reaction, thereby producing the amplicon and (c) detecting the amplicon.

A DNA molecule comprising the novel transgene/flanking insertion region, for example the sequence indicated in FIG. 11, or a molecule homologous or complementary thereto, is an embodiment of this invention.

Additional embodiments comprise DNA sequences that comprise the novel flanking and transgene flanking/insertion regions of SEQ ID NO: 1 or FIG. 11. DNA sequences that comprise a sufficient length of polynucleotides of transgene insert sequence and a sufficient length of polynucleotides of maize genomic and/or flanking sequence of SEQ ID NO: 1 or FIG. 11 that are useful as primer sequences for the production of an amplicon product diagnostic for plants comprising Event E6611.32.1.38 are additional embodiments of the invention.

Further embodiments of the invention include the DNA sequences that comprise at least 11 or more nucleotides of the transgene portion of the DNA sequence of the T-DNA region of 32138 maize, or complements thereof, and a similar length of flanking maize DNA sequence indicated in SEQ ID NO: 1 or FIG. 11, or complements thereof. These DNA sequences may be useful as DNA primers in DNA amplification methods. The amplicons produced using these primers are diagnostic for event E6611.32.1.38. Therefore, embodiments of the invention also include the amplicons produced by DNA primers homologous or complementary to the transferred T-DNA region of 32138 maize alone or in combination with the identified flanking sequences.

According to another embodiment of the invention, methods of detecting the presence of a DNA molecule corresponding to event E6611.32.1.38 in a sample are provided, such methods comprising: (a) contacting the sample comprising DNA extracted from a plant with a DNA probe, said probe comprising a molecule that hybridizes under stringent hybridization conditions with DNA extracted from event E6611.32.1.38 and does not hybridize under the stringent hybridization conditions with a control plant DNA; (b) subjecting the sample and probe to stringent hybridization conditions and (c) detecting hybridization of the probe to the DNA. More specifically, another embodiment of the invention comprises methods for detecting the presence of a DNA molecule corresponding to the event E6611.32.1.38 event in a sample, such methods consisting of (a) contacting the sample, which comprises DNA extracted from a maize plant, with a DNA probe molecule that consists of sequences that are unique to the event, e.g., junction sequences, wherein said DNA probe molecule hybridizes under stringent hybridization conditions with DNA extracted from a plant comprising maize event E6611.32.1.38 and does not hybridize under the stringent hybridization conditions with a control maize plant DNA; (b) subjecting the sample and probe to stringent hybridization conditions and (c) detecting hybridization of the probe to the DNA.

Another embodiment of the invention further relates to a DNA detection kit for identifying Event E6611.32.1.38 in biological samples. The kit comprises a first primer which specifically recognizes the left or right border flanking region of E6611.32.1.38, and a second primer which specifically recognizes a sequence within the foreign DNA of E6611.32.1.38, for use in a PCR identification protocol. A further embodiment of the invention relates to a kit for identifying event E6611.32.1.38 in biological samples, which kit comprises a specific probe having a sequence which corresponds or is complementary to, a sequence having between 80% and 100% sequence identity with a specific region of event E6611.32.1.38. The sequence of the probe corresponds to a specific region comprising part of the 5' or 3' flanking region of event E6611.32.1.38.

Further embodiments of the invention relate to using the methods and kits encompassed by the embodiments of the present invention for different purposes such as, but not limited to, the following: to identify event E6611.32.1.38 in plants, plant material or in products such as, but not limited to, food or feed products (fresh or processed) comprising or derived from plant material; identifying transgenic plant material for purposes of segregation between transgenic and non-transgenic material; and determining the quality of plant material comprising maize event E6611.32.1.38. The kits may also contain the reagents and materials necessary for the performance of the detection method.

In another aspect, the present invention provides a method for producing progeny plants comprising Event E6611.32.1.38. The progeny plants may be inbred or hybrid plants. In a further application, the present invention provides a method for performing marker-assisted breeding for Event E6611.32.1.38. According to another aspect of the present invention, a stably transformed maize plant comprising Event E6611.32.1.38 is provided.

BRIEF DESCRIPTION OF THE DRAWINGS

FIG. 1 provides a plasmid map of PHP24597.

FIG. 2 provides a map of the T-DNA region from plasmid PHP24597.

FIG. 3 provides a map of the insertion in DP-32138-1 maize and a schematic of restriction digests of the insertion based on Southern blot analysis data from this study. BamH I, Bgl II, Bmt I, EcoR I, Hind III, and Xho I restriction enzyme sites are indicated. Southern blot analysis indicated a single copy of the PHP24597 T-DNA had inserted within the maize genome. Locations of enzyme sites outside the T-DNA region are not to scale. An asterisk (*) indicates that the relative locations of these enzyme sites are uncertain due to the large size of the fragments generated from these sites. Dashed vertical lines indicate the BamH I and Bgl II sites located outside the Left Border junction that demonstrated blocked digestion on the Southern blots.

FIG. 4 provides a schematic diagram of PHP24597 without restriction sites.

FIG. 5 provides a schematic diagram of the T-DNA region of PHP24597.

FIG. 6 provides a schematic map of T-DNA from plasmid PHP24597 genetic elements with location of primers (08-0-2544/08-0-2582) used for construct-specific PCR.

FIG. 7 shows results of construct-specific PCR analysis of leaf DNA from 32138 maize and non-genetically-modified control maize. PCR amplification was conducted with primer set 08-0-2544/08-0-2582 targeting the unique 5126 promoter/Ms45 gene junction of PHP24597 T-DNA present in 32138 maize. Expected amplicon size is 233 bp. Samples were loaded as indicated in FIG. 7.

FIG. 8 shows results of maize invertase gene PCR analysis of leaf DNA from 32138 maize and non-genetically-modified control maize. PCR amplification of endogenous maize invertase gene with primer set 02-O-197/02-O-198, targeting the maize invertase gene, was used as a positive control for PCR amplification. Expected amplicon size is 225 bp. Samples were loaded as indicated in FIG. 8.

FIG. 9 shows the sensitivity of PCR analysis for 32138 maize for leaf DNA samples.

Figure 15:
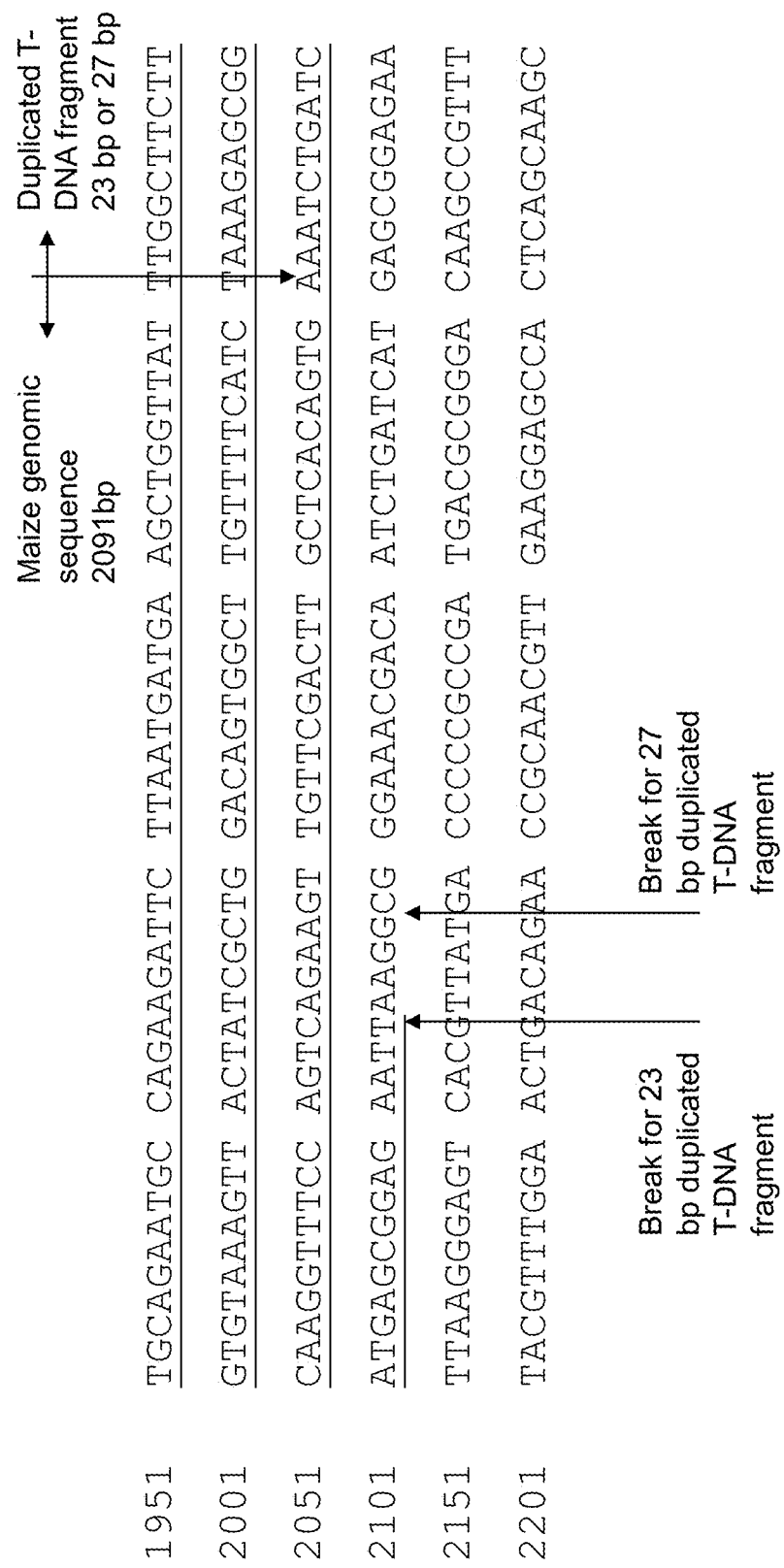

PCR amplification was conducted with primer set 08-0-2544/08-0-2582 targeting the unique 5126 promoter/Ms45 gene junction of PHP24597 T-DNA present in 32138 maize. Expected amplicon size is 233 bp. Samples were loaded as follows: decreasing amount of 32138 maize DNA (Lanes 3-10), and non-genetically modified control DNA (Lane 12).

FIG. 10 is a schematic representation of insert and genomic border regions sequenced in 32138 maize. The diagram indicates the PCR fragments generated from 32138 maize genomic DNA that were cloned and sequenced: Fragment A (07-0-2286/07-0-2277), Fragment B (08-0-2329/08-0-2398), Fragment C (08-0-2402/07-0-2024), Fragment D (08-0-2505/08-0-2504) and Fragment E (08-0-2408/08-0-2526). The vertical dashed line represents the genomic border/insert junction. Fragment F (08-0-2528/08-0-2538) and G (08-0-2539/08-0-2530) represent the 5' and 3' genomic border regions, respectively. FIG. 10 is not drawn to scale.

FIG. 11 provides the sequence of T-DNA insert and genomic border regions in 32138 maize. The 5' and 3' genomic border regions are underlined: bp1 to 2114 and by 119997 to 13998, respectively. Directly upstream of the complete insert at positions 2115-11996, within the "genomic border region," is a partial insert of T-DNA, as shown in FIG. 15.

FIG. 12 shows results of PCR analysis of the 5' and 3' genomic border regions in 32138 maize and control maize plants. 12A: Primer pair 08-0-2528/08-0-2538 amplifies a PCR product (294 bp) from within the 5' flanking genomic DNA. 12B: Primer pair 08-0-2539/08-0-2530 amplifies a PCR product (297 bp) from within the 3' genomic border region.

FIG. 13 is a schematic map of plasmid PHP24597 indicating EcoR I and BamH I restriction enzyme sites with base pair positions. The Right border and Left border regions flank the T-DNA (FIG. 2) that is expected to be transferred during *Agrobacterium*-mediated transformation. The location of the probes used for Southern analysis is indicated as lettered boxes inside the plasmid map. A: RB probe; B: LB probe; C: spc probe; D: virG probe; E: tet probe.

FIG. 14 is a schematic map of T-DNA from PHP24597 indicating restriction enzyme sites for BamH I, Bmt I, EcoR I, and Hind III and the Ms45, zm-aa1 and DsRed2(Alt1) coding and regulatory regions. T-DNA size is 9950 bp. The locations of the probes used are shown as numbered boxes below the map and are identified further in the figure.

FIG. 15 is a schematic showing detail of the 5' flanking sequence and insertion site. Alternative characterizations of the 23 bp or 27 bp partial insert are provided.

BRIEF DESCRIPTION OF THE SEQUENCES

SEQ ID NO: 1 is the 13,998-base pair region of 32138 maize which comprises 2114 bp of the 5' genomic border sequence, 2002 bp of the 3' genomic border sequence, and 9882 bp of inserted T-DNA from PHP24597.

SEQ ID NOS: 2-5 are primer sequences used in PCR reactions; see also, Table 17.

SEQ ID NOS: 6-19 are primer sequences used in PCR reactions; see also, Table 16.

SEQ ID NO: 20 is the deduced amino acid sequence from translation of the spliced exons from the Ms45 gene from plasmid PHP24597. The full-length MS45 protein is 412 amino acids in length and weighs approximately 47 kDa.

SEQ ID NO: 21 is the deduced amino acid sequence from translation of the zm-bt1 transit peptide+zm-aa1 region from plasmid PHP24597. The complete translation product, including transit peptide (amino acids 1-75) is 495 amino acids in length and weighs approximately 54 kDa. The processed ZM-AA1 protein, with the transit peptide removed, is 420 amino acids in length and weighs approximately 46 kDa.

SEQ ID NOS: 22 and 23 are forward and reverse primers, respectively, for a qPCR method for detecting the 32138 event.

SEQ ID NO: 24 is the sequence for a fluorescent-labeled probe for a qPCR method for detecting the 32138 event.

SEQ ID NO: 25 is an amplicon raised using SEQ ID NOS: 22-24 in the qPCR method for detecting the 32138 event. The amplicon spans the 3' junction.

SEQ ID NOS: 26 and 27 are forward and reverse primers, respectively for a gel-based method for detecting the 32138 event.

SEQ ID NO: 28 is an amplicon raised using SEQ ID NOS: 26 and 27 in the gel-based method for detecting the 32138 event. The amplicon spans the 3' junction.

SEQ ID NOS 29 and 30 are forward and reverse primers, respectively, for detection of the 32138 event.

SEQ ID NO: 31 is the sequence for a fluorescent-labeled probe for detection of the 32138 event.

SEQ ID NO: 32 is an amplicon raised using SEQ ID NOS: 29-31 in detecting the 32138 event.

SEQ ID NO: 33 is the deduced amino acid sequence from translation of the DsRed2(Alt1) gene from plasmid PHP24597. The DsRED2 protein is 225 amino acids in length and weighs approximately 26 kDa.

SEQ ID NO: 34 represents T-DNA of PHP24597 with right and left border repeats indicated. Description and position of genetic elements is provided in Table 12.

SEQ ID NO: 35 provides the DsRed2(Alt1) coding sequence as indicated.

SEQ ID NO: 36 provides a partial insert and left border flanking sequence of event 32138.

SEQ ID NO: 37 provides a partial insert and right border flanking sequence of event 32138.

ABBREVIATIONS

Certain abbreviations are used herein, including the following:

| | |
|---|---|
| 5126 | Anther-specific gene from maize |
| Bp | Base pair |
| DIG | Digoxigenin |
| ID | Identifier |
| In2-1 | Benzenesulfonamide-inducible 2-1 gene from maize |
| Kb | Kilobase or Kilobase pair |
| LB | Left T-DNA border |
| Ltp2 | Aleurone-specific lipid transfer protein 2 gene from *Hordeum vulgare* |
| Ms45 | Maize fertility restoration gene |
| Ms45 Genomic | Ms45 gene and associated 3' untranslated region |

-continued

| | |
|---|---|
| NaOH | Sodium hydroxide |
| NCBI | National Center for Biotechnology Information |
| PCR | Polymerase chain reaction |
| pinII | Proteinase inhibitor II gene from Solanum tuberosum |
| RB | Right T-DNA border |
| SDS | Sodium dodecyl sulfate |
| SSC | 0.015M sodium citrate, 0.15M sodium chloride, pH 7.0 |
| T-DNA | Transferred DNA |
| zm-aa1 | Truncated version of the α-amylase gene from maize |
| zm-bt1 | Transit peptide from the Brittle-1 gene from maize |

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the term "event E6611.32.1.38 specific" refers to a polynucleotide sequence which is suitable for discriminatively identifying event E6611.32.1.38 in plants, plant material, or in products such as, but not limited to, food or feed products (fresh or processed) comprising or derived from, plant material.

As used herein, the term "maize" is any maize plant and includes all plant varieties that can be bred with maize. As used herein, the term "plant" includes whole plants, plant cells, plant organs, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, stalks, roots, root tips, anthers and the like. Parts of transgenic plants understood to be within the scope of the invention comprise, for example, plant cells, protoplasts, tissues, callus, embryos as well as flowers, stems, fruits, leaves and roots originating in transgenic plants or their progeny previously transformed with a DNA molecule of the invention and therefore consisting at least in part of transgenic cells. Grain is intended to mean the mature seed produced by commercial growers for purposes other than growing or reproducing the species. Progeny, variants, and mutants of the regenerated plants are also included within the scope of the invention, provided that these plants comprise a E6611.32.1.38 event. The class of plants that can be used in the methods of the invention is generally as broad as the class of higher plants amenable to transformation techniques, including both monocotyledonous and dicotyledonous plants.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" to refers any gene that is not a native gene, comprising regulatory and coding sequences that are not found together in nature. Accordingly, a chimeric gene may comprise regulatory sequences and coding sequences that are derived from different sources or regulatory sequences and coding sequences derived from the same source, but arranged in a manner different than that found in nature. "Endogenous gene" refers to a native gene in its natural location in the genome of an organism. "Foreign" refers to material not normally found in the location of interest. Thus "foreign DNA" may comprise recombinant DNA and/or newly introduced, rearranged DNA of the plant. Foreign genes can comprise native genes inserted into a non-native organism, or chimeric genes. A "transgene" is a gene that has been introduced into the genome by a transformation procedure. The site in the plant genome where a recombinant DNA has been inserted may be referred to as the "insertion site" or "target site".

"Flanking DNA" can comprise either genomic DNA naturally present in an organism such as a plant, or foreign (heterologous) DNA introduced via the transformation process, e.g. fragments associated with the transformation event. Thus, flanking DNA may include a combination of native and foreign DNA. A "flanking region" or "flanking sequence" or "genomic border region" or "genomic border sequence" as used herein refers to a sequence of at least 3, 5, 10, 11, 15, 20, 50, 100, 200, 300, 400, 1000, 1500, 2000, 2500 or 5000 base pairs or greater which is located either immediately upstream or downstream of, and contiguous with, the original foreign insert DNA molecule. When this flanking region is located downstream it may also be referred to as "left border flank" or "3' flank" or "3' genomic border region" or "genomic 3' border sequence", and the like. When this flanking region is located upstream it may also be referred to as the "right border flank" or "5' flank" or "5' genomic border region" or "genomic 5' border sequence", and the like. Non-limiting examples of the flanking regions of the E6611.32.1.38 event are set forth in SEQ ID NO: 1 (bp 1-2114 and by 11,997-13, 998) and FIG. 11 (see, underlined regions).

Transformation procedures leading to random integration of the foreign DNA will result in transformants containing different flanking regions characteristic of and unique for each transformant. When recombinant DNA is introduced into a plant through traditional crossing, its flanking regions will generally not be changed. Transformants will also contain unique junctions between a piece of heterologous insert DNA and genomic DNA, or two (2) pieces of genomic DNA, or two (2) pieces of heterologous DNA. A "junction" is a point where two (2) specific DNA fragments join. For example, a junction exists where insert DNA joins flanking DNA. A junction point also exists in a transformed organism where two (2) DNA fragments join together in a manner that is modified from that found in the native organism. "Junction DNA" refers to DNA that comprises a junction point. Junction points for the E32138 event are apparent from FIG. 11 and FIG. 15.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived or, if from the same or analogous species, the promoter is not naturally found operably linked to the nucleotide sequence. A heterologous protein may originate from a foreign species or, if from the same or analogous species, is substantially modified from its original form.

"Regulatory sequences" refer to nucleotide sequences located upstream (5' non-coding sequences), within or downstream (3' non-coding sequences) of a coding sequence, and which influence the transcription, RNA processing or stability, or translation of the associated coding sequence. Regulatory sequences may include promoters, translation leader sequences, introns and polyadenylation recognition sequences.

"Promoter" refers to a nucleotide sequence capable of controlling the expression of a coding sequence or functional RNA. In general, a coding sequence is located 3' to a promoter sequence. The promoter sequence can comprise proximal and more distal upstream elements. The more distal upstream elements are often referred to as enhancers. Accordingly, an "enhancer" is a nucleotide sequence that can stimulate promoter activity and may be an innate element of the promoter or a heterologous element inserted to enhance the activity level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster, (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by effecting the addition of polyadenylic acid tracts to the 3' end of the mRNA precursor. The use of different 3' non-coding sequences is exemplified by Ingelbrecht, et al., (1989) *Plant Cell* 1:671-680.

A "protein" or "polypeptide" is a chain of amino acids arranged in a specific order determined by the coding sequence in a polynucleotide encoding the polypeptide.

A "DNA construct" is an assembly of DNA molecules linked together that provide one or more expression cassettes. The DNA construct may be a plasmid that is enabled for self replication in a bacterial cell and contains various endonuclease enzyme restriction sites that are useful for introducing DNA molecules that provide functional genetic elements, i.e., promoters, enhancers, introns, leaders, coding sequences, 3' termination regions, among others; or a DNA construct may be a linear assembly of DNA molecules, such as an expression cassette. The expression cassette contained within a DNA construct comprises the necessary genetic elements to provide transcription of a messenger RNA. The expression cassette can be designed to express in prokaryote cells or eukaryotic cells. Expression cassettes of the embodiments of the present invention are designed to express in plant cells.

The DNA molecules of embodiments of the invention may be provided in expression cassettes for expression in an organism of interest. The cassette may include 5' and 3' regulatory sequences operably linked to a coding sequence. "Operably linked" is intended to mean a functional linkage between two or more elements. For example, an operable linkage between a polynucleotide of interest and a regulatory sequence (i.e., a promoter) is a functional link that allows for the expression of the polynucleotide of interest. The operably linked regulatory sequence may initiate and mediate transcription of the polynucleotide of interest. Operably linked elements may be contiguous or non-contiguous. When used to refer to the joining of two protein coding regions, operably linked is intended to mean that the coding regions are in the same reading frame. The cassette may additionally contain at least one additional gene to be cotransformed into the organism. Alternatively, the additional gene(s) can be provided on multiple expression cassettes or multiple DNA constructs. Such an expression cassette may be provided with a plurality of restriction sites and/or recombination sites for insertion of the polynucleotide to be under the transcriptional regulation of the regulatory regions. The expression cassette may additionally contain selectable marker genes.

The expression cassette may include in the 5' to 3' direction of transcription, a transcriptional and translational regulatory region (i.e., a promoter), a coding region, and a transcriptional and translational termination region functional in plants. The transcriptional regulatory region (e.g., the promoter) may be native or analogous or foreign or heterologous to the host organism. Additionally, the promoter may be the natural sequence or alternatively a synthetic sequence. The expression cassettes may additionally contain 5' leader sequences in the expression cassette construct. Such leader sequences can act to enhance translation. The regulatory regions (e.g., promoters, transcriptional regulatory regions, RNA processing or stability regions, introns, polyadenylation signals and translational termination regions) and/or the coding region may be native/analogous or heterologous to the host cell or to each other.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved. The expression cassette can also comprise a selectable marker gene for the selection of transformed cells. Selectable marker genes are utilized for the selection of transformed cells or tissues.

It is to be understood that as used herein the term "transgenic" includes any cell, cell line, callus, tissue, plant part or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant and selection of a particular plant characterized by insertion into a particular genome location.

Typically, a number of plant cells are transformed, producing a population of plants from which a particular plant is selected. The term "event" refers to the original transformant and progeny of the transformant that include the exogenous DNA inserted into a particular and unique location in the genome, i.e., event DNA. The term "event" also refers to progeny produced by a sexual outcross, a self-pollination or repeated backcrossing, wherein at least one of the plants used in the breeding is of any generation of the original transformant containing event DNA.

An event is characterized phenotypically by the expression of the transgene. At the genetic level, an event is part of the genetic makeup of a plant. The term "event" also refers to progeny produced by a sexual outcross between the transformant and another variety wherein the progeny include the heterologous DNA. Even after repeated back-crossing to a recurrent parent, the inserted DNA and flanking DNA from the transformed parent are present in the progeny of the cross at the same chromosomal location. The term "event" also refers to DNA from the original transformant, comprising the inserted DNA and flanking sequence immediately adjacent to the inserted DNA, that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Thus, a transgenic "event" is a plant comprising and defined by an "event DNA." In this way, "Event E6611.32.1.38" comprises "E6611.32.1.38 Event DNA." A plant may comprise two or more different event DNAs and thus comprise two or more different events. In addition, a plant lacking a given transgene event X does not comprise that event DNA X in question. Event DNA may be transferred from plant to plant, generation to generation, by any breeding scheme, method, or tool known to those of skill in the art of plant breeding.

Transformation of plants typically utilizes a selectable marker and selection method to distinguish the transformed cells of the culture from the non-transformed cells. In some instances the selectable marker gene remains in the transgenic plant; in other instances it is desirable to remove the selectable marker gene or other sequences introduced in the exogenous DNA. Homologous recombination is one method useful for the deletion of marker genes residing within a transgenic plant (U.S. Pat. No. 6,580,019, incorporated herein by reference in its entirety). Another useful tool for removing sequences from a plant involves the use of site-specific recombinase enzymes and their respective site-specific target sites.

A number of different site-specific recombinase systems could be employed in accordance with the instant invention, including, but not limited to, the Cre/lox system of bacteriophage P1 and the FLP/FRT system of yeast. The bacteriophage P1 Cre/lox and the yeast FLP/FRT systems constitute two particularly useful systems for site-specific integration or excision of transgenes. In these systems, a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors. The FLP/FRT and Cre/lox recombinase systems have been demonstrated to function efficiently in plant cells. In a particular embodiment, a Cre/lox recombinase system is employed to remove selectable marker sequences, particularly an NPT II marker gene flanked by lox P recombination sites. (Russell, et al., (1992) *Mol. Gen. Genet.* 234:45 59).

DNA molecules are provided that comprise at least a portion of the heterologous insert DNA and plant genomic flanking DNA (referred to herein as a "junction sequence" or "junction").

The term "Event E6611.32.1.38 DNA" refers to a DNA segment comprising an insertion of the T-DNA of FIG. 2 (see also, by 2115-11,996 of SEQ ID NO: 1) into a particular location in the genome and adjacent flanking DNA that would be expected to be transferred to a progeny plant from a parent plant containing the inserted DNA. More specifically, Event E6611.32.1.38 DNA also refers to each of the DNA regions that include an interface of the plant native genomic DNA and the integrated transgenic DNA in the genome of the plant, e.g., a region around one interface where the 5' end is in plant native genomic DNA and the 3' end is in integrated transgenic DNA. In addition, the sequence of the exogenous DNA may be altered while resident in its particular location in a host genome, e.g., a portion of the sequence may be changed, deleted or amplified and still constitute said event DNA, providing said exogenous DNA continues to reside in the same location in the genome.

A E6611.32.1.38 plant can be bred by first sexually crossing first and second parental plants. The first parental plant is a plant grown from the transgenic E6611.32.1.38 plant or progeny thereof, i.e., derived from transformation with the expression cassettes of the embodiments of the present invention that confer seed production technology. The first parental plant is pollinated by a second parental plant, thereby producing a plurality of first progeny plants, and a first progeny plant is selected that comprises the SPT event. The first progeny plant may be selfed, thereby producing a plurality of second progeny plants; and from the second progeny plants is selected a plant comprising the SPT event. These steps can further include the back-crossing of a progeny plant comprising the SPT event to the second parental plant or a third parental plant, thereby producing a plant comprising the SPT event. The SPT event is transmitted through female gametes and not male gametes.

Two different transgenic plants can also be sexually crossed to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox, ed., American Society of Agronomy, Madison Wis. (1987).

The term "germplasm" refers to an individual, a group of individuals, or a clone representing a genotype, variety, species or culture, or the genetic material thereof.

A "line" or "strain" is a group of individuals of identical parentage that are generally inbred to some degree and that are generally isogenic or near isogenic.

Inbred maize lines are typically developed for use in the production of maize hybrids and for use as germplasm in breeding populations for the creation of new and distinct inbred maize lines. Inbred maize lines are often used as targets for the introgression of novel traits through traditional breeding and/or molecular introgression techniques. Inbred maize lines need to be highly homogeneous, homozygous and reproducible to be useful as parents of commercial hybrids.

Many analytical methods are available to determine the homozygosity and phenotypic stability of inbred lines.

The phrase "hybrid plants" refers to plants which result from a cross between genetically different individuals.

As used herein "crossed" or "cross" is intended to mean the fusion of gametes, e.g., via pollination to produce progeny (i.e., cells, seeds or plants) in the case of plants. The term encompasses both sexual crosses (the pollination of one plant by a genetically distinct plant) and selfing (self-pollination, i.e., when the pollen and ovule are from the same plant or from genetically identical plants).

The term "introgression" refers to the transmission of a desired allele of a genetic locus from one genetic background to another. In one method, the desired alleles can be introgressed through a sexual cross between two parents, wherein at least one of the parents has the desired allele in its genome.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere, et al., (1987) *Meth. Enzymol.* 143:277) and particle-accelerated or "gene gun" transformation technology (Klein, et al., (1987) *Nature* (London) 327:70-73; U.S. Pat. No. 4,945,050, incorporated herein by reference). Additional transformation methods are disclosed below.

Thus, isolated polynucleotides of the invention can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels, et al., (1985; Supp. 1987) Cloning Vectors: A Laboratory Manual, Weissbach and Weissbach (1989) Methods for Plant Molecular Biology, (Academic Press, New York); and Flevin, et al., (1990) Plant Molecular Biology Manual, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site and/or a polyadenylation signal.

A "probe" is an isolated polynucleotide to which is attached a conventional detectable label or reporter molecule, e.g., a radioactive isotope, ligand, chemiluminescent agent or enzyme. Such a probe is complementary to a strand of a target polynucleotide, for example, in some embodiments, to a strand of isolated DNA from event E6611.32.1.38 whether from a plant or from a sample that includes DNA from the event. Probes include not only deoxyribonucleic or ribonucleic acids but also polyamides and other probe materials that bind specifically to a target DNA sequence and can be used to detect the presence of that target DNA sequence.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference). Any combination of primers disclosed herein can be used such that the pair allows for the detection of a E6611.32.1.38 event or specific region. Non-limiting examples of primer pairs include SEQ ID NOS: 6 and 7, 8 and 9, 10 and 11, 12 and 13, 14 and 15, 16 and 17 and 18 and 19, as shown in Table 16.

Probes and primers are of sufficient nucleotide length to bind to the target DNA sequence and specifically detect and/or identify a polynucleotide having a E6611.32.1.38 event. It is recognized that the hybridization conditions or reaction conditions can be determined by the operator to achieve this result. Generally, 5, 8, 11, 14, 16, 18, 20, 22, 24, 26, 28, 30, 40, 50, 75, 100, 200, 300, 400, 500, 600, 700 nucleotides or more or between about 11-20, 20-30, 30-40, 40-50, 50-100, 100-200, 200-300, 300-400, 400-500, 500-600, 600-700, 700-800 or more nucleotides in length are used. Such probes and primers can hybridize specifically to a target sequence under high stringency hybridization conditions. Probes and primers may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide, or can differ from the target sequence by 1, 2, 3, 4, 5, 6 or more contiguous nucleotides. Probes can be used as primers, but are generally designed to bind to the target DNA or RNA and are not used in an amplification process.

Specific primers can be used to amplify an integration fragment to produce an amplicon that can be used as a "specific probe" for identifying event E6611.32.1.38 in biological samples. Alternatively, a probe can be used during the PCR reaction to allow for the detection of the amplification event (i.e., a Taqman probe or a MGB probe, so-called real-time PCR). When the probe is hybridized with the polynucleotides of a biological sample under conditions which allow for the binding of the probe to the sample, this binding can be detected and thus allow for an indication of the presence of event E6611.32.1.38 in the biological sample. Such identification of a bound probe has been described in the art. In one embodiment, the specific probe is a sequence which, under optimized conditions, hybridizes specifically to a region within the 5' or 3' flanking region of the event and also comprises a part of the foreign DNA contiguous therewith. The specific probe may comprise a sequence at least 80%, between 80 and 85%, between 85 and 90%, between 90 and 95% or between 95 and 100% identical (or complementary) to a specific region of the E6611.32.1.38 event. A quantitative real-time PCR assay specific for the E6611.32.1.38 event may comprise, for example, the primer pair of SEQ ID NOS: 29 and 30 and the fluorescent probe of SEQ ID NO: 31.

Methods for preparing and using probes and primers are described, for example, in Molecular Cloning: A Laboratory Manual, 2.sup.nd ed, vol. 1-3, ed. Sambrook, et al., Cold Spring Harbor Laboratory Press, Cold Spring Harbor, N.Y. 1989 (hereinafter, "Sambrook, et al., 1989"); Current Protocols in Molecular Biology, ed. Ausubel, et al., Greene Publishing and Wiley-Interscience, New York, 1992 (with periodic updates) (hereinafter, "Ausubel, et al., 1992"); and Innis, et al., PCR Protocols: A Guide to Methods and Applications, Academic Press San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.) and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

As used herein, "kit" refers to a set of reagents for the purpose of performing the method embodiments of the inventions, more particularly, the identification and/or the detection of the E6611.32.1.38 event in biological samples. The kit can be used, and its components can be specifically adjusted, for purposes of quality control (e.g., purity of seed lots), detection of event E6611.32.1.38 in plant material, or material comprising or derived from plant material, such as but not limited to food or feed products. "Plant material" as used herein refers to material which is obtained or derived from a plant.

In specific embodiments, a kit for identifying event E6611.32.1.38 in a biological sample is provided. The kit comprises a first and a second primer, wherein the first and second primer amplify a polynucleotide comprising a E6611.32.1.38 and/or flanking DNA specific region. In further embodiments, the kit also comprises a polynucleotide for the detection of the E6611.32.1.38 and/or flanking DNA specific region. The kit can comprise, for example, a first primer comprising a fragment of a polynucleotide of SEQ ID NO: 1, 2, 3, 4 or 5 wherein the first or the second primer shares sufficient sequence identity or complementarity to the polynucleotide to amplify said E6611.32.1.38 and/or flanking DNA specific region. The primer pair can comprise a fragment of SEQ ID NO: 1 and a fragment of any of SEQ ID NOS: 2-3 and 6-19. The primers can be of any length sufficient to amplify the E6611.32.1.38 region including, for example, at least 6, 7, 8, 9, 10, 15, 20, 15 or 30 or about 7-10, 10-15, 15-20, 20-25, 25-30, 30-35, 35-40, 40-45 nucleotides or longer.

Further provided are DNA detection kits comprising at least one polynucleotide that can specifically detect a E6611.32.1.38 and/or flanking DNA specific region, wherein said polynucleotide comprises at least one DNA molecule of a sufficient length of contiguous nucleotides homologous or complementary to SEQ ID NO: 1.

Primers and probes based on the flanking DNA and insert sequences disclosed herein can be used to confirm (and, if necessary, to correct) the disclosed sequences by conventional methods, e.g., by re-cloning and sequencing such sequences. The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an antiparallel, double-stranded nucleic acid structure.

In hybridization techniques, all or part of a polynucleotide that selectively hybridizes to a target polynucleotide having a E6611.32.1.38 specific event is employed. By "stringent conditions" or "stringent hybridization conditions" when referring to a polynucleotide probe, conditions under which a probe will hybridize to its target sequence to a detectably greater degree than to other sequences (e.g., at least 2-fold over background) are intended. Regarding the amplification of a target polynucleotide (e.g., by PCR) using a particular amplification primer pair, "stringent conditions" are conditions that permit the primer pair to hybridize to the target polynucleotide to which a primer having the corresponding wild-type sequence (or its complement) would bind and preferably to produce an identifiable amplification product (the amplicon) having a E6611.32.1.38 specific region in a DNA thermal amplification reaction. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially complementary or identical sequence is a polynucleotide that will specifically hybridize to the nucleic acid molecule to which it is being compared, or to its complement, respectively, under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ (thermal melting point) can be approximated from the equation of Meinkoth and Wahl, (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/ or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.) and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.) and Haymes, et al., (1985) In: *Nucleic Acid Hybridization, a Practical Approach*, IRL Press, Washington, D.C.

As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook, et al., 1989, and by Haymes, et al., In: Nucleic Acid Hybridization, a Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

Any of the polynucleotides and fragments and variants thereof employed in the methods and compositions can share sequence identity to a region of the transgene insert of the E6611.32.1.38 event, a junction sequence of the E6611.32.1.38 event, or a flanking sequence of the E6611.32.1.38 event. Methods to determine the relationship of various sequences are known. As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the local alignment algorithm of Smith, et al., (1981) *Adv. Appl. Math.* 2:482; the global alignment algorithm of Needleman and Wunsch, (1970) *J. Mol. Biol.* 48:443-453; the search-for-local alignment method of Pearson and Lipman, (1988) *Proc. Natl. Acad. Sci.* 85:2444-2448; the algorithm of Karlin and Altschul, (1990) *Proc. Natl. Acad. Sci. USA* 872264, modified as in Karlin and Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65 and Pearson, et al., (1994) *Meth. Mol. Biol.* 24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the inventions. BLAST protein searches can be performed with the BLASTX program, score=50, wordlength=3, to obtain amino acid sequences homologous to a protein or polypeptide of the inventions. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch, (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff, (1989) *Proc. Natl. Acad. Sci. USA* 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

As used herein, "amplified DNA" or "amplicon" refers to the product of polynucleotide amplification of a target polynucleotide that is part of a nucleic acid template. For example, to determine whether a plant resulting from a sexual cross contains the E6611.32.1.38 event, DNA extracted from the plant tissue sample may be subjected to a polynucleotide amplification method using a DNA primer pair that includes a first primer derived from flanking sequence adjacent to the insertion site of inserted heterologous DNA, and a second primer derived from the inserted heterologous DNA, to produce an amplicon that is diagnostic for the presence of the E6611.32.1.38 event DNA. By "diagnostic" for a E6611.32.1.38 event, the use of any method or assay which discriminates between the presence and the absence of a E6611.32.1.38 event in a biological sample is intended. Alternatively, the second primer may be derived from the junction sequence. In still other embodiments, primer pairs can be derived from flanking sequence on both sides of the inserted DNA so as to produce an amplicon that includes the entire insert polynucleotide of the expression construct as well as the sequence flanking the transgenic insert. The amplicon is of a length and has a sequence that is also diagnostic for the event (i.e., has a junction DNA from a E6611.32.1.38 event). The amplicon may range in length from the combined length of the primer pairs plus one nucleotide base pair to any length of amplicon producible by a DNA amplification protocol. A member of a primer pair derived from the flanking sequence may be located a distance from the inserted DNA sequence; this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Nucleic acid amplification can be accomplished by any of the various nucleic acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis, et al., Academic Press, San Diego, 1990. PCR amplification methods have been developed to amplify up to 22 Kb of genomic DNA and up to 42 Kb of bacteriophage DNA (Cheng, et al., (1994) *Proc. Natl. Acad. Sci. USA* 91:5695-5699). These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplicon produced by these methods may be detected by a plurality of techniques, including, but not limited to, Genetic Bit Analysis (Nikiforov, et al., (1994) *Nucleic Acid Res.* 22:4167-4175) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization and single base extension.

Another detection method is the Pyrosequencing technique as described by Winge (*Innov. Pharma. Tech.* 00:18-24, 2000). In this method an oligonucleotide is designed that overlaps the adjacent DNA and insert DNA junction. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (*Genome Res.* 9:492-498, 1999) is also a method that can be used to detect an amplicon of the invention. Using this method an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al., (*Nature Biotech.* 14:303-308, 1996). Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

Many modifications and other embodiments of the inventions set forth herein will come to mind to one skilled in the art to which these inventions pertain having the benefit of the teachings presented in the present disclosure and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Compositions and methods related to transgenic plants comprising the SPT event are provided. Specifically, plants, and more particularly, maize plants, having event E6611.32.1.38 are provided. A maize plant having event E6611.32.1.38 has been modified by the insertion of the seed production technology event. The SPT event E6611.32.1.38 comprises the 5126 promoter driving MS45 Genomic DNA, the PG47 promoter driving ZM-BT1 TP encoding Brittle1 transit peptide linked to ZM-AA1 encoding alpha-amylase, and the CaMV35S enhancer combined with the LTP2 promoter to drive DS-RED2 (ALT1) encoding a variant of DISCOSOMA sp. red fluorescent protein. (See, FIG. 1; see also, U.S. patent application Ser. No. 11/833,363 filed Aug. 3, 2007, and published Feb. 5, 2009, as 2009/0038026; and US Patent Application Publication Number 2006/0288440.) The event insertion maps to Chromosome 3 at 84.1 to 84.5, between markers MZA 12392 and MZA 2358. Thus, a plant comprising event E6611.32.1.38 exhibits enhanced seed production technology capability.

The polynucleotides conferring the seed production technology are linked on the same DNA construct and are inserted at a characterized position in the maize genome and thereby produce the E6611.32.1.38 event. The plant harboring the E6611.32.1.38 event at the recited chromosomal location comprises genomic/transgene junctions as indicated in SEQ ID NO: 1 and FIGS. 11 and 15. The characterization of the genomic insertion site of the E6611.32.1.38 event provides for an enhanced breeding efficiency and enables the use of molecular markers to track the transgene insert in the breeding populations and progeny thereof. Various methods and compositions for the identification, detection, and use of plants, plant parts, seeds and grain products containing the maize E6611.32.1.38 event are provided herein.

In some embodiments, the polynucleotides conferring the maize E6611.32.1.38 event are engineered into a molecular stack. In other embodiments, the molecular stack further comprises at least one additional transgenic polynucleotide. Said polynucleotide may confer additional aspects of seed production technology or may confer an unrelated trait.

In certain embodiments, the plant is stacked with any combination of polynucleotide sequences of interest in order to create plants with a desired combination of traits. A trait, as used herein, refers to the phenotype derived from a particular sequence or groups of sequences. The combinations generated can also include multiple copies of any one or more of the polynucleotides of interest.

In some embodiments, the maize E6611.32.1.38 event can also be combined with at least one other trait to produce plants that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802 and 5,703,409; U.S. Pat. No. 5,850,016); barley high lysine (Williamson, et al., (1987) *Eur. J. Biochem.* 165:99-106; and WO 1998/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123)); increased digestibility e.g., modified storage proteins (U.S. patent application Ser. No. 10/053,410, filed Nov. 7, 2001); and thioredoxins (U.S. patent application Ser. No. 10/005,429, filed Dec. 3, 2001)); the disclosures of which are herein incorporated by reference. Desired trait combinations also include low linolenic acid content; see, e.g., Dyer, et al., (2002) *Appl. Microbiol. Biotechnol.* 59:224-230 and high oleic acid content; see, e.g., Fernandez-Moya, et al., (2005) *J. Agric. Food Chem.* 53:5326-5330.

In still further embodiments, the maize E6611.32.1.38 event can also be combined with other desirable traits such as, for example, fumonisin detoxification genes (U.S. Pat. No. 5,792,931), avirulence and disease resistance genes (Jones, et al., (1994) *Science* 266:789; Martin, et al., (1993) *Science* 262:1432; Mindrinos, et al., (1994) *Cell* 78:1089) and traits desirable for processing or process products such as modified oils (e.g., fatty acid desaturase genes (U.S. Pat. No. 5,952,544; WO 1994/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase and acetoacetyl-CoA reductase (Schubert, et al., (1988) *J. Bacteriol.* 170:5837-5847) which facilitate expression of polyhydroxyalkanoates (PHAs)); the disclosures of which are herein incorporated by reference. One could also combine seed production technology polynucleotides with polynucleotides providing agronomic traits such as male sterility (e.g., see, U.S. Pat. No. 5,583,210), improved stalk strength, altered flowering time or transformation technology traits such as cell cycle regulation or gene targeting (e.g., WO 1999/61619, WO 2000/17364 and WO 1999/25821); the disclosures of which are herein incorporated by reference.

In another embodiment, the maize E6611.32.1.38 event can also be combined with the Rcg1 sequence or a biologically active variant or fragment thereof. The Rcg1 sequence is an anthracnose stalk rot resistance gene in corn. See, for example, U.S. patent application Ser. Nos. 11/397,153, 11/397,275 and 11/397,247, each of which is herein incorporated by reference.

These stacked combinations can be created by any method including, but not limited to, breeding plants by any conventional methodology or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

As used herein, the term "polynucleotide" is not intended to be limited to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides provided herein also encompass all forms of sequences including, but not limited to, single-stranded forms, double-stranded forms, hairpins, stem-and-loop structures and the like.

Isolated polynucleotides are provided that can be used in various methods for the detection and/or identification of the maize E6611.32.1.38 event. An "isolated" or "purified" polynucleotide or biologically active portion thereof, is substantially or essentially free from components that normally accompany or interact with the polynucleotide as found in its naturally occurring environment. Thus, an isolated or purified polynucleotide is substantially free of other cellular material or culture medium when produced by recombinant techniques or substantially free of chemical precursors or other chemicals when chemically synthesized.

In specific embodiments, polynucleotides are provided that comprise the junction DNA sequences as indicated in SEQ ID NO: 1 and FIGS. 11 and 15. Fragments and variants of junction DNA sequences are suitable for discriminatively identifying event E6611.32.1.38. As discussed elsewhere herein, such sequences find use as primers and/or probes.

In other embodiments, polynucleotides that can detect a E6611.32.1.38 event or a E6611.32.1.38-specific region are provided. Such sequences include any polynucleotide set forth in SEQ ID NOS: 2-3, 6-19 and variants and fragments thereof. Fragments and variants of polynucleotides that detect a E6611.32.1.38 event or a E6611.32.1.38 specific region are suitable for discriminatively identifying event E6611.32.1.38. As discussed elsewhere herein, such sequences find use as primers and/or probes. Further provided are isolated DNA nucleotide primer or probe sequences comprising or consisting of a sequence set forth in SEQ ID NO: 2, 3, 6, 7, 8, 9, 10, 11, 12, 13, 14, 15, 16, 17, 18, 19, 22, 23, 24, 26, 27, 29, 30, 31 or a complement thereof.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide and/or substitution of one or more nucleotides at one or more sites in the native polynucleotide.

Various methods and compositions for identifying event E6611.32.1.38 are provided. Such methods find use in identifying and/or detecting a E6611.32.1.38 event in any biological material. Such methods include, for example, methods to confirm seed purity and methods for screening seeds in a seed lot for a E6611.32.1.38 event. In one embodiment, a method for identifying event E6611.32.1.38 in a biological sample is provided and comprises contacting the sample with a first and a second primer and, amplifying a polynucleotide comprising a E6611.32.1.38 specific region.

A biological sample can comprise any sample in which one desires to determine if DNA having event E6611.32.1.38 is present. For example, a biological sample can comprise any plant material or material comprising or derived from a plant material such as, but not limited to, food or feed products. In specific embodiments, the biological sample comprises a maize tissue.

Primers and probes based on the flanking DNA and insert sequences disclosed herein can be used to confirm (and, if necessary, to correct) the disclosed sequences by conventional methods, e.g., by re-cloning and sequencing such sequences. The polynucleotide probes and primers specifically detect a target DNA sequence. Any conventional nucleic acid hybridization or amplification method can be used to identify the presence of DNA from a transgenic event in a sample. By "specifically detect" it is intended that the polynucleotide can be used either as a primer to amplify a E6611.32.1.38 specific region or the polynucleotide can be used as a probe that hybridizes under stringent conditions to a polynucleotide having a E6611.32.1.38 event or a E6611.32.1.38 specific region. The level or degree of hybridization which allows for the specific detection of a E6611.32.1.38 event or a specific region of a E6611.32.1.38 event is sufficient to distinguish the polynucleotide with the E6611.32.1.38 specific region from a polynucleotide lacking this region and thereby allow for discriminately identifying a E6611.32.1.38 event. By "shares sufficient sequence identity or complementarity" to allow for the amplification of a E6611.32.1.38-specific event, is intended that the sequence shares at least 80%, 85%, 90%, 91%, 92%, 93%, 94%, 95%, 96%, 97%, 98%, 99% or 100% identity or complementarity to a fragment or across the full length of the polynucleotide having the E6611.32.1.38-specific region.

Regarding the amplification of a target polynucleotide (e.g., by PCR) using a particular amplification primer pair, "stringent conditions" are conditions that permit the primer pair to hybridize to the target polynucleotide to which a primer having the corresponding wild-type sequence (or its complement) would bind and preferably to produce an identifiable amplification product (the amplicon) having a E6611.32.1.38 specific region in a DNA thermal amplification reaction. In a PCR approach, oligonucleotide primers can be designed for use in PCR reactions to amplify a E6611.32.1.38 specific region. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Methods of amplification are further described in U.S. Pat. Nos. 4,683,195, 4,683,202 and Chen, et al., (1994) *PNAS* 91:5695-5699. These methods as well as other methods known in the art of DNA amplification may be used in the practice of the inventions. It is understood that a number of parameters in a specific PCR protocol may need to be adjusted to specific laboratory conditions and may be slightly modified and yet allow for the collection of similar results. These adjustments will be apparent to a person skilled in the art.

The amplified polynucleotide (amplicon) can be of any length that allows for the detection of the E6611.32.1.38 event or a E6611.32.1.38 specific region. For example, the amplicon can be about 10, 50, 100, 200, 300, 500, 700, 100, 2000, 3000, 4000, 5000 nucleotides in length or longer. In specific embodiments, the specific region of the E6611.32.1.38 event is detected.

Any primer can be employed in the methods provided herein that allows a E6611.32.1.38 specific region to be amplified and/or detected. For example, in specific embodiments, a primer comprises a fragment of a polynucleotide of SEQ ID NO: 1, 2, 3, 6, 7, 8, 9, 10, 11, 12, 13, 14, 15, 16, 17, 18, 19, 22, 23, 26, 27, 29 or 30 wherein the primer shares sufficient sequence identity or complementarity to the polynucleotide to amplify said E6611.32.1.38 or flanking DNA specific region. A primer pair can comprise a fragment of SEQ ID NO: 1 and a fragment of SEQ ID NO: 2, 3, 6, 7, 8, 9, 10, 11, 12, 13, 14, 15, 16, 17, 18, 19, 22, 23, 26, 27, 29 or 30. The primers can be of any length sufficient to amplify a E6611.32.1.38 region including, for example, at least 6, 7, 8, 9, 10, 15, 20, 15 or 30 or about 7-10, 10-15, 15-20, 20-25, 25-30, 30-35, 35-40, 40-45 nucleotides or longer.

As discussed elsewhere herein, any method to PCR amplify the E6611.32.1.38 event or specific region can be employed, including for example, real time PCR. See, for example, Livak, et al., (1995) Oligonucleotides with fluorescent dyes at opposite ends provide a quenched probe system for detecting PCR product and nucleic acid hybridization. PCR methods and Applications. 4:357-362; U.S. Pat. No. 5,538,848; U.S. Pat. No. 5,723,591; Applied Biosystems User Bulletin No. 2, "Relative Quantitation of Gene Expression," P/N 4303859; and, Applied Biosystems User Bulletin No. 5, "Multiplex PCR with Taqman VIC probes," P/N 4306236; each of which is herein incorporated by reference.

Thus, in specific embodiments, a method of detecting the presence of event E6611.32.1.38 or progeny thereof in a biological sample is provided. The method comprises (a) extracting a DNA sample from the biological sample; (b) providing a pair of DNA primer molecules; (c) providing DNA amplification reaction conditions; (d) performing the DNA amplification reaction, thereby producing a DNA amplicon molecule and (e) detecting the DNA amplicon molecule, wherein the detection of said DNA amplicon molecule in the DNA amplification reaction indicates the presence of maize event E6611.32.1.38. In order for a nucleic acid molecule to serve as a primer or probe it need only be sufficiently complementary in sequence to be able to form a stable double-stranded structure under the particular solvent and salt concentrations employed.

Further provided are methods of detecting the presence of DNA corresponding to the E6611.32.1.38 event in a sample. In one embodiment, the method comprises (a) contacting the biological sample with a polynucleotide probe that hybridizes under stringent hybridization conditions with DNA from maize event E6611.32.1.38 and specifically detects the E6611.32.1.38 event; (b) subjecting the sample and probe to stringent hybridization conditions and (c) detecting hybridization of the probe to the DNA, wherein detection of hybridization indicates the presence of the E6611.32.1.38 event.

Embodiments are further defined in the following Examples. It should be understood that these Examples are given by way of illustration only. From the above discussion and these Examples, one skilled in the art can ascertain the essential characteristics of this invention and without departing from the spirit and scope thereof, can make various changes and modifications of the embodiments to adapt it to various usages and conditions. Thus, various modifications of the embodiments, in addition to those shown and described herein, will be apparent to those skilled in the art from the foregoing description. Such modifications are also intended to fall within the scope of the appended claims.

EXAMPLES

Example 1

Characterization of Event DP-32138-1

Maize (*Zea mays* L.) event DP-32138-1, also referred to 32138 maize, has been produced by *Agrobacterium*-mediated transformation with the plasmid PHP24597 (FIG. 1) essentially as described in Zhao, et al., (2001) *Molecular Biology* (formerly *Molecular Breeding*) 8:323-333; U.S. Pat. No. 5,981,840; and PCT patent publication WO98/32326, all of which are hereby incorporated by reference. The T-DNA region of this plasmid is represented schematically in FIG. 2 and its sequence is provided in SEQ ID NO: 34. A summary of the genetic elements and their positions on plasmid PHP24597 and on the T-DNA are described in Tables 11 and 12, respectively. Transformation resulted in the insertion of three gene cassettes containing a fertility restoration genomic sequence, Ms45, the α-amylase gene, Zm-aa1 and the DsRed2 (Alt1) gene as a visible marker. These three gene cassettes are elements of a seed production system to create male-sterile lines for the generation of hybrid seed without the need to mechanically or manually detassel plants.

The first cassette contains the Ms45 Genomic sequence, which is a region of maize genomic DNA comprising the Ms45 gene and associated 3' untranslated region (Albertsen, et al., 1993; Albertsen, et al., 1995). The Ms45 gene includes four exons with three introns that are removed by splicing. Expression of the MS45 protein encoded by the Ms45 gene in the anther tapetum is required for the production of fertile male pollen by the maize plant (Cigan, et al., 2001). The full-length MS45 protein is comprised of 412 amino acids and has a molecular weight of approximately 47 kDa (SEQ ID NO: 20). The expression of the Ms45 gene is controlled by the maize anther-specific 5126 promoter (Cigan and Albertsen, 1997). The terminator for the Ms45 gene is the endogenous Ms45 3' untranslated region sequence from the maize genome, which is included in the Ms45 Genomic sequence (Albertsen, et al., 1993).

The second cassette contains a truncated maize α-amylase (zm-aa1) gene that encodes the ZM-AA1 protein. The zm-aa1 coding region is preceded by the transit peptide from the maize Brittle-1 (zm-bt1) gene (Sullivan, et al., 1991) that targets the ZM-AA1 protein to the amyloplast. The ZM-AA1 protein prevents accumulation of starch in the nascent pollen grain, thus preventing the pollen from developing and germinating normally. The complete translation product, including transit peptide, comprises 495 amino acids and has a molecular weight of approximately 54 kDa (SEQ ID NO: 21). The processed ZM-AA1 protein with the transit peptide removed is 420 amino acid residues in length and has a molecular weight of approximately 46 kDa. The processed ZM-AA1 protein differs from the native protein in that it lacks the 21 N-terminal amino acid residues found in the native protein, including the initial methionine residue. The expression of the zm-aa1 gene and attached transit peptide is controlled by the Pg47 promoter, which is the 5' regulatory region from the maize pollen-specific polygalacturonase (Pg47) gene (Allen and Lonsdale, 1993). The terminator for the zm-aa1 gene is the 3' terminator sequence from the maize In2-1 gene (Hershey and Stoner, 1991).

The third cassette contains the DsRed2(Alt1) gene. The DsRed2(Alt1) gene is a modified version of the original DsRed2 gene (*Clontechniques*, 2001) in which an internal BstE II restriction site was removed without altering the amino acid sequence of the expressed protein. The DsRed2 (Alt1) coding sequence is provided at SEQ ID NO: 35. The DsRed2 (Alt1) gene encodes the DsRed2 protein. Expression of the DsRed2 protein in the aleurone layer of the maize seed produces a red coloration in seeds containing the DNA insertion, allowing for differentiation of seed containing event DP-32138-1 during seed sorting. The full-length DsRed2 protein has a length of 225 amino acids and a molecular weight of approximately 26 kDa (SEQ ID NO: 33). The expression of the DsRed2(Alt1) gene is controlled by the barley lipid transfer protein (Ltp2) promoter, which provides aleurone-specific transcription of the gene (Kalla, et al., 1994). Located 5' to the Ltp2 promoter is the enhancer region from the cauliflower mosaic virus (CaMV 35S enhancer) (Franck, et al., 1980; Odell, et al., 1985). The terminator for the DsRed2(Alt1) gene is the 3' terminator sequence from the proteinase inhibitor II gene of *Solanum tuberosum* (pinII terminator) (Keil, et al., 1986; An, et al., 1989).

Southern Blot Analysis of Event 32138—Methods

Southern blot analysis was conducted on DP-32138-1 maize to confirm insertion copy number and integrity and to generate a physical restriction enzyme map of the insertion. Genomic DNA samples from individual plants of DP-32138-1 maize were analyzed by digestion with the restriction enzymes BamH I, Bgl II, Bmt I, EcoR I, Hind III and Xho I, and double digestions with BamH I/Hind III and Bgl II/Hind III. These digests were hybridized to probes to the Ms45 Genomic region and the zm-aa1 and DsRed2(Alt1) genes, along with the remaining genetic elements in the T-DNA including the 5126 promoter, Pg47 promoter, zm-bt1 transit peptide, In2-1 terminator, CaMV 35S enhancer, Ltp2 promoter, and pinII terminator. Analysis with Bmt I and Xho I, examining sites in the bordering genome, indicated a single copy of the PHP24597 T-DNA is present in DP-32138-1 maize. The EcoR I analysis indicated that the PHP24597 T-DNA had inserted intact in the genome, as the internal EcoR I restriction sites were present. Analysis with the remaining enzymes was used in conjunction with these data to create a physical restriction map of the T-DNA insertion in DP-32138-1 maize.

Test Substances

The test substances in this study were defined as T1S1 red seed of DP-32138-1 maize, PHI log number T-F-07-132C. All seed were obtained from Pioneer Hi-Bred International, Inc. (Pioneer, Johnston, Iowa) and pedigree information is on file with staff breeders. The test substance seed used in this study were selected from a segregating population by their red color to ensure that they contained the DP-32138-1 event.

Control Substances

The control substances were defined as seed from maize lines that are not genetically modified. The unmodified lines have genetic backgrounds representative of the test substance background; however, they do not contain the DP-32138-1 insertions. All seed were obtained from Pioneer and pedigree information is on file with staff breeders.

| PHI Log # | Description |
| --- | --- |
| C-F-07-69C | 705 |
| PHIS01-70C | Hi-II |
| C-F-04-98C | Hi-II |
| C-F-07-131C | Hi-II(ms45) (Hi-II line homozygous for ms45 gene) |

Reference Substances

Plasmid PHP24597 was used as a positive control for Southern analysis to verify probe hybridization and to confirm the sizes of fragments internal to the inserted T-DNA. The plasmid DNA used was prepared from plasmid stocks obtained from Pioneer. The plasmid stocks were copies of the plasmid used for transformation to produce DP-32138-1 maize and were digested with restriction enzymes to confirm the plasmid map. The probes used in this study were derived from this plasmid or from a plasmid containing equivalent genetic elements.

DNA molecular weight markers for gel electrophoresis and Southern blot analysis were used to determine approximate molecular weights and amounts of DNA fragments. For Southern analysis, DNA Molecular Weight Marker VII, digoxigenin (DIG) labeled (Roche, Indianapolis, Ind.), was used as a size standard for hybridizing fragments. ΦX174 RF DNA/Hae III Fragments were used to determine sufficient migration on the agarose gel for Southern analysis. Low Mass DNA Ladder (Invitrogen, Carlsbad, Calif.) was used as an approximate quantitation standard.

Sample Collection

Ten seeds each of T-F-07-132C, C-F-07-131C and C-F-07-69C were planted in the Regulatory Science growth chambers at the DuPont Experimental Station (Wilmington, Del.) to produce plant tissue for extraction and analysis. One seed was planted per pot, and the pot was uniquely identified with study number, plant identifier, initials of the person who planted the seeds, and planting date. All plants were grown with light, temperature, and water regulated for healthy plant growth.

The first leaf harvest of the plants occurred when the plants were very small (V2-V3 leaf stage). For each of the control and test substance plants, sufficient leaf material from above the growing point was collected and placed directly into Geno/Grinder™ tubes (SPEX CertiPrep, Inc., Metuchen, N.J.) on dry ice. The samples were then transferred to a freezer and were maintained frozen (<−50° C.) until processing. The second and third leaf collections occurred after the plants had re-grown sufficiently and prior to the R1 stage; the youngest leaf was collected and placed in a pre-labeled, re-sealable bag. The sampling bags were placed directly on dry ice. The samples were then transferred to a freezer and were maintained frozen (<−50° C.) until processing. Frozen leaf tissue of Hi-II control maize plants was obtained from previous internal studies. All leaf samples were uniquely labeled with the plant identifier, date of harvest, study number, and initials of the harvester.

Event-Specific PCR Analysis

DNA was extracted from each leaf sample using the Extract-N-Amp™ Plant PCR kit using the described procedure (Sigma-Aldrich, St. Louis, Mo.). Real-time PCR was performed on each DNA sample utilizing an ABI PRISM® 7500 Fast Real-Time PCR System (Applied Biosystems, Inc., Foster City, Calif.). TaqMan® probe and primer sets were designed to detect a target sequence from the DP-32138-1 event. In addition, a second TaqMan® probe and primer set for a reference maize endogenous gene was used to confirm the presence of amplifiable DNA in each reaction. The analysis consisted of quantitative real-time PCR determination of qualitative positive/negative calls. The extracted DNA was assayed using optimized and validated primer and probe concentrations in TaqMan® Universal PCR Master Mix, No AmpErase® UNG (Applied Biosystems, Inc.). Initial incubation was at 95° C. for 10 minutes followed by 40 cycles as follows: 95° C. for 15 seconds, 60° C. for 1 minute.

Positive or negative determination for the event was based on comparison of the $C_T$ (threshold cycle) of the insertion target PCR to that of the maize endogenous reference target. If the event and endogenous PCR targets amplified above $C_T$ threshold, then the plant was scored as positive for that event. If the endogenous target amplified and the event target did not, then the plant was scored as negative. If neither target amplified for a particular sample, then it was determined to be a poor quality sample or failed run and the assay was repeated.

DNA Extraction and Quantitation

Genomic DNA was extracted from leaf tissue of test and control plants. The tissue was pulverized in tubes containing grinding beads using a Geno/Grinder™ (SPEX CertiPrep, Inc.) instrument and the genomic DNA isolated using a standard Urea Extraction Buffer procedure. Following extraction, the DNA was quantified on a spectrofluorometer using Pico Green® reagent (Molecular Probes, Inc., Eugene, Oreg.) and visualized on an agarose gel to confirm values from Pico Green analysis and to determine the DNA quality.

Digestion of DNA and Electrophoretic Separation

For characterization of the DP-32138-1 insertion, genomic DNA samples extracted from both test and control plants were digested with BamH I, Bgl II, Bmt I, EcoR I, Hind III and Xho I or a combination of two restriction enzymes: BamH I/Hind III and Bgl II/Hind III (New England Biolabs, Ipswich, Mass.).

Following digestion with the restriction enzyme, the fragments produced were electrophoretically separated by size through an agarose gel and a molecular weight standard [ΦX174 RF DNA/Hae III Fragments (Invitrogen)] was used to determine sufficient migration and separation of the fragments on the gel.

Southern Transfer

Agarose gels containing the separated DNA fragments were depurinated, denatured, and neutralized in situ, and transferred to a nylon membrane in 20×SSC buffer using the method as described for the TURBOBLOTTER™ Rapid Downward Transfer System (Schleicher and Schuell, Keene, N. H.). Following transfer to the membrane, the DNA was bound to the membrane by UV crosslinking (Stratalinker, Stratagene, La Jolla, Calif.).

Probe Labeling and Southern Blot Hybridization

The DNA fragments bound to the nylon membrane were detected as discrete bands when hybridized to a labeled probe. Probes used for Southern hybridization are provided in Table 1 and their locations shown in FIG. 2. Probes for the Ms45 Genomic region, zm-aa1 gene, DsRed2(Alt1) gene, 5126 promoter, Pg47 promoter, Ltp2 promoter, zm-bt1 transit peptide, In2-1 terminator, pinII terminator and CaMV 35S enhancer elements were used for Southern hybridization. A probe containing the zm-bt1 transit peptide combined with the zm-aa1 gene (zm-bt1-aa1 probe) was used for preliminary Southern blot analysis instead of separate probes for the two elements. Fragments of the elements were generated by PCR from plasmid PHP24597 using specific primers and were gel purified (Qiagen, Valencia, Calif.). With the exception of the Pg47 promoter, each probe covered the majority of the respective genetic element, with only small regions left out due to requirements imposed by the PCR labeling procedure. DNA probes were generated from these fragments by PCR that incorporated a digoxigenin (DIG) labeled nucleotide, [DIG-11]-dUTP, into the fragment. PCR labeling of isolated fragments was carried out according to the procedures supplied in the PCR DIG Probe Synthesis Kit (Roche).

Labeled probes were hybridized to the target DNA on the nylon membranes for detection of the specific fragments using the procedures essentially as described for DIG Easy Hyb solution (Roche). DIG labeled DNA Molecular Weight Marker VII (Roche), visible after DIG detection as described below, was used to determine hybridizing fragment size on the Southern blots.

Detection of Hybridized Probes

DIG-labeled probes, hybridized to DNA bound to the nylon membrane after stringent washes, and DIG-labeled DNA standards were visualized using CDP-Star Chemiluminescent Nucleic Acid Detection System with DIG Wash and Block Buffer Set (Roche). Blots were exposed to X-ray film for one or more time points to detect hybridizing fragments and to visualize molecular weight standards. Images were digitally captured by detection with the Luminescent Image Analyzer LAS-3000 (Fujifilm Medical Systems, Stamford, Conn.). Digital images were compared to original X-ray film exposures as verification for use in this report. The sizes of detected bands were documented for each digest and each probe.

Stripping of Probes and Subsequent Hybridizations

Following hybridization and detection, membranes were stripped of DIG-labeled probe to prepare the blot for subsequent re-hybridization to a different probe. Membranes were rinsed briefly in distilled, de-ionized water and then stripped in a solution of 0.2 M NaOH and 0.1% SDS at 37° C. with constant shaking. The membranes were then rinsed in 2×SSC and either used directly for subsequent hybridizations or stored for later use. The alkali-based stripping procedure effectively removes probes labeled with the alkali-labile DIG used in these experiments.

Southern Blot Analysis of Event 32138—Results and Discussion

Genotype Confirmation and Preliminary Southern Blot Analysis of T1S1 Maintainer Plants of DP-32138-1

All individual plants were tested for the presence of the DP-32138-1 insertion by event-specific PCR analysis. All ten DP-32138-1 T1 S1 plants were positive for the insertion. The results of the event-specific PCR assays for the DP-32138-1 plants are summarized in Table 2. All control plants tested negative for the DP-32138-1 insertion (data not shown). The results of the event-specific PCR analysis substantiate the visual screen of the seeds. Furthermore, these event-specific PCR results also verify that the Left Border of the PHP24597 T-DNA insertion remains stable in plants containing the DP-32138-1 insertion.

Genomic DNA extracted from ten individual DP-32138-1 plants and 21 control plants (ten Hi-II(ms45) plants, ten 705 plants, and one Hi-II plant) was analyzed by preliminary Southern blots for the presence of the Ms45 Genomic, zm-bt1-aa1 and DsRed2(Alt1) genetic elements. DNA from these plants was digested with EcoR I or BamH I, blotted, and probed with the Ms45, zm-bt1-aa1 and DsRed2 probes. Results from these Southern blots correspond directly with the results of the event-specific PCR assays. All DP-32138-1 plants contained the Ms45 Genomic, zm-bt1-aa1, and DsRed2(Alt1) genetic elements (Table 2) and the control plants were negative for the genes (data not shown). This preliminary Southern blot analysis also indicated that the inserted DNA was identical in all DP-32138-1 plants, as the banding pattern with each probe was identical for all plants. Because control plant samples within a particular inbred line had differing hybridization patterns, these blots were also used to select controls for the Southern blot analysis described below and confirmed controls selected would account for all bands due to the endogenous genome. Hybridization of the same blots with a probe for the zm-bt1-aa1 coding sequence resulted in many overlapping endogenous bands that were also seen in the control plants. This probe was split into separate zm-bt1 and zm-aa1 probes for use in the detailed characterization of a subset of DNA samples in this study as described below.

Detailed Southern Blot Analysis of DP-32138-1

A total of six restriction enzymes were selected to use in a detailed Southern blot analysis of DP-32138-1 maize: BamH I, Bgl II, Bmt I, EcoR I, Hind III and Xho I, which are shown on the PHP24597 T-DNA map (FIG. 2). In addition, double digests with BamH I/Hind III and Bgl II/Hind III were utilized for Southern analysis. The locations of the BamH I and EcoR I restriction sites are shown on the plasmid map of PHP24597 (FIG. 1) and the base pair locations of restriction sites for enzymes used in the analysis are given in Table 1.

PHP24597 was added to 705 maize control DNA, digested, and included on the blots to provide both a positive control for probe hybridization and a size reference for DNA fragments that are contained completely within the T-DNA. Table 1 and Table 18 provide further information on the probes used.

The schematic map of plasmid PHP24597 (FIG. 1) indicates restriction enzyme sites for BamH I and EcoR I and the Ms45, zm-aa1 and DsRed2 coding regions. Left Border and Right Border flack the T-DNA (FIG. 2) that is expected to be inserted during Agrobacterium-mediated transformation. Plasmid size is 52869 bp. The locations of additional enzymes used in this study are given below:

| Enzyme | Locations (bp) |
|---|---|
| Bgl II | 1713, 2519, 7030, 38258, 41055, 42018, 45737, 46167, 49645 |
| Bmt I | 8503, 36160, 38359, 39502, 45917 |
| Hind III | 179, 34837, 45900, 46809, 47930, 49445 |
| Xho I | 2134, 5587, 34814, 36128, 37028, 37074, 37711, 45532 |

The schematic map of the T-DNA region of Plasmid PHP24597 (FIG. 2) indicates restriction enzyme sites for BamH I, Bgl II, BmtI, EcoR I, Hind III and Xho I and the Ms45, zm-aa1 and DsRed2 coding and regulatory regions. The locations of enzymes used in this study are given below:

| Enzyme | Locations (bp) |
|---|---|
| BamH I | 1456, 4271, 6773, 8792 |
| Bgl II | 1713, 2519, 7030 |
| Bmt I | 8503 |
| EcoR I | 191, 7407, 9869 |
| Hind III | 179 |
| Xho I | 2134, 5587 |

Each restriction digest was hybridized with ten different probes covering the genetic elements within the PHP24597 T-DNA: Ms45, zm-bt1, zm-aa1 and DsRed2, and probes for the regulatory regions 5126 promoter, Pg47 promoter, In2-1 terminator, 35S enhancer, Ltp2 promoter, and pinII terminator. Detailed descriptions of all probes are provided in Table 1 and the locations of the probes are shown on the T-DNA map (FIG. 2). Each of these probes hybridizes to only one element within the T-DNA. The actual number of hybridizing bands for each probe depends on the location of the specific enzyme restriction sites in relation to the genetic element and ranges from one to three bands for a single insertion of the PHP24597 T-DNA with the enzymes used in this study.

Two types of fragments would be observed from these digests and hybridizations: a) border fragments, where an enzyme site is located within the PHP24597 T-DNA at one end of the hybridizing fragment and a second enzyme site is expected in the maize genome and b) internal fragments where known enzyme sites flank the probe region and the fragments are completely contained within the PHP24597 T-DNA. Border fragment sizes are unique for each event and provide a means to demonstrate the number of copies of a particular element based on the number of bands observed. One hybridizing band produced from an enzyme that cleaves once in the insert, outside of the probe region, indicates the presence of one copy of the inserted T-DNA at a single locus in the genome. Border fragments formed from the insertion of a full-length T-DNA are typically larger than the size predicted from the T-DNA sequence due to the inclusion of genomic DNA in the fragment. The exact size of border fragments cannot be predicted in advance due to the unknown location of the cleavage site in the maize genome. Internal fragments provide a means to assess the integrity of the inserted T-DNA and that it has not been changed from the intended arrangement.

The Southern blot data were used to generate a restriction map of the DP-32138-1 T-DNA insertion (FIG. 3). BamH I, Bgl II, Bmt I, EcoR I, Hind III and Xho I restriction enzyme sites are indicated. Southern blot analysis indicated a single copy of the PHP24597 T-DNA had inserted within the maize genome. Locations of enzyme sites outside the T-DNA region are not to scale. An asterisk (*) indicates that the relative locations of these enzyme sites are uncertain due to the large size of the fragments generated from these sites. Dashed vertical lines indicate the BamH I and Bgl II sites located outside the Left Border junction that demonstrated blocked digestion on the Southern blots.

The Ms45, zm-bt1, zm-aa1, 5126 promoter, Pg47 promoter, and In2-1 terminator probes used in this study are derived from endogenous maize genomic DNA sequences. As a result, Southern blots with these probes also exhibited a number of bands that were due to hybridization to the endogenous sequences in addition to the bands due to the DP-32138-1 insertion. These bands were confirmed by their presence in one or more of the control plant lines (705, Hi-II, or Hi-II(ms45)). The DP-32138-1 generation utilized in this study (T1S1) was derived from the original transformant of the Hi-II(ms45) background (Hi-II with a backcrossed ms45 allele), crossed to 705, and then self-crossed. Thus, the T1S1 plants exhibited endogenous bands derived from both the Hi-II and 705 control lines, which varied between T1S1 individuals depending on the digest and probe used. In addition, some of the hybridizing bands showed differences between plants within the Hi-II and Hi-II(ms45) control lines themselves, thus requiring the inclusion of two plants from each of these control lines on some of the Southern blots in order to account for all of the endogenous bands observed in the DP-32138-1 plants.

With the exception of the Pg47 promoter, each probe covers the majority of the respective genetic element, with only small regions left out due to requirements imposed by the PCR labeling procedure. In the case of the Pg47 promoter, test hybridizations with probe fragments encompassing the approximately 2.7 kb element resulted in intense hybridization to all lanes containing genomic DNA. The full-length Pg47 promoter probe tested but not used in the study, as described herein, is shown as a solid line below the Pg47 promoter element in the map of FIG. 2. Further investigation yielded a 424 bp fragment located at the 3' end of the Pg47 promoter that hybridized to a reduced number of endogenous bands and thus provided usable information about this element in DP-32138-1 maize.

Copy Number of Inserted DNA in DP-32138-1 Maize

The restriction enzymes Bmt I and Xho I were selected to confirm the number of copies of the PHP24597 T-DNA inserted in DP-32138-1 maize.

Bmt I has a single restriction site located within the T-DNA and will result in border fragments at the Right and Left Borders for each single insertion of the T-DNA depending on the probe used (FIG. 2). The site for Bmt I is located at by 8503 within the T-DNA, and would be expected to yield fragments of greater than about 8500 bp and greater than about 1400 bp for a single inserted T-DNA. The fragment of greater than 8500 bp will hybridize to the 5126 promoter, Ms45, Pg47 promoter, zm-bt1, zm-aa1, In2-1 terminator, 35S enhancer, and Ltp2 promoter probes, while the fragment of greater than 1400 bp will hybridize to the Ltp2 promoter, DsRed2, and pinII terminator probes. Since the Bmt I site is located within the Ltp2 promoter element, hybridizing with this probe would allow both fragments to be visible simultaneously on a Southern blot.

In the Bmt I Southern analysis, a band of greater than 8600 bp hybridized in DP-32138-1 maize with the 5126 promoter, Ms45, zm-bt1, zm-aa1, In2-1 terminator, 35S enhancer, and Ltp2 promoter probes (Table 3). In addition, endogenous bands were observed in all samples with the 5126 promoter, Ms45, zm-bt1, zm-aa1, and In2-1 terminator probes. A band of greater than 8600 bp was also observed with the Ltp2 promoter, DsRed2, and pinII terminator probes (Table 3), which can be identified as the larger of the two bands seen with the Ltp2 promoter probe by comparison with the pinII terminator and 5126 promoter hybridizations. No specific band can be identified with the Pg47 promoter on the Bmt I blot due to the intensity of the co-migrating endogenous bands. However, the presence of the greater than 8600 bp band with the probes flanking the Pg47 promoter element (Ms45 and zm-bt1) indicates the Pg47 promoter band is likely to be located in the region of the blot obscured by endogenous bands above the 8600 bp marker. Furthermore, based on the Xho I analysis discussed below, a single copy of the Pg47 element was determined to be inserted in DP-32138-1 maize.

Xho I has two restriction sites located within the PHP24597 T-DNA (FIG. 2), and would be expected to produce one internal fragment and two border fragments at the Right and Left Borders for each single insertion. The two restriction sites are located at by positions 2134 and 5587 (FIG. 2). Digestion with this enzyme will produce three fragments from a single T-DNA insertion: a border fragment of greater than about 2100 bp that hybridizes to the 5126 promoter and Ms45 probes, an internal fragment of 3453 bp that hybridizes to the Ms45, Pg47 promoter, and zm-bt1 probes, and a second border fragment of greater than about 4400 bp that hybridizes to the zm-bt1, zm-aa1, In2-1 terminator, 35S enhancer, Ltp2 promoter, DsRed2 and pinII terminator probes.

Hybridization of Xho I-digested DNA from DP-32138-1 maize with the 5126 promoter probe resulted in a single band of about 3600 bp from the T-DNA insertion, in addition to two bands resulting from endogenous maize sequences (Table 4). Hybridization to the Ms45 probe resulted in two bands as expected: the approximately 3600 bp border band also seen with the 5126 promoter probe and an internal band matching the 3453 bp plasmid fragment (Table 4). The same 3453 bp internal fragment was observed with the Pg47 promoter probe (Table 4). The PHP24597 plasmid band is weak in many of the hybridizations, but can be observed on the films of the Southern blots. The zm-bt1 probe showed two insert-derived bands as expected from the location of the Xho I site within the element: the 3453 internal band seen with the Ms45 and Pg47 promoter probes and a border band of greater than 8600 bp (Table 4). Endogenous bands were again observed with the Ms45, Pg47 promoter, and zm-bt1 probes. The greater than 8600 bp border band was also seen in hybridizations with the In2-1 terminator (Table 4), 35S enhancer and Ltp2 promoter (Table 4), and DsRed2, and pinII terminator (Table 4) probes. Endogenous bands were observed with the In2-1 terminator probe. No extra insert-derived bands were seen with any of these probes. Hybridization of the Xho I-digested DNA with the zm-aa1 probe did not provide any information about the DP-32138-1 insertion, as the region in which the expected greater than 8600 bp band is located, as shown by the flanking zm-bt1 and In2-1 probes, was obscured by intense endogenous bands. However, since the zm-bt1 and In2-1 probes hybridized to the same greater than 8600 bp band that was observed with the probes of the DsRed2 cassette and, as described above in the Bmt I analysis, a single band hybridized to the zm-aa1 probe, a single copy of the zm-aa1 gene was determined to be inserted in DP-32138-1 maize.

Therefore, Southern analysis of DP-32138-1 with Bmt I and Xho I digestion demonstrates that there is a single copy of the T-DNA insertion within the maize genome. Except for those elements in which the restriction site is located within the element, there are only single bands for each of the genetic elements, as expected for fragments from a single copy insertion. The elements in the T-DNA that contain the restriction sites also show the expected number of bands, based on the restriction enzyme location, for a single copy insertion. The presence of single border bands, and no extra insert-derived bands, demonstrates that there is only a single copy of the PHP24597 T-DNA within the DP-32138-1 maize genome.

Integrity of Inserted DNA in DP-32138-1 Maize

The restriction enzyme EcoR I was used to confirm the integrity of the PHP24597 T-DNA insertion. This enzyme has three restriction sites within the PHP24597 T-DNA: one site located between the Right Border and the 5126 promoter element at by position 191, one site between the pinII terminator region and the Left Border at by position 9869, and a third site located between the In2-1 terminator and the CaMV 35S enhancer element at by position 7407 (FIG. 2). Digestion with EcoR I should produce two internal fragments, of 7216 bp and 2462 bp, from both the PHP24597 plasmid control and plants containing an intact T-DNA insertion. The band observed will depend on the probe used on a given Southern blot. Hybridization with the 5126 promoter, Ms45, Pg47 promoter, zm-bt1, zm-aa1, and In2-1 terminator probes will result in the 7216 bp band, while the 35S enhancer, Ltp2 promoter, DsRed2, and pinII terminator probes will hybridize to the 2462 bp band. The presence of the appropriate band with a given probe and absence of any other insert-derived band for that probe provides a strong indication that the T-DNA is complete and was not truncated upon insertion.

Hybridization of the EcoR I digested DNA with the 5126 promoter and Ms45, probes resulted in a single insert-derived band of 7216 bp that matched the internal plasmid band (Table 5). The same band of 7216 bp was observed with the Pg47 promoter and zm-bt1 probes (Table 5) and the zm-aa1 and In2-1 terminator probes (Table 5). The 7216 bp band was somewhat obscured on the zm-aa1 blot by the presence of hybridizing bands due to the maize endogenous background and could not be confirmed. This element was determined to be inserted intact based on analysis discussed below with BamH I and Bgl II, because digestion with these enzymes released an internal fragment from the T-DNA of the appropriate size. Furthermore, each of these analyses showed only the expected internal fragment and no other bands due to the DP-32138-1 insertion. In addition, there were a number of bands due to hybridization of endogenous maize sequences with the 5126 promoter, Ms45, Pg47 promoter, zm-bt1, zm-aa1, and In2-1 terminator probes, that are indicated in Table 5 by an asterisk (*) and gray shading. The 7216 bp band was observed to have run on the gel at an apparent molecular size slightly below the expected size when hybridized to these probes in both the plasmid lanes and the DP-32138-1 maize lanes. This anomalous size appears to be specific to this fragment, as the 2462 bp EcoR I fragment ran at the expected size in comparison to the molecular weight markers. There may be a shift in electrophoretic mobility of the 7216 bp fragment due to the presence of the control maize DNA sample causing it to exhibit an apparent size on the gel somewhat smaller than the actual size. The insert-derived band of 2462 bp was observed with the 35S enhancer and Ltp2 promoter probes (Table 5) and the DsRed2 and pinII terminator probes (Table 5). No other bands specific to the DP-32138-1 plants were observed in these Southern blots. Table 5 summarizes the expected and observed bands on the EcoR I blots.

The EcoR I blots demonstrate that the PHP24597 T-DNA in DP-32138-1 is intact, as only the expected two bands of 7216 bp and 2462 bp are observed with their respective probes. The two fragments comprise the entire PHP24597 T-DNA with the exception of the small regions between the EcoR I sites near the ends of the T-DNA and the Left and Right Border elements. The presence of the only two expected bands, and the absence of other bands specific to the DP-32138-1 plants, indicates that the PHP24597 T-DNA inserted intact in the maize genome.

Physical Map of Inserted DNA in DP-32138-1 Maize

Three additional restriction enzymes were chosen to provide a complete analysis of the DP-32138-1 insertion: Hind III, BamH I and Bgl II. Digests with each of these enzymes were hybridized to the ten probes used on the preceding blots and the information derived from these hybridizations was combined with the data described above to create a detailed restriction map of the T-DNA insertion and the surrounding maize genomic DNA in DP-32138-1 (FIG. 3). Additional double digestions were carried out with BamH I/Hind III and Bgl II/Hind III to clarify parts of the insertion as seen with the BamH I and Bgl II single digests.

There is one Hind III site in the PHP24597 T-DNA, located between the Right Border and the 5126 promoter at by 179 (FIG. 2). All of the probes used in this study would hybridize to a single border fragment of greater than about 9800 bp (Table 6).

Hybridization of Hind III digested DNA from DP-32138-1 with the probes used in this study yielded a single insert-derived band of greater than 8600 bp, with the exception of the Pg47 promoter probe (Table 6). In addition to the insert-derived bands, endogenous hybridization was observed in the Hind III digests with the 5126 promoter, Ms45, Pg47 promoter, zm-bt1, zm-aa1, and In2-1 terminator probes, that are indicated in Table 6 by an asterisk (*) and gray shading. In the case of the Pg47 promoter probe, the insert-derived band was obscured by a series of very intense endogenous bands above the 8600 bp molecular weight marker. However, as there were no other bands present in the DP-32138-1 plants that could be determined to be from the insert, and the flanking Ms45 and zm-bt1 probes both hybridized to the same greater than 8600 bp band, it is likely that the Pg47 promoter probe band is indeed of the size expected from the other hybridizations but is merely masked by the endogenous bands. As discussed above for the Xho I and EcoR I analysis with the Pg47 probe, a single intact copy of this element was determined to be inserted in DP-32138-1 maize. As the upper molecular weight marker is 8600 bp, and the Hind III band is located above the marker band, the exact size of the Hind III band cannot be determined, although it appears large enough to exceed its minimum expected size of 9800 bp. Additional data, as discussed below in the Hind III double digestions, show that the Hind III site in the genome is located approximately 1200 to 1400 bp away from the Left Border of the DP-32138-1 insertion providing evidence that the insertion is intact from base pair position 179.

There are four restriction sites for BamH I within the PHP24597 T-DNA, located at by positions 1456, 4271, 6773 and 8792 (FIG. 2). Digestion with this enzyme will result in five expected fragments for a single T-DNA insertion: a border fragment of greater than about 1500 bp that hybridizes to the 5126 promoter and Ms45 probes, an internal fragment of 2815 bp that hybridizes to the Ms45 probe, an internal fragment of 2502 bp that hybridizes to the Pg47 promoter, zm-bt1 and zm-aa1 probes, a third internal fragment of 2019 bp that would hybridize to the zm-aa1, In2-1, 35S enhancer and Ltp2 promoter probes and a second border fragment of greater than about 1200 bp that hybridizes to the DsRed2 and pinII terminator probes (Table 7). Although the BamH I site at by location 4271 is located within the Pg47 promoter element, and thus a full Pg47 promoter probe would hybridize to both the 2815 and 2502 bp fragments, only the 2502 bp fragment would be seen with the 424 bp Pg47 promoter probe that was used in this study due to its location at the 3' end of the element (Table 7).

A band of about 3800 bp was observed upon hybridization of BamH I-digested DNA from DP-32138-1 with the 5126 promoter and Ms45 probes (Table 7). The expected 2815 bp internal band was also observed with the Ms45 probe (Table 7). Hybridization with the Pg47 promoter, zm-bt1 and zm-aa1 probes resulted in a band of 2502 bp that matched the plasmid control band (Table 7). The zm-aa1 probe also hybridized to an internal band of 2019 bp that matched the plasmid band, as did the In2-1 terminator, 35S enhancer, and Ltp2 promoter probes (Table 7). Endogenous bands were observed with all probes in the Ms45 and zm-aa1 cassettes. Two border bands were observed with the DsRed2 and pinII terminator probes: a strongly hybridizing band of about 4600 bp and a very faint band of about 6100 bp (Table 7). Table 7 gives the expected and observed bands seen with this digest. In order to investigate the possibility that the faint 6100 bp band resulted from blocked digestion of the genomic BamH I site that resulted in the 4600 bp band, a double digestion with BamH I/Hind III was performed as described below.

To demonstrate that the faint second band of about 6100 bp seen with the BamH I digest and the DsRed2 and pinII terminator probes was due to blocked digestion at the BamH I site in the maize genome, a double digest was performed with BamH I and Hind III. Hind III was selected due to the location of its restriction site in the maize genome close to the Left Border junction of the DP-32138-1 insertion as described above. Digestion with these two enzymes should yield a border fragment of greater than 1200 bp from the BamH I site located at by 8792 in the T-DNA and the Hind III site in the maize genome. As the Hind III site appears to be located closer to the Left Border than the genomic BamH I site, digestion with both enzymes should release a single, unique fragment hybridizing to the DsRed2 and pinII terminator probes from a single T-DNA insertion. The presence of only a single band with the double digest would provide evidence that the faint second band of about 6100 bp on the BamH I Southern blot did result from blocked cleavage at the genomic BamH I site responsible for the approximately 4600 bp band. However, if two bands are again observed with the double digestion and these two probes, it would be evidence that there is more than one copy of the elements.

Hybridization of BamH I/Hind III digested maize DNA with the DsRed2 and pinII terminator probes resulted in a single band of about 2600 bp in the DP-32138-1 plants and no other bands (Table 8). This 2600 bp fragment is smaller than the approximately 4600 bp fragment observed in the BamH I analysis and, thus, the location of the genomic Hind III site can be estimated to be approximately 1400 bp away from the Left Border junction and is located between the Left Border and the genomic BamH I site. The lack of any other bands with the double digestion demonstrates that there is only one copy of this region of the PHP24597 T-DNA in the DP-32138-1 genome. Furthermore, this indicates the faint band of about 6100 bp seen with the BamH I digest is indeed due to blocked cutting by this enzyme at the restriction site located closest to the Left Border junction in the maize genome. One possible explanation for the blocked cleavage at this BamH I site is methylation of the restriction site or adjoining DNA sequence that results in lowered efficiency of digestion by BamH I (Brown, 1998). Hybridizations of the BamH I/Hind III digested maize DNA to the remaining probes used to characterize DP-32138-1 maize all showed the expected bands based on the PHP24597 T-DNA map.

Bgl II has three restriction sites within the PHP24597 T-DNA, located at by positions 1713, 2519 and 7030 (FIG. 2). Digestion of the inserted T-DNA with Bgl II will yield four fragments: a border fragment of greater than about 1700 bp hybridizing to the 5126 promoter and Ms45 probes, an internal fragment of 806 bp that hybridizes to the Ms45 probe, another internal fragment of 4511 bp hybridizing to the Ms45, Pg47 promoter, zm-bt1 and zm-aa1 probes and a third border fragment of greater than about 2900 bp that hybridizes to the In2-1 terminator, 35S enhancer, Ltp2 promoter, DsRed2 and pinII terminator probes (FIG. 2).

All of the four bands expected with the various probes and Bgl II digested DNA from DP-32138-1 were seen on the Southern blots. The 5126 promoter and Ms45 probes both hybridized to a border band of about 3600 bp (Table 9). The Ms45 probe also hybridized to two internal bands of 806 bp and 4511 bp that correspond to the plasmid control bands (Table 9). The 4511 bp band is faint due to the small overlap of about 140 bp with the Ms45 probe, while the 806 bp band overlaps an endogenous band of about 800 bp, but can be detected by the increased intensity of the band compared to the control plant lanes. The 4511 bp internal band that matched the plasmid band was also detected using the Pg47 promoter, zm-bt1 and zm-aa1 probes (Table 9). The In2-1 terminator probe detected a strongly hybridizing border band of about 4900 bp (Table 9). As with the other digests, a number of endogenous bands of varying intensities were detected with all the probes of the Ms45 and zm-aa1 cassettes. Hybridization with the 35S enhancer, Ltp2 promoter, DsRed2, and pinII terminator probes resulted in the detection of two bands: a strongly hybridizing border band of about 4900 bp and a much fainter band of about 7400 bp (Table 9). It is likely that the 7400 bp band resulted from blocked digestion of the maize genomic DNA with Bgl II at the site that should result in the 4900 bp border band, and a double digestion with Bgl II/Hind III was performed as described below to test this hypothesis. Based on the map of the PHP24597 T-DNA (FIG. 2), it is likely that the 7400 bp band would also be detected with the In2-1 terminator probe, but it was not observed due to the weak hybridization to this band and the presence of endogenous bands in that region of the blot.

Similar to the BamH I/Hind III analysis described above, a double digest was performed with Bgl II and Hind III to demonstrate that the faint second band of about 7400 bp seen with the Bgl II digest and the 35S enhancer, Ltp2 promoter, DsRed2 and pinII terminator probes was due to blocked digestion at the Bgl II site in the maize genome. Digestion with these two enzymes and hybridization with the 35S enhancer, Ltp2 promoter, DsRed2 and pinII terminator probes should yield a border fragment of greater than 2900 bp from the Bgl II site located at by 7030 and the Hind III site in the maize genome. As the Hind III site appears to be located closer to the Left Border than the genomic Bgl II site, digestion with both enzymes should release a single, unique fragment hybridizing to these probes from a single T-DNA insertion. The presence of only a single band with the double digest would provide evidence that the faint second band of about 7400 bp on the Bgl II Southern blot did result form blocked cleavage at the genomic Bgl II site responsible for the approximately 4900 bp band. However, if two bands are again observed with the double digestion and these two probes, it would be evidence that there is more than one copy of the elements.

Hybridization of Bgl II/Hind III digested maize DNA with the 35S enhancer, Ltp2 promoter, DsRed2 and pinII terminator probes resulted in a single band of about 4100 bp in the DP-32138-1 plants (Table 10). This 4100 bp fragment is smaller than the approximately 4900 bp fragment observed in the Bgl II analysis and positions the genomic Hind III site between the Left Border junction and the Bgl II site, at approximately 1200 bp from the border. Additionally, the lack of any other insertion-related bands with the double digestion demonstrates that there is only one copy of this region of the PHP24597 T-DNA in the DP-32138-1 genome, and that the faint band of about 7400 bp seen with the Bgl II digest alone is likely due to blocked cutting by this enzyme at the site in the maize genome located closest to the Left Border junction. One possible explanation for the blocked digestion at this Bgl II site is methylation of the restriction site or adjoining DNA sequence that results in lowered efficiency of digestion by Bgl II (Brown, 1998). Hybridizations of the Bgl II/Hind III digested maize DNA to the remaining probes used to characterize DP-32138-1 maize all showed the expected bands based on the PHP24597 T-DNA map. The difference between the location of the genomic Hind III restriction site determined with the Bgl II/Hind III Southern blot (1200 bp from the Left Border) and the BamH I/Hind III analysis (1400 bp from the Left Border) is likely due to electrophoretic mobility shifts between Southern blots and the inherent inaccuracy of band size approximation based on the DIG VII markers used in this study.

The information obtained from the Hind III, BamH I, Bgl II, BamH I/Hind III, and Bgl II/Hind III digests was combined with the data derived from the Bmt I, Xho I, and EcoR I blots to generate a restriction map of the T-DNA insertion and the surrounding maize genome (FIG. 3). The digests and hybridizations are consistent with the presence of a single, intact PHP24597 T-DNA in the genome of DP-32138-1 maize.

Example 1

Conclusions

Southern blot analysis was conducted on DP-32138-1 maize to confirm insertion copy number and integrity and to generate a physical restriction enzyme map of the insertion. Genomic DNA samples from individual plants of DP-32138-1 maize were analyzed by digestion with the restriction enzymes BamH I, Bgl II, Bmt I, EcoR I, Hind III, and Xho I and double digestions with BamH I/Hind III and Bgl II/Hind III. These digests were hybridized to probes to the Ms45 Genomic region and the zm-aa1 and DsRed2(Alt1) genes, along with the remaining genetic elements in the T-DNA including the 5126 promoter, Pg47 promoter, zm-bt1 transit peptide, In2-1 terminator, CaMV 35S enhancer, Ltp2 promoter, and pinII terminator. Analysis with Bmt I and Xho I, examining sites in the bordering genome, indicated a single intact copy of the PHP24597 T-DNA is present in DP-32138-1 maize. The EcoR I analysis indicated that the PHP24597 T-DNA had inserted intact in the genome, as the internal EcoR I restriction sites were present. Analysis with the remaining enzymes was used in conjunction with these data to create a physical restriction map of the T-DNA insertion in DP-32138-1 maize.

TABLE 1

Description of DNA Probes Used for Southern Hybridization

| Probe Name | Probe Lot# | Genetic Element | Probe Position on PHP24597 T-DNA (bp to bp)[1] | Probe Position on PHP24597 Plasmid (bp to bp)[2] | Probe Length (bp) |
|---|---|---|---|---|---|
| 5126 promoter | 08-DP-5 | 5126 promoter | 304-706 | 304-706 | 403 |
| Ms45[3] | 08-DP-29 | Ms45Genomic | 707-1426 | 707-1426 | 720 |
| | 07-DP-29 | region | 1427-2258 | 1427-2258 | 832 |
| | 08-DP-33 | | 2263-2658 | 2263-2658 | 396 |
| Pg47 promoter | 08-DP-34 | Pg47 promoter (3' region) | 5028-5451 | 5028-5451 | 424 |
| zm-bt1 | 08-DP-12 | zm-bt1 transit peptide | 5469-5693 | 5469-5693 | 225 |
| zm-aa1[4] | 08-DP-32 | zm-aa1 gene | 5701-6333 | 5701-6333 | 603 |
| | 08-DP-7 | | 6334-6935 | 6334-6935 | 602 |
| zm-bt1-aa1[5] | 07-DP-34 | zm-bt1 transit peptide + zm-aa1 gene | 5469-6333 | 5469-6333 | 865 |
| | 08-DP-7 | | 6334-6935 | 6334-6935 | 602 |
| In2-1 terminator | 07-DP-33 | In2-1 terminator | 7049-7377 | 7049-7377 | 329 |
| 35S enhancer | 08-DP-8 | CaMV 35S enhancer region | 7427-7846 | 7427-7846 | 420 |
| Ltp2 promoter | 08-DP-16 | Ltp2 promoter | 7906-8759 | 7906-8759 | 854 |

TABLE 1-continued

Description of DNA Probes Used for Southern Hybridization

| Probe Name | Probe Lot# | Genetic Element | Probe Position on PHP24597 T-DNA (bp to bp)[1] | Probe Position on PHP24597 Plasmid (bp to bp)[2] | Probe Length (bp) |
|---|---|---|---|---|---|
| DsRed2 | 08-DP-11 | DsRed2(Alt1) gene | 8810-9487 | 8810-9487 | 678 |
| pinII terminator | 08-DP-6 | pinII terminator | 9582-9815 | 9582-9815 | 234 |

[1]The probe position is based on the PHP24597 T-DNA map (FIG. 2).
[2]The probe position is based on the PHP24597 plasmid map (FIG. 1).
[3]The Ms45 probe is comprised of three non-overlapping labeled fragments that are combined in the hybridization solution.
[4]The zm-aa1 probe is comprised of two non-overlapping labeled fragments that are combined in the hybridization solution.
[5]The zm-bt1-aa1 probe is comprised of two non-overlapping labeled fragments that are combined in the hybridization solution. This probe was used for the preliminary Southern blot analysis only.

TABLE 2

Results of Event-Specific Polymerase Chain Reaction Analysis and Preliminary Southern Blot Analysis of Plants Grown from Test Substance Seed

| Plant ID Number | Sample ID (Event/Sample #) | Polymerase Chain Reaction Assay Results for Event DP-32138-1[1] | Preliminary Southern Blot Results with Ms45 Probe[2] | Preliminary Southern Blot Results with zm-bt1-aa1 Probe[2] | Preliminary Southern Blot Results with DsRed2 Probe[2] |
|---|---|---|---|---|---|
| T-F-07-132C-1 | DP-32138-1/T1 | Positive | Positive | Positive | Positive |
| T-F-07-132C-2 | DP-32138-1/T2 | Positive | Positive | Positive | Positive |
| T-F-07-132C-3 | DP-32138-1/T3 | Positive | Positive | Positive | Positive |
| T-F-07-132C-4 | DP-32138-1/T4 | Positive | Positive | Positive | Positive |
| T-F-07-132C-5 | DP-32138-1/T5 | Positive | Positive | Positive | Positive |
| T-F-07-132C-6 | DP-32138-1/T6 | Positive | Positive | Positive | Positive |
| T-F-07-132C-7 | DP-32138-1/T7 | Positive | Positive | Positive | Positive |
| T-F-07-132C-8 | DP-32138-1/T8 | Positive | Positive | Positive | Positive |
| T-F-07-132C-9 | DP-32138-1/T9 | Positive | Positive | Positive | Positive |
| T-F-07-132C-10 | DP-32138-1/T10 | Positive | Positive | Positive | Positive |

[1]A positive result indicates the amplification above a $C_T$ threshold of the DP-32138-1 target sequence in the plant. A negative result indicates no amplification above the $C_T$ threshold of the DP-32138-1 target sequence. A positive or negative determination indicates the maize endogenous reference in the plant was amplified.
[2]A positive result indicates the presence of the band for Ms45, zm-bt1-aa1, or DsRed2(Alt1) on the Southern blot, while a negative result indicates the absence of the appropriate band.

TABLE 3

Predicted and Observed Hybridizing Bands on Southern Blots; Bmt I Digest

| Probe | Figure | Predicted Fragment Size from PHP24597 T-DNA[1] (bp) | Predicted Fragment Size from Plasmid PHP24597[2] (bp) | Observed Fragment Size in DP-32138-1[3] (bp) |
|---|---|---|---|---|
| 5126 promoter | 5 | >8500 (border)[4] | 15455 | >8600<br>~7800*<br>~2700* |
| Ms45 | 5 | >8500 (border) | 15455 | >8600<br>~5200* |
| Pg47 promoter | 6 | >8500 (border) | 15455 | Obscured by endogenous bands<br>1 bands >8600*<br>2 bands 6100-8600*<br>2 bands 4900-6100*<br>2 bands 3600-4900* |

TABLE 3-continued

| | | | | |
|---|---|---|---|---|
| zm-bt1 | 6 | >8500 (border) | 15455 | >8600<br>~4200* |
| zm-aa1 | 7 | >8500 (border) | 15455 | >8600<br>3 bands >8600*<br>3 bands 6100-8600*<br>2 bands 4900-6100*<br>2 bands 3600-4900*<br>~3000*<br>~2700*<br>~2500*[5]<br>~1500* |
| ln2-1 terminator | 7 | >8500 (border) | 15455 | >8600<br>~8600*<br>~8000*<br>~4700*<br>~3200* |
| 35S enhancer | 8 | >8500 (border) | 15455 | >8600 |
| Ltp2 promoter | 8 | >8500 (border)<br>>1400 (border) | 15455<br>27657 | >8600<br>>8600 |
| DsRed2 | 9 | >1400 (border) | 27657 | >8600 |
| pinII terminator | 9 | >1400 (border) | 27657 | >8600 |

Note:

An asterisk (*) and gray shading indicates the designated band is due to hybridization to endogenous sequences, as can be determined by the presence of the same band in DP-32138-1 and control plants.

[1] Predicted size for probe hybridization to genomic DNA of DP-32138-1 maize containing a complete T-DNA insertion based on the map of the T-DNA from PHP24597 (FIG. 2). Border fragment sizes are rounded to the nearest 100 bp.

[2] Predicted size for probe hybridization to plasmid PHP24597 based on the plasmid map of PHP24597 (FIG. 1).

[3] Observed fragment sizes are approximated from the DIG-labeled DNA Molecular Weight Marker VII fragment on the Southern blots. Due to the inability to determine exact sizes on the blot, all approximated values are rounded to the nearest 100 bp.

[4] Border fragments are those in which one restriction site is in the inserted T-DNA and the other site is located in the flanking genomic DNA, providing a fragment of unique size for a given insertion.

[5] The ~2500 bp endogenous band is seen in only one of the DP-32138-1 plants and the Hi-II control plants.

TABLE 4

Predicted and Observed Hybridizing Bands on Southern Blots; Xho I Digest

| Probe | Figure | Predicted Fragment Size from PHP24597 T-DNA[1] (bp) | Predicted Fragment Size from Plasmid PHP24597[2] (bp) | Observed Fragment Size in DP-32138-1[3] (bp) |
|---|---|---|---|---|
| 5126 promoter | 10 | >2100 (border)[4] | 9471 | ~3600<br>>8600*<br>~3200* |
| Ms45 | 10 | >2100<br>3453 | 9471<br>3453 | ~3600<br>3453[5]<br>>8600*<br>~6500*<br>~600* |
| Pg47 promoter | 11 | 3453 | 3453 | 3453[6]<br>4 bands >8600*<br>3 bands 6100-8600*<br>~4100* |

TABLE 4-continued

| | | | | |
|---|---|---|---|---|
| zm-bt1 | 11 | 3453<br>>4400 (border) | 3453<br>29227 | 3453[5]<br>>8600<br>~8000*<br>~6700* |
| zm-aa1 | 12 | >4400 (border) | 29227 | Obscured by endogenous bands<br>3 bands >8600*<br>3 bands 6100-8600*<br>2 bands 4900-6100*<br>3 bands 3600-4900*<br>2 band 2800-3600*<br>5 bands 1950-2800*<br>4 bands 1200-1950*<br>~800* |
| ln2-1 terminator | 12 | >4400 (border) | 29227 | >8600<br>3 bands >8600*<br>2 bands 6100-8600*<br>~3800*<br>~3000* |
| 35S enhancer | 13 | >4400 (border) | 29227 | >8600 |
| Ltp2 promoter | 13 | >4400 (border | 29227 | >8600 |
| DsRed2 | 14 | >4400 (border) | 29227 | >8600 |
| pinII terminator | 14 | >4400 (border) | 29227 | >8600 |

Note:

An asterisk (*) and gray shading indicates the designated band is due to hybridization to endogenous sequences, as can be determined by the presence of the same band in DP-32138-1 and control plants.

[1]Predicted size for probe hybridization to genomic DNA of DP-32138-1 maize containing a complete T-DNA insertion based on the map of the T-DNA from PHP24597 (FIG. 2). Border fragment sizes are rounded to the nearest 100 bp.

[2]Predicted size for probe hybridization to plasmid PHP24597 based on the plasmid map of PHP24597 (FIG. 1).

[3]Observed fragment sizes are approximated from the DIG-labeled DNA Molecular Weight Marker VII fragments on the Southern blots. Due to the inability to determine exact sizes on the blot, all approximated values are rounded to the nearest 100 bp.

[4]Border fragments are those in which one restriction site is in the inserted T-DNA and the other site is located in the flanking genomic DNA, providing a fragment of unique size for a given insertion.

[5]Observed size is same as expected size due to equivalent migration to the plasmid band.

TABLE 5

Predicted and Observed Hybridizing Bands on Southern Blots; EcoR I Digest

| Probe | Figure | Predicted Fragment Size from PHP24597 T-DNA[1] (bp) | Predicted Fragment Size from Plasmid PHP24597[2] (bp) | Observed Fragment Size in DP-32138-1[3] (bp) |
|---|---|---|---|---|
| 5126 promoter | 15 | 7216 | 7216 | 7216[4]<br>2 bands >8600* |
| Ms45 | 15 | 7216 | 7216 | 7216[4]<br>>8600* |
| Pg47 promoter | 16 | 7216 | 7216 | 7216[4]<br>3 bands >8600*<br>~7400*<br>~5600* |
| zm-bt1 | 16 | 7216 | 7216 | 7216[4]<br>>8600*<br>~8600*<br>~3300* |

TABLE 5-continued

| | | | | |
|---|---|---|---|---|
| zm-aa1 | 17 | 7216 | 7216 | 7216[4] |
| | | | | 2 bands >8600* |
| | | | | 2 bands 4900-8600* |
| | | | | 4 bands 3600-4900* |
| | | | | ~4300*[5] |
| | | | | 2 bands 2800-3600* |
| | | | | 4 bands 1950-2800* |
| | | | | ~1700* |
| ln2-1 terminator | 17 | 7216 | 7216 | 7216[4] |
| | | | | 2 bands >8600* |
| | | | | ~8600* |
| | | | | ~7400* |
| | | | | ~3400* |
| 35S enhancer | 18 | 2462 | 2462 | 2462[4] |
| Ltp2 promoter | 18 | 2462 | 2462 | 2462[4] |
| DsRed2 | 19 | 2462 | 2462 | 2462[4] |
| pinII terminator | 19 | 2462 | 2462 | 2462[4] |

Note:

An asterisk (*) and gray shading indicates the designated band is due to hybridization to endogenous sequences, as can be determined by the presence of the same band in DP-32138-1 and control plants.

[1]Predicted size for probe hybridization to genomic DNA of DP-32138-1 maize containing a complete T-DNA insertion based on the map of the T-DNA from PHP24597 (FIG. 2). Border fragment sizes are rounded to the nearest 100 bp.

[2]Predicted size for probe hybridization to plasmid PHP24597 based on the plasmid map of PHP24597 (FIG. 1).

[3]Observed fragment sizes are approximated from the DIG-labeled DNA Molecular Weight Marker VII fragments on the Southern blots. Due to the inability to determine exact sizes on the blot, all approximated values are rounded to the nearest 100 bp.

[4]Observed size is same as expected size due to equivalent migration to the plasmid band.

[5]The ~4300 bp endogenous band is seen in only one of the DP-32138-1 plants and one of the Hi-II control plants.

TABLE 6

Predicted and Observed Hybridizing Bands on Southern Blots; Hind III Digest

| Probe | Figure | Predicted Fragment Size from PHP24597 T-DNA[1] (bp) | Predicted Fragment Size from Plasmid PHP24597[2] (bp) | Observed Fragment Size in DP-32138-1[3] (bp) |
|---|---|---|---|---|
| 5126 promoter | 20 | >9800 (border)[4] | 34658 | >8600[5] |
| | | | | ~5900* |
| | | | | ~4900* |
| Ms45 | 20 | >9800 (border)[4] | 34658 | >8600[5] |
| | | | | ~5400* |
| Pg47 promoter | 21 | >9800 (border)[4] | 34658 | Obscured by endogenous bands |
| | | | | 4 bands >8600* |
| | | | | 2 bands 6100-8600* |
| | | | | ~4800* |
| | | | | ~2100* |
| zm-bt1 | 21 | >9800 (border)[4] | 34658 | >8600[5] |
| | | | | ~8300* |

TABLE 6-continued

| | | | | |
|---|---|---|---|---|
| zm-aa1 | 22 | >9800 (border)[4] | 34658 | >8600[5] |
| | | | | >8600*[,6] |
| | | | | >8600* |
| | | | | 3 bands 6100-8600* |
| | | | | ~4200* |
| | | | | ~3800*[,6] |
| | | | | ~3100* |
| | | | | 4 bands 1950-2800* |
| | | | | 6 bands 1200-1950* |
| | | | | ~900* |
| ln2-1 terminator | 22 | >9800 (border)[4] | 34658 | >8600[5] |
| | | | | 2 bands >8600* |
| | | | | 2 bands 6100-8600* |
| | | | | ~2700* |
| 35S enhancer | 23 | >9800 (border)[4] | 34658 | >8600[5] |
| Ltp2 promoter | 23 | >9800 (border)[4] | 34658 | >8600[5] |
| DsRed2 | 24 | >9800 (border)[4] | 34658 | >8600[5] |
| pinII terminator | 24 | >9800 (border)[4] | 34658 | >8600[5] |

Note:

An asterisk (*) and gray shading indicates the designated band is due to hybridization to endogenous sequences, as can be determined by the presence of the same band in DP-32138-1 and control plants.

[1]Predicted size for probe hybridization to genomic DNA of DP-32138-1 maize containing a complete T-DNA insertion based on the map of the T-DNA from PHP24597 (FIG. 2). Border fragment sizes are rounded to the nearest 100 bp.

[2]Predicted size for probe hybridization to plasmid PHP24597 based on the plasmid map of PHP24597 (FIG. 1).

[3]Observed fragment sizes are approximated from the DIG-labeled DNA Molecular Weight Marker VII fragments on the Southern blots. Due to the inability to determine exact sizes on the blot, all approximated values are rounded to the nearest 100 bp.

[4]Border fragments are those in which one restriction site is in the inserted T-DNA and the other site is located in the flanking genomic DNA, providing a fragment of unique size for a given insertion.

[5]The expected size of this fragment is >9800 bp based on the PHP24597 T-DNA map (FIG. 2). However, as the largest molecular weight marker band on the blot is ~8600 bp, and the band runs above this marker, the observed size of the band is reported as >8600 bp.

[6]The >8600 bp and ~3800 bp endogenous bands are seen in only one of the DP-32138-1 plants and the Hi-II and Hi-II(ms45) control plants.

TABLE 7

Predicted and Observed Hybridizing Bands on Southern Blots; BamH I Digest

| Probe | Figure | Predicted Fragment Size from PHP24597 T-DNA[1] (bp) | Predicted Fragment Size from Plasmid PHP24597[2] (bp) | Observed Fragment Size in DP-32138-1[3] (bp) |
|---|---|---|---|---|
| 5126 promoter | 25 | >1500 (border)[4] | 8826 | ~3800 |
| | | | | 2 bands >8600* |
| | | | | ~7000* |
| Ms45 | 25 | >1500 (border) 2815 | 8826 2815 | ~3800 |
| | | | | 2815[5] |
| | | | | ~7000* |
| | | | | ~2700* |
| Pg47 promoter | 26 | 2502 | 2502 | 2502[5] |
| | | | | 3 bands >8600* |
| | | | | 3 bands 6100-8600* |
| | | | | 4 bands 4900-6100* |
| | | | | 2 bands 3600-4900* |
| zm-bt1 | 26 | 2502 | 2502 | 2502[5] |
| | | | | 4 bands >8600* |

TABLE 7-continued

| | | | | |
|---|---|---|---|---|
| zm-aa1 | 27 | 2502 2019 | 2502 2019 | 2502[5] 2019[5] 4 bands >8600* 3 bands 6100-8600* 2 bands 4900-6100* 5 bands 3600-4900* 2 bands 2800-3600* 4 bands 1950-2800* 4 bands 1200-1950* |
| ln2-1 terminator | 27 | 2019 | 2019 | 2019[5] 2 bands ~8600* |
| 35S enhancer | 28 | 2019 | 2019 | 2019[5] |
| Ltp2 promoter | 28 | 2019 | 2019 | 2019[5] |
| DsRed2 | 29 | >1200 (border) | 27225 | ~4600 ~6100 (faint) |
| pinII terminator | 29 | >1200 (border) | 27225 | ~4600 ~6100 (faint) |

Note:
An asterisk (*) and gray shading indicates the designated band is due to hybridization to endogenous sequences, as can be determined by the presence of the same band in DP-32138-1 and control plants.
[1]Predicted size for probe hybridization to genomic DNA of DP-32138-1 maize containing a complete T-DNA insertion based on the map of the T-DNA from PHP24597 (FIG. 2). Border fragment sizes are rounded to the nearest 100 bp.
[2]Predicted size for probe hybridization to plasmid PHP24597 based on the plasmid map of PHP24597 (FIG. 1).
[3]Observed fragment sizes are approximated from the DIG-labeled DNA Molecular Weight Marker VII fragments on the Southern blots. Due to the inability to determine exact sizes on the blot, all approximated values are rounded to the nearest 100 bp.
[4]Border fragments are those in which one restriction site is in the inserted T-DNA and the other site is located in the flanking genomic DNA, providing a fragment of unique size for a given insertion.
[5]Observed size is same as expected size due to equivalent migration to the plasmid band.

TABLE 8

Predicted and Observed Hybridizing Bands on Southern Blots;
BamH I/Hind III Digest

| Probe | FIG. | Predicted Fragment Size from PHP24597 T-DNA[1] (bp) | Predicted Fragment Size from Plasmid PHP24597[2] (bp) | Observed Fragment Size in DP-32138-1[3] (bp) |
|---|---|---|---|---|
| DsRed2 | 30 | >1200 (border)[4] | 26045 | ~2600 |
| pinII terminator | 30 | >1200 (border) | 26045 | ~2600 |

[1]Predicted size for probe hybridization to genomic DNA of DP-32138-1 maize containing a complete T-DNA insertion based on the map of the T-DNA from PHP24597 (FIG. 2). Border fragment sizes are rounded to the nearest 100 bp.
[2]Predicted size for probe hybridization to plasmid PHP24597 based on the plasmid map of PHP24597 (FIG. 1).
[3]Observed fragment sizes are approximated from the DIG-labeled DNA Molecular Weight Marker VII fragments on the Southern blots. Due to the inability to determine exact sizes on the blot, all approximated values are rounded to the nearest 100 bp.
[4]Border fragments are those in which one restriction site is in the inserted T-DNA and the other site is located in the flanking genomic DNA, providing a fragment of unique size for a given insertion.

TABLE 9

Predicted and Observed Hybridizing Bands on Southern Blots; Bgl II Digest

| Probe | Figure | Predicted Fragment Size from PHP24597 T-DNA[1] (bp) | Predicted Fragment Size from Plasmid PHP24597[2] (bp) | Observed Fragment Size in DP-32138-1[3] (bp) |
|---|---|---|---|---|
| 5126 promoter | 31 | >1700 (border)[4] | 4937 | ~3600<br>2 bands >8600* |
| Ms45 | 31 | >1700 (border)<br>806<br>4511 | 4937<br>806<br>4511 | ~3600<br>806[5, 6]<br>4511[5]<br>~7400*<br>~5000*<br>~800* |
| Pg47 promoter | 32 | 4511 | 4511 | 4511[5]<br>2 bands >8600*<br>2 bands 6100-8600*<br>2 bands 4900-6100*<br>~4600* |
| zm-bt1 | 32 | 4511 | 4511 | 4511[5]<br>~8600*<br>~8000* |
| zm-aa1 | 33 | 4511 | 4511 | 45115<br>overlapping bands >8000* (not resolved separately)<br>2 bands 6100-8000*<br>2 bands 4900-6100*<br>~4500*<br>~3000*<br>~2900*[7] |
| ln2-1 terminator | 33 | >2900 (border) | 31228 | ~4900<br>>8600*<br>2 bands 6100-8600*<br>~5900*<br>~3000* |
| 35S enhancer | 34 | >2900 (border) | 31228 | ~4900<br>~7400 (faint) |
| Ltp2 promoter | 34 | >2900 (border) | 31228 | ~4900<br>~7400 (faint) |
| DsRed2 | 35 | >2900 (border) | 31228 | ~4900<br>~7400 (faint) |
| pinII terminator | 35 | >2900 (border) | 31228 | ~4900<br>~7400 (faint) |

Note:

An asterisk (*) and gray shading indicates the designated band is due to hybridization to endogenous sequences, as can be determined by the presence of the same band in DP-32138-1 and control plants.

[1] Predicted size for probe hybridization to genomic DNA of DP-32138-1 maize containing a complete T-DNA insertion based on the map of the T-DNA from PHP24597 (FIG. 2). Border fragment sizes are rounded to the nearest 100 bp.

[2] Predicted size for probe hybridization to plasmid PHP24597 based on the plasmid map of PHP24597 (FIG. 1).

[3] Observed fragment sizes are approximated from the DIG-labeled DNA Molecular Weight Marker VII fragments on the Southern blots. Due to the inability to determine exact sizes on the blot, all approximated values are rounded to the nearest 100 bp.

[4] Border fragments are those in which one restriction site is in the inserted T-DNA and the other site is located in the flanking genomic DNA, providing a fragment of unique size for a given insertion.

[5] Observed size is same as expected size due to equivalent migration to the plasmid band.

[6] Band overlaps an endogenous band but can be detected by increased hybridization intensity.

[7] The ~2900 bp endogenous band is seen in only one of the DP-32138-1 plants and the 705 control plant.

TABLE 10

Predicted and Observed Hybridizing Bands on Southern Blots; Bgl II/Hind III Digest

| Probe | Predicted Fragment Size from PHP24597 T-DNA[1] (bp) | Predicted Fragment Size from Plasmid PHP24597[2] (bp) | Observed Fragment Size in DP-32138-1[3] (bp) |
|---|---|---|---|
| 35S enhancer | >2900 (border)[4] | 27807 | ~4100 |
| Ltp2 promoter | >2900 (border) | 27807 | ~4100 |
| DsRed2 | >2900 (border) | 27807 | ~4100 |
| pinII terminator | >2900 (border) | 27807 | ~4100 |

[1]Predicted size for probe hybridization to genomic DNA of DP-32138-1 maize containing a complete T-DNA insertion based on the map of the T-DNA from PHP24597 (FIG. 2). Border fragment sizes are rounded to the nearest 100 bp.
[2]Predicted size for probe hybridization to plasmid PHP24597 based on the plasmid map of PHP24597 (FIG. 1).
[3]Observed fragment sizes are approximated from the DIG-labeled DNA Molecular Weight Marker VII fragments on the Southern blots. Due to the inability to determine exact sizes on the blot, all approximated values are rounded to the nearest 100 bp.
[4]Border fragments are those in which one restriction site is in the inserted T-DNA and the other site is located in the flanking genomic DNA, providing a fragment of unique size for a given insertion.

TABLE 11

Description of Genetic Elements in Plasmid PHP24597

| Region | Location on plasmid (base pair position) | Known Genetic Element | Size (base pairs) | Description |
|---|---|---|---|---|
| T-DNA | 1 to 9950 | | 9950 | see Table 12 for information on the elements in this region |
| Plasmid Construct | 9951 to 34822 | includes elements below | 24872 | DNA from various sources for plasmid construction and plasmid replication |
| | 11126 to 11914 | spc | 789 | Spectinomycin resistance gene from bacteria (Fling et al., 1985) |
| | 13037 to 13406 | colE1 ori | 370 | Bacterial origin of replication region (*E. coli*) (Tomizawa et al., 1977) |
| | 14503 to 14515 | cos | 13 | cos site; cohesive ends from lambda bacteriophage DNA (Komari et al., 1996) |
| | 16221 to 16871 | tetR | 651 | Tetracycline resistance regulation gene from bacteria (Komari et al., 1996) |
| | 16977 to 18176 | tetA | 1200 | Tetracycline resistance gene from bacteria (Komari et al., 1996) |
| | 18807 to 20996 | rep | 2190 | rep operon from bacteria (includes trfA below) (Komari et al., 1996) |
| | 19449 to 20597 | trfA | 1149 | Trans-acting replication gene from bacteria (Komari et al., 1996) |
| | 24411 to 24522 | oriT | 112 | oriT origin of transfer region from bacteria (Komari et al., 1996) |
| | 26362 to 32632 | ctl | 6271 | Central control operon region from bacteria (Komari et al., 1996) |
| | 33640 to 34350 | oriV | 711 | oriV origin of replication region from bacteria (Komari et al., 1996) |
| Ti Plasmid Backbone | 34823 to 49637 | includes elements below | 14815 | Virulence (vir) gene region and intergenic regions from Ti plasmid of *Agrobacterium tumefaciens*. (Komari et al., 1996) |
| | 35847 to 36541 | virC1 | 695 | Virulence gene important for T-DNA insertion into genome |
| | 36544 to 37152 | virC2 | 609 | Virulence gene important for T-DNA insertion into genome |
| | 37263 to 38066 | virG | 804 | Virulence gene important for T-DNA insertion into genome |
| | 38198 to 47633 | virB | 9436 | Virulence gene important for T-DNA insertion into genome |
| | 49934 to 50303 | colE1 ori | 370 | Bacterial origin of replication region (*E. coli*) (Tomizawa et al., 1977) |
| | 51400 to 51412 | cos | 13 | cos site; cohesive ends from lambda bacteriophage DNA (Komari et al., 1996) |

TABLE 12

Description of Genetic Elements in the T-DNA Region of Plasmid PHP24597

| Location on T-DNA (base pair position) | Genetic Element | Size (base pairs) | Description |
|---|---|---|---|
| 1 to 25 | Right Border | 25 | T-DNA Right Border region from Ti plasmid of *Agrobacterium tumefaciens* |
| 26 to 177 | Ti Plasmid Region | 152 | Non-functional sequence from Ti plasmid of *A. tumefaciens* |
| 178 to 203 | Polylinker Region | 26 | Region required for cloning genetic elements |
| 204 to 706 | 5126 Promoter | 503 | Maize anther-specific 5126 promoter (Cigan and Albertsen, 1997) |
| 707 to 2658 | Ms45 Genomic Region | 1952 | Maize genomic DNA including the Ms45 coding sequence and associated 3' untranslated region as indicated below: Exon 1 bp 708 to 1086; Intron 1 bp 1087 to 1215; Exon 2 bp 1216 to 1499; Intron 2 bp 1500 to 1596; Exon 3 bp 1597 to 1764; Intron 3 bp 1765 to 1850; Exon 4 bp 1851 to 2258; 3' UTR bp 2384 to 2658 (Albertsen et al., 1993; Albertsen et al., 1995) |
| 2659 to 2730 | Polylinker Region | 72 | Region required for cloning genetic elements |
| 2731 to 5466 | Pg47 Promoter | 2736 | Promoter from the maize pollen-specific polygalacturonase (Pg47) gene (Allen and Lonsdale, 1993) |
| 5467 to 5468 | Polylinker Region | 2 | Region required for cloning genetic elements |
| 5469 to 5693 | zm-bt1 Transit Peptide | 225 | Amyloplast-targeting transit peptide from the maize Brittle-1 gene (Sullivan et al., 1991) |
| 5694 to 6956 | zm-aa1 Gene | 1263 | Maize α-amylase gene |
| 6957 to 7033 | Polylinker Region | 77 | Region required for cloning genetic elements |
| 7034 to 7377 | ln2-1 Terminator | 344 | Terminator sequence from the maize ln2-1 gene (Hershey and Stoner, 1991) |
| 7378 to 7411 | Polylinker Region | 34 | Region required for cloning genetic elements |
| 7412 to 7849 | CaMV 35S Enhancer | 438 | Enhancer region from the Cauliflower Mosaic Virus genome (Franck et al., 1980; Odell et al., 1985). |
| 7850 to 7905 | Polylinker Region | 56 | Region required for cloning genetic elements |
| 7906 to 8761 | Ltp2 Promoter | 856 | Promoter from barley lipid transfer protein (Ltp2) gene (Kalla et al., 1994) |
| 8762 to 8809 | Polylinker Region | 48 | Region required for cloning genetic elements |
| 8810 to 9487 | DsRed2(Alt1) Gene | 678 | Modified DsRed2 gene (Clontechniques, 2001) with internal BstE II restriction site removed |
| 9488 to 9528 | Polylinker Region | 41 | Region required for cloning genetic elements |
| 9529 to 9839 | pinII Terminator | 311 | Terminator region from *Solanum tuberosum* proteinase inhibitor II gene (Keil et al., 1986; An et al., 1989). |
| 9840 to 9872 | Polylinker Region | 33 | Region required for cloning genetic elements |
| 9873 to 9925 | Ti Plasmid Region | 53 | Non-functional sequence from Ti plasmid of *A. tumefaciens* |
| 9926 to 9950 | Left Border | 25 | T-DNA Left Border region from Ti plasmid of *Agrobacterium tumefaciens* |

Example 2

Sequencing of T-DNA Region of PHP24597

SEQ ID NO: 20 provides the deduced amino acid sequence from translation of the spliced exons from the Ms45 gene from plasmid PHP24597. The full-length MS45 protein is 412 amino acids in length and weighs approximately 47 kDa.

SEQ ID NO: 21 provides the deduced amino acid sequence from translation of the zm-bt1 transit peptide+zm-aa1 region from plasmid PHP24597. The amino acids at positions 1-75 comprise the transit peptide. The complete translation product, including transit peptide is 495 amino acids in length and weighs approximately 54 kDa. The processed ZM-AA1 protein, with the transit peptide removed, is 420 amino acids in length and weighs approximately 46 kDa.

SEQ ID NO: 33 provides the deduced amino acid sequence from translation of the DsRed2(Alt1) gene from plasmid PHP24597. The DsRed2 protein is 225 amino acids in length and weighs approximately 26 kDa.

SEQ ID NO: 1 provides the sequence of the T-DNA insert plus genomic border regions in 32138 maize.

Example 3

Polymerase Chain Reaction (PCR) Analysis of
Maize Event DP-32138-1

Polymerase chain reaction (PCR) amplification of the unique junctions spanning the introduced genetic elements can distinguish 32138 maize plants from their non-genetically-modified counterparts and can be used to screen for the presence of the inserted T-DNA. The purpose of this study was to verify the effectiveness and reliability of a construct-specific PCR assay on genomic DNA from leaf tissue of 32138 maize, and to assess the sensitivity of this method.

Experimental Design

Genomic DNA from leaf tissue of the test substance (seed from 32138 maize: lot# T-F-07-132C) and the control substance (seed from a non-genetically modified maize with a genetic background representative of the event background: lot# C-F-07-131C) was isolated and subjected to qualitative PCR amplification using a construct-specific primer pair. The PCR products were separated on a 2% agarose gel to confirm the presence of the inserted construct in the genomic DNA isolated from the test substance and the absence of the inserted construct in the genomic DNA isolated from the control substance. A reference standard (Low DNA Mass Ladder; Invitrogen Corporation Catalog #10380-012) was used to determine the PCR product size. The reliability of the construct-specific PCR method was assessed by repeating the experiment three times. The sensitivity of the PCR amplification was evaluated by various dilutions of the genomic DNA from event DP-32138-1.

DNA Extraction

Test and control leaf samples (V5-V7 leaf stage) were harvested from plants grown at the DuPont Experimental Station (Wilmington, Del.) from seed obtained from Pioneer Hi-Bred International, a DuPont Company (Johnston, Iowa). Genomic DNA extraction from the test and control leaf tissues was performed using a standard urea extraction protocol.

Genomic DNA was quantified using the NanoDrop® 1000 Spectrophotometer using ND-1000 V3.6 Software (Thermo-Scientific, Wilmington, Del.). DNA samples were visualized on an agarose gel to confirm quantitation values and to determine the DNA quality.

Polymerase Chain Reaction

Genomic DNA isolated from leaf of 32138 maize and control samples was subjected to PCR amplification (AccuPrime Taq DNA Polymerase High Fidelity, Invitrogen Corporation Catalog #12346) utilizing the construct-specific primer pair 08-0-2544/08-0-2582 (SEQ ID NOS: 2 and 3; Table 17) which targets the maize 5126 Promoter and the Ms45 Genomic sequences and allows for the unique identification of 32138 maize. The expected size of PCR product using this primer pair is 233 bp. A second primer set, 02-O-197/02-O-198 (SEQ ID NOS: 4 and 5; Table 17) was used to amplify the endogenous maize invertase gene (GenBank accession number AF171874.1) as a positive control for PCR amplification. The expected size of PCR product using this primer pair is 225 bp. PCR reagents and reaction conditions are shown in Table 13. In this study, 50 ng of leaf genomic DNA was used in all PCR reactions.

TABLE 13

PCR Reagents and Reaction Conditions

| PCR Reagents | | PCR Reaction Conditions | | | |
|---|---|---|---|---|---|
| Reagent | Volume (μL) | Cycle Element | Temp (° C.) | Time (sec) | # Cycles |
| Template DNA (50 ng/μl) | 1 | Initial Denaturation | 94 | 120 | 1 |
| Primer 1 (10 μM) | 2 | Denaturation | 94 | 15 | 35 |
| Primer 2 (10 μM) | 2 | Annealing | 60 | 20 | |
| PCR Master Mix* | 5 | Elongation | 68 | 60 | |
| ddH₂O | 39.7 | Final Elongation | 68 | 420 | 1 |
| Polymerase** | 0.3 | Hold Cycle | 4 | Until analysis | |

PCR: POLYMERASE CHAIN REACTION
DDH₂O: DOUBLE-DISTILLED WATER
*10× AccuPrime PCR Buffer II
**AccuPrime Taq DNA Polymerase High Fidelity Construct-Specific PCR Analysis for 32138 Maize A PCR product of approximately 230 bp in size amplified by the construct-specific primer set 08-0-2544/08-0-2582 was observed in PCR reactions using plasmid PHP24597 (50 ng) as template and all 32138 maize DNA samples, but absent in all control maize samples and the no-template control. This experiment was repeated three times, and similar results were obtained. FIG. 7 represents results observed for DNA extracts from five 32138 maize plants and five control maize plants. These results correspond closely with the expected PCR product size (233 bp) for samples containing 32138 maize genomic DNA. A PCR product approximately 220 bp in size was observed for both 32138 maize and control maize samples following PCR reaction with the primer set 02-O-197/02-O-198 for detection of the endogenous maize invertase gene (FIG. 8). These results correspond closely with the expected PCR product size (225 bp) for genomic DNA samples containing the maize endogenous invertase gene. The endogenous target band was not observed in the no-template control.

Sensitivity of Construct-Specific PCR Analysis for 32138 Maize

In order to assess the sensitivity of the PCR amplification, various concentrations of a single DNA sample of 32138 maize plant were added to non-genetically modified control DNA, resulting in 32138 maize DNA amounts ranging from 50 ng to 500 fg (the total amount of genomic DNA in all PCR samples was 50 ng). Each dilution was subjected to PCR amplification as previously conducted. Based on this analysis, the limit of detection (LOD) was determined to be approximately 50 pg of 32138 maize DNA in 50 ng of total DNA, or 0.1% 32138 maize DNA (FIG. 9). This is sufficient sensitivity for many screening applications.

Example 3

Conclusions

Qualitative PCR analysis utilizing a construct-specific primer set for 32138 maize confirmed that the test plants contained the inserted T-DNA from PHP24597, as evidenced by the presence of the construct-specific target band in all test plant samples analyzed, and the absence in the non-genetically modified control plants. This result was reproducible. Test and control plants both contained the endogenous maize invertase gene. The predicted sensitivity of the analysis under the conditions described is 0.1% 32138 maize DNA.

Example 4

Sequencing of the Inserted DNA and Flanking Regions of Event 32138

Southern blot analyses indicated that a single intact T-DNA from plasmid PHP24597 was inserted into the maize genome to produce 32138 maize; see, Example 1. This example provides the sequence of the inserted T-DNA in 32138 maize and further confirms that a single intact T-DNA was inserted in maize genome with a partial T-DNA insertion of 23 bp or 27 bp at 5' genomic border region. In addition, this example describes cloning and sequencing of the genomic border regions undertaken to obtain DNA sequence that could be used to uniquely identify 32138 maize.

The sequence of the insert and genomic border regions was determined to confirm the integrity of the inserted DNA and to characterize the genomic sequence flanking the insertion site present in 32138 maize. In total, 13998 bp of 32138 maize genomic sequence was confirmed, comprising 2114 bp of the 5' genomic border sequence, 2002 bp of the 3' genomic border sequence, and 9882 bp of inserted T-DNA from PHP24597. The inserted T-DNA in 32138 maize was found to have a 45 bp deletion on the Right Border (RB) end and a 23 bp deletion on the Left Border (LB) end. Also, a partial T-DNA insertion of 23 bp is located at positions 2092-2114 of the indicated genomic 5' border sequence. The sequence surrounding this partial insertion comprises additional junction sequences unique to 32138 maize and which may be used to specifically identify the 32138 event. All remaining transgenic sequence indicated at positions 2115 through 11,996 is intact and identical to the T-DNA of plasmid PHP24597.

The 5' and 3' genomic border regions of 32138 maize were verified to be of maize origin by PCR amplification and sequencing of the genomic border regions from both 32138 maize and control plants. Overall, characterization of the insert and genomic border sequence in 32138 maize confirms that a single intact insertion of the T-DNA from plasmid PHP24597 is present in the maize genome with a partial T-DNA insertion of 23 bp or 27 bp at 5' genomic border region.

Test Substance

The test substance is defined as maize seed containing event DP-32138-1 obtained from a T1 S1 generation of 32138 maize. Only red kernels were selected for use in the study. Further details regarding the source of the seed are provided in Example 1.

All seeds were obtained from Pioneer Hi-Bred International, Inc. (Pioneer, Johnston, Iowa) and pedigree information is on file with staff breeders. The log number is T-F-07-132C.

Control Substance

The control substance is defined as seed from a maize line that does not contain 32138 maize. The unmodified maize line has a genetic background representative of the event background; however, it does not contain the Ms45, zm-aa1 and DsRed2 (Alt1) gene cassettes. The log number is C-F-07-131C. Further details are provided in Example 1.

The Low DNA Mass Ladder (Invitrogen Corp., Carlsbad, Calif.), High DNA Mass Ladder (Invitrogen Corp.), and the GeneRuler 1 kb DNA Ladder (Fermentas, Glen Burnie, Md.) were used for gel electrophoresis to estimate DNA fragment sizes on agarose gels.

Plant Growth and Sample Collection

The 32138 maize seed and the control seed were planted in the Regulatory Science growth chambers at the DuPont Experimental Station (Wilmington, Del.) to produce plant tissues used for this study. One seed was planted per pot, and the pot was uniquely identified. All plants were grown with light, temperature, and water regulated for healthy plant growth.

Leaf samples were collected from each of the control and 32138 maize plants. For each sample, sufficient leaf material from above the growing point was collected and placed in a pre-labeled sample bag. The samples were placed on dry ice and were transferred to an ultra low freezer (<−55° C.) following collection. All samples were maintained frozen until processing. All leaf samples were uniquely labeled with the plant identifier and the date of harvest.

Genotype Confirmation Via Event-Specific PCR Analysis

A leaf sample was taken from all test and control plants for event-specific PCR analysis. DNA was extracted from each leaf sample using the Extract-N-Amp™ Plant PCR kit using the described procedure (Sigma-Aldrich, St. Louis, Mo.).

Real-time PCR was performed on each DNA sample utilizing an ABI PRISM® 7500HT Sequence Detection System (Applied Biosystems, Inc., Foster City, Calif.). Taq Man® probe and primer sets were designed to detect a target sequence from the 32138 maize. In addition, a second TaqMan® probe and primer set for a reference maize endogenous gene was used to confirm the presence of amplifiable DNA in each reaction. The analysis consisted of real-time PCR determination of qualitative positive/negative calls. The extracted DNA was assayed using optimized and validated primer and probe concentrations in TaqMan® Universal PCR Master Mix, No AmpErase® UNG (Applied Biosystems, Inc.). Initial incubation was at 95° C. for 10 minutes followed by 40 cycles as follows: 95° C. for 15 seconds, 60° C. for 1 minute.

Positive or negative determination for 32138 maize was based on comparison of the $C_T$ (threshold cycle) of the event-specific target PCR to that of the maize endogenous reference target. If the event and endogenous PCR targets amplified above $C_T$ threshold, then the plant was scored as positive for that event. If the endogenous target amplified and the event target did not, then the plant was scored as negative. If neither target amplified for a particular sample, then it was determined to be a poor quality sample or failed run and the assay was repeated.

DNA Extraction and Quantitation

Frozen leaf samples (1-2 gram quantities) were ground, and the genomic DNA was isolated using a standard Urea Extraction Buffer procedure. Following extraction, the DNA was visualized on an agarose gel to determine the DNA quality, and was quantified using the NanoDrop 1000 Spectrophotometer and ND-1000 V3.6 Software (ThermoScientific, Wilmington, Del.).

Polymerase Chain Reaction (PCR)

PCR primers were synthesized by IDT (Coralville, Iowa) and used at a concentration of 0.2-0.4 μM with 30-250 ng genomic DNA as template in a PCR reaction. DNA isolated from five 32138 maize plants was used as template DNA. PCR products were cloned and sequenced from four of the five 32138 maize plants. The following regions were PCR amplified from genomic DNA isolated from 32138 maize: the PHP24597 T-DNA insert, the 5' and 3' insert/genomic border junctions, and the 5' and 3' genomic border regions. PCR systems used were: AccuPrime Taq DNA Polymerase High Fidelity (Invitrogen Corp.), High Fidelity PCR system (Roche, Mannheim, Germany), Expand Long Template PCR System (Roche) and the Advantage®-GC2 genomic PCR mix (Clontech, Palo Alto, Calif.). The PCR products were visualized under UV light following electrophoresis through 1-2.5% agarose gel with 1×TBE (or 1×TAE) stained with ethidium bromide, or by 1.2% agarose E-Gel with SYBER®

Green (Invitrogen Corp.) under a blue light. Products were excised and purified from the gel using the QIAquick gel extraction kit (Qiagen, Valencia, Calif.).

Cloning of PCR Products

PCR products were cloned using the TOPO TA Cloning® Kit (pCR2.1-TOPO vector, Invitrogen) or pGem T-Easy Vector System (Promega). Plasmids were isolated using QIAprep Spin Miniprep Kit (Qiagen), screened by restriction enzyme digests, and sequenced.

DNA Sequencing

DNA fragments were cloned and submitted for sequencing at the Pioneer Crop Genetics Research sequencing facility (Wilmington, Del.). Sequencher™ software from Gene Codes Corporation (Ann Arbor, Mich.) was used to assemble the sequences. Sequence annotation was performed using Vector NTI 9.1.0 (Invitrogen Corp) by comparing the T-DNA insert sequences generated from 32138 maize with the sequences from the T-DNA region of plasmid PHP24597 (plasmid used for transformation to produce 32138 maize).

Sequencing of the T-DNA from Plasmid PHP24597

The T-DNA region of plasmid PHP24597, used for creating 32138 maize, was sequenced and compared with the inserted sequence generated from 32138 maize.

Sequencing of the Inserted T-DNA in 32138 Maize

For verification of the DNA sequence of the inserted T-DNA from plasmid PHP24597 in 32138 maize, primers were designed based on the sequence information from the T-DNA of plasmid PHP24597. Five overlapping PCR products were generated using genomic DNA from at least four different 32138 maize plants as template in the PCR. These PCR products were cloned and sequenced from 32138 maize plants.

Sequencing of 5' and 3' Flanking Genomic Border Regions

Initial sequence characterization of the 5' and 3' flanking border region were carried out using several rounds of inverse PCR (Silver and Keerikatte, (1989); Ochman, et al., (1988); Triglia, et al., (1988)), with primers anchored within various regions of the 5' and 3' ends of the inserted T-DNA. Sequence information obtained from inverse PCR was subjected to BLASTn analysis and showed identity to maize genomic DNA sequence (GenBank accession number AC196124) from the NCBI (National Center for Biotechnology Information) GenBank nucleotide dataset. This sequence was then used to design primers that spanned the 5' and 3' insert/genomic junctions of 32138 maize. The PCR products generated from genomic DNA isolated from four 32138 maize plants were cloned and sequenced to verify the 5' and 3' insert/genomic junctions and the genomic border regions. In order to demonstrate that the identified 5' and 3' genomic border sequences were of maize origin, PCR was performed within this 5' and 3' genomic regions on genomic DNA from 32138 maize and control plants. Cloned PCR products from four 32138 maize plants and two control plants were sequenced.

Genotype Confirmation Via Event-Specific PCR Analysis

All individual plants used for this study were tested for the presence of the 32138 insertion by an event-specific PCR analysis. All 32138 maize plants were positive for the insertion, whereas all the control plants were negative for the insertion. The results of the event-specific PCR assays for the 32138 plants and control plants are summarized in Table 13.

Sequence Characterization of Inserted DNA and Genomic Border Regions

The T-DNA sequence information of plasmid PHP24597 was used to design primers to verify the inserted sequence in 32138 maize (Tables 14 and 15). Preliminary sequences obtained by inverse PCR from 32138 maize genomic DNA were subjected to BLASTn analysis and showed identity to maize genomic DNA sequence (GenBank accession number AC196124) from NCBI (National Center for Biotechnology Information) GenBank nucleotide dataset. The sequence information from AC196124 was then used to design primers to extend additional genomic border regions (Tables 14 and 15).

To characterize the inserted T-DNA in 32138 maize, PCR primers were designed to amplify the T-DNA insert in five separate, overlapping PCR products: Fragment A (07-0-2286/07-0-2277; SEQ ID NOS: 6 and 7), Fragment B (08-0-2329/08-0-2398; SEQ ID NOS: 8 and 9), Fragment C (08-0-2402/07-0-2024; SEQ ID NOS: 10 and 11), Fragment D (08-0-2505/08-0-2504; SEQ ID NOS: 12 and 13), Fragment E (08-0-2408/08-0-2526; SEQ ID NOS: 14 and 15) (FIG. 10 and Tables 15 and 16). As expected, the predicted PCR products were generated only from 32138 maize genomic DNA samples, and were not present in the control samples. The five PCR products from 32138 maize plants were cloned and sequenced from four 32138 maize plants. When comparing the sequence of the inserted T-DNA in 32138 maize to the T-DNA region of plasmid PHP24597 used for creating 32138 maize, it was determined that there was a 45 bp deletion on the RB end, and a 23 bp deletion on the LB end. RB and LB termini deletions often occur in *Agrobacterium*-mediated transformation (Kim, et al., (2007) *Plant J.* 51:779-791). All remaining sequence is intact and identical to that of plasmid PHP24597. The sequence of the insertion is presented in SEQ ID NO: 1 and FIG. 11.

To verify the additional 5' genomic border sequence, PCR was performed with a forward primer (07-0-2286; SEQ ID NO: 6) in the 5' genomic border region and a reverse primer (07-0-2277; SEQ ID NO: 7) within the inserted T-DNA. The resulting 2198 bp PCR fragment A from 32138 maize genomic DNA samples was cloned and sequenced. The 2114 bp of 5' genomic border region sequence is presented as underlined sequence in FIG. 11.

To verify the additional 3' genomic border sequence, PCR was performed with a forward primer (08-0-2408; SEQ ID NO: 14) within the inserted T-DNA and a reverse primer (08-0-2526; SEQ ID NO: 15) in the 3' genomic border region. The resulting 2683 bp PCR fragment E from 32138 maize genomic DNA samples was cloned and sequenced. The 2002 bp of 3' genomic border region sequence is presented as underlined sequence in FIG. 11.

In total, 13998 bp of sequence from genomic DNA of 32138 maize were confirmed: 2114 bp of the 5' genomic border sequence, 2002 bp of the 3' genomic border sequence, and 9882 bp comprising the inserted T-DNA (FIGS. 10 and 11).

To demonstrate that the identified 5' and 3' flanking border sequences are of maize origin, PCR was performed within the 5' and 3' genomic border regions (primer pairs 08-0-2528/08-0-2538, SEQ ID NOS: 16 and 17; and 08-0-2539/08-0-2530, SEQ ID NOS: 18 and 19, respectively) on 32138 maize genomic DNA samples and control DNA samples. The expected PCR fragment F (294 bp for 5' genomic region) and PCR fragment G (297 bp for 3' genomic region) were generated from both 32138 maize and control samples. These PCR products were cloned and sequenced, and the corresponding products from the 32138 maize and the control maize were identical, indicating that the sequences were of maize genomic origin (FIGS. 12A and 12B).

TABLE 14

Summary of Genotype Confirmation via Event-Specific PCR Analysis of 32138 Maize and Control Maize Plants

|  | Plant ID abbreviation | Event-specific PCR[1] |
|---|---|---|
| Maize Plant ID |  |  |
| T-F-07-132C-1 | T1 | + |
| T-F-07-132C-2 | T2 | + |
| T-F-132C-3 | T3 | + |
| T-F-132C-4 | T4 | + |
| T-F-132C-5 | T5 | + |
| Control Maize Plant ID |  |  |
| C-F-07-131C-1 | C1 | − |
| C-F-07-131C-2 | C2 | − |

[1] Summary of event-specific real time PCR assay for 32138 maize. Positive (+) indicates the presence of 32138 maize event. Negative (−) indicates the absence of 32138 maize event.

TABLE 15

PCR Primers Used to Characterize the Genomic Border Regions and Inserted T-DNA in 32138 Maize

| PCR Fragment | Primer Pair | Size in bp | Amplified Region |
|---|---|---|---|
| A | 07-0-2286/07-0-2277 | 2198 | 5' Genomic border region and insert |
| B | 08-0-2329/08-0-2398 | 3052 | 5' Genomic border region and Insert |
| C | 08-0-2402/07-0-2024 | 3550 | Insert |
| D | 08-0-2505/08-0-2504 | 4073 | Insert |
| E | 08-0-2408/08-0-2526 | 2683 | 3' Genomic border region and insert |
| F | 08-0-2528/08-0-2538 | 294 | 5' Genomic border region |
| G | 08-0-2539/08-0-2530 | 297 | 3' Genomic border region |

FIG. 10 indicates the PCR fragments generated from 32138 maize genomic DNA that were cloned and sequenced: Fragment A (07-0-2286/07-0-2277), Fragment B (08-0-2329/08-0-2398), Fragment C (08-0-2402/07-0-2024), Fragment D (08-0-2505/08-0-2504), and Fragment E (08-0-2408/08-0-2526). The vertical dashed line represents the genomic border/insert junction. Fragment F (08-0-2528/08-0-2538) and G (08-0-2539/08-0-2530) represent the 5' and 3' genomic border regions, respectively (red arrows). FIG. 10 is not drawn to scale.

In FIG. 12A, primer pair 08-0-2528/08-0-2538 amplifies a PCR product (294 bp) from within the 5' flanking genomic DNA. In FIG. 12B, primer pair 08-0-2539/08-0-2530 amplifies a PCR product (297 bp) from within the 3' genomic border region.

Example 4

Conclusions

The sequence of the insert and genomic border regions was determined to confirm the integrity of the inserted DNA and to characterize the genomic sequence flanking the insertion site present in 32138 maize. In total, 13998 bp of 32138 maize genomic sequence was confirmed, comprising 2114 bp of the 5' genomic border sequence, 2002 bp of the 3' genomic border sequence, and 9882 bp of inserted T-DNA from PHP24597. The inserted T-DNA in 32138 maize was found to have a 45 bp deletion on the Right Border (RB) end and a 23 bp deletion on the Left Border (LB) end. Also, a partial T-DNA insertion of 23 bp is located at positions 2092-2114 of the indicated genomic 5' border sequence. The sequence surrounding this partial insertion comprises additional junction sequences unique to 32138 maize and which may be used to specifically identify the 32138 event. All remaining transgenic sequence indicated at positions 2115 through 11,996 is intact and identical to the T-DNA of plasmid PHP24597.

The 5' and 3' genomic border regions of 32138 maize were verified to be of maize origin by PCR amplification and sequencing of the genomic border regions from both 32138 maize and control plants. Overall, characterization of the insert and genomic border sequence in 32138 maize confirms that a single intact insertion of the T-DNA from plasmid PHP24597 is present in the maize genome with a partial T-DNA insertion of 23 bp or 27 bp at 5' genomic border region.

TABLE 16

SEQUENCE AND LOCATION OF PRIMERS USED FOR PCR REACTIONS.

| PCR Fragment | SEQ ID NO: | Primer Name | Sequence (5'-3') | Target Sequence Location (bp to bp)[1] |
|---|---|---|---|---|
| A | 6 | 07-0-2286 | CGAGACTTCACTGCCAGTTGATCG | 1-24 |
|  | 7 | 07-0-2277 | ACGGCTTGTCCCGCGTCATC | 2198-2179 |
| B | 8 | 08-0-2329 | GGTGCAGCTGACAATTACCACCGATCTTGGTG | 1766-1797 |
|  | 9 | 08-0-2398 | CAGACAGTGTCCGGTGCAGATCC | 4817-4795 |
| C | 10 | 08-0-2402 | TCCGCGACCGCGAATTGGGC | 4634-4653 |
|  | 11 | 07-0-2024 | TCCCGTCCGAGTACTGCGTGTC | 8183-8162 |
| D | 12 | 08-0-2505 | AGCATCGATCACGACACCATGGCG | 7520-7543 |
|  | 13 | 08-0-2504 | CATGTGGTACCTACGCGTTCGAATATCCA | 11592-11564 |
| E | 14 | 08-0-2408 | CACCGAGCGCCTGTACCCCCG | 11316-11336 |
|  | 15 | 08-0-2526 | TTATGCGCATGCAGCAGGAAACAGATACACC | 13998-13968 |
| F | 16 | 08-0-2528 | TTCTTGATGGAGAGATCGCAGCTCTGTTC | 1815-1843 |
|  | 17 | 08-0-2538 | CCGCTCATGATCAGATTTCACTGTGAGC | 2108-2081 |
| G | 18 | 08-0-2539 | GGAGATCCTGGTACACTATCTGTAGCAGTTTGG | 12000-12032 |
|  | 19 | 08-0-2530 | GGTCATTTCTCTAGAGTTTGATATACTTTATCATAG | 12296-12261 |

[1] Location in sequence of 32138 Maize (see SEQ ID NO: 1). Bases 1-2114 = 5' genomic border region, bases 2115-11996 = insert, bases 11997-13998 = 3' genomic border region.

TABLE 17

List of Primer Sequences Used in PCR Reactions

| SEQ ID NO: | Primer Name | Sequence 5'-3' | Target Sequence |
|---|---|---|---|
| 2 | 08-O-2544 | TCAAGCCGTGAGCAGACATGTTGCAG | 5126 Promoter |
| 3 | 08-O-2582 | CGAAGAAGAGGTGAGGGTACTGCACG | Ms45 Genomic |
| 4 | 02-O-197 | CCGCTGTATCACAAGGGCTGGTACC | Maize invertase gene |
| 5 | 02-O-198 | GGAGCCCGTGTAGAGCATGACGATC | Maize invertase gene |

The articles "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing inventions have been described in some detail by way of illustration and example for purposes of clarity of understanding, it will be obvious that certain changes and modifications may be practiced within the scope of the appended claims.

TABLE 18

Description of DNA Probes Used for Southern Hybridization

| Probe Name | Genetic Element | FIG. Probe | Position on PHP24597 T-DNA (bp to bp)[1] | Position on PHP24597 Plasmid (bp to bp)[2] | Length (bp) |
|---|---|---|---|---|---|
| 5126 promoter | 5126 promoter | FIG. 14 probe 1 | 304 to 706 | 304 to 706 | 403 |
| Ms45[3] | Ms45 Genomic region | FIG. 14 probe 2 | 707 to 1426 | 707 to 1426 | 720 |
|  |  |  | 1427 to 2258 | 1427 to 2258 | 832 |
|  |  |  | 2263 to 2658 | 2263 to 2658 | 396 |
| Pg47 promoter | Pg47 promoter (3' region) | FIG. 14 probe 3 | 5028 to 5451 | 5028 to 5451 | 424 |
| zm-bt1 | zm-bt1 transit peptide | FIG. 14 probe 4 | 5469 to 5693 | 5469 to 5693 | 225 |
| zm-aa1[4] | zm-aa1 gene | FIG. 14 probe 5 | 5701 to 6333 | 5701 to 6333 | 603 |
|  |  |  | 6334 to 6935 | 6334 to 6935 | 602 |
| In2-1 terminator | In2-1 terminator | FIG. 14 probe 6 | 7049 to 7377 | 7049 to 7377 | 329 |
| 35S enhancer | CaMV 35S enhancer region | FIG. 14 probe 7 | 7427 to 7846 | 7427 to 7846 | 420 |
| Ltp2 promoter | Ltp2 promoter | FIG. 14 probe 8 | 7906 to 8759 | 7906 to 8759 | 854 |
| DsRed2(Alt1) | DsRed2(Alt1) gene | FIG. 14 probe 9 | 8810 to 9487 | 8810 to 9487 | 678 |
| pinII terminator | pinII terminator | FIG. 14 probe 10 | 9582 to 9815 | 9582 to 9815 | 234 |
| RB | Plasmid backbone adjacent to T-DNA Right Border | FIG. 13 probe A | N/A[6] | 52436 to 52825 | 390 |
| LB | Plasmid backbone adjacent to T-DNA Left Border | FIG. 13 probe B | N/A[6] | 9975 to 10320 | 346 |
| spc | Spectinomycin resistance gene | FIG. 13 probe C | N/A[6] | 11130 to 11904 | 775 |
| virG | virG gene | FIG. 13 probe D | N/A[6] | 37294 to 38037 | 744 |
| tet[5] | Tetracycline resistance gene | FIG. 13 probe E | N/A[6] | 16983 to 17521 | 539 |
|  |  |  |  | 17627 to 18084 | 458 |

[1]The probe position is based on the PHP24597 T-DNA map (FIG. 14).
[2]The probe position is based on the PHP24597 plasmid map (FIG. 13).
[3]The Ms45 probe is comprised of three non-overlapping labeled fragments that are combined in the hybridization solution.
[4]The zm-aa1 probe is comprised of two non-overlapping labeled fragments that are combined in the hybridization solution.
[5]The tet probe is comprised of two labeled fragments that are combined in the respective hybridization solutions.
[6]Not Applicable as this element is not located in the PHP24597 T-DNA region.

REFERENCES

Albertsen, M. C., Beach, L. R., Howard, J. and Huffman, G. A.; 1995; "Nucleotide Sequences Mediating Male Fertility and Method of Using Same"; U.S. Pat. No. 5,478,369.

Albertsen, M. C., Fox, T. W. and Trimnell, M. R.; 1993; "Tagging, cloning, and characterizing a male fertility gene in maize"; *Am. J. Bot. Suppl.* 80:16.

Allen, R. L., and Lonsdale, D. M; 1993; "Molecular characterization of one of the maize polygalacturonase gene family members which are expressed during late pollen germination"; *Plant J.* 3(2):261-271.

An, G., Mitra, A., Choi, H. K., Costa, M. A., An, K., Thornburg, R. W. and Ryan, C. A.; 1989; "Functional Analysis of the 3' Control Region of the Potato Wound-Inducible Proteinase Inhibitor II Gene"; *Plant Cell* 1:115-122.

Brown, T. A.; 1998; "Restriction/Methylation"; *Molecular Biology LabFax I: Recombinant DNA*. San Diego, Calif., USA: Academic Press; 118-121.

Cigan, A. M., and Albertsen, M. C.; 1997; "Transgenic Plants and DNA Comprising Anther Specific Promoter 5126 and Gene to Achieve Male Sterility"; U.S. Pat. No. 5,689,051.

Cigan, A. M., Unger, E., Xu, R., Kendall, T., and Fox, T. W.; 2001; "Phenotypic complementation of ms45 maize requires tapetal expression of MS45"; *Sex. Plant Reprod.* 14:135-142.

Franck, A., Guilley, H., Jonard, G., Richards, K. and Hirth, L.; 1980; "Nucleotide sequence of cauliflower mosaic virus DNA"; *Cell* 21(1):285-294.

Fling, M. E., Kopf, J. and Richards, C.; 1985; "Nucleotide sequence of the transposon Tn7 gene encoding an aminoglycoside-modifying enzyme, 3'(9)-O-nucleotidyltransferase"; *Nucleic Acids Res.* 13:7095-7106.

Hershey, H. P. and Stoner, T. D.; 1991; "Isolation and characterization of cDNA clones for RNA species induced by substituted benzenesulfonamides in corn"; *Plant Mol. Biol.* 17(4):679-690.

Kalla, R., Shimamoto, K., Potter, R., Nielsen, P. S., Linnestad, C. and Olsen, O.-A.; 1994; "The promoter of the barley aleurone-specific gene encoding a putative 7 kDa lipid transfer protein confers aleurone cell-specific expression in transgenic rice"; *Plant J.* 6(6):849-860.

Keil, M., Sanches-Serrano, J., Schell, J. and Willmitzer, L.; 1986; "Primary structure of a proteinase inhibitor II gene from potato"; *Nucleic Acids Res.* 14:5641-5650.

Kim, S.-I., Veena and Gelvin, S. B.; 2007; "Genome-wide Analysis of *Agrobacterium* T-DNA Integration Sites in the Arabidopsis Genome Generated Under Non-selective Conditions"; *Plant J.* 51:779-791.

Komari, T., Hiei, Y., Saito, Y., Murai, N. and Kumashiro, T.; 1996; "Vectors carrying two separate T-DNAs for co-transformation of higher plants mediated by *Agrobacterium tumefaciens* and segregation of transformants free from selection markers"; *Plant J.* 10(1):165-174.

Living Colors™ DsRed2: Improved red fluorescent protein for use in living cells. 2001. *Clontechniques* July 2001:2-3.

Ochman, H., Gerber, A. S. and Hartl, D. L.; 1988; "Genetic Applications of an Inverse Polymerase Chain Reaction"; *Genetics* 120:621-623.

Odell, J. T., Nagy, F. and Chua, N.-H.; 1985; "Identification of DNA sequences required for activity of the cauliflower mosaic virus 35S promoter"; *Nature* 313:810-812.

Silver, J and Keerikatte, V.; 1989; "Novel Use of Polymerase Chain Reaction to Amplify Cellular DNA Adjacent to an Integrated Provirus"; *Journal of Virology* 63:1924.

Sullivan, T. D., Strelow, L. I., Illingworth, C. A., Phillips, R. L., and Nelson, Jr., O. E.; 1991; "Analysis of Maize Brittle-1 Alleles and a Defective *Suppressor-Mutator*-Induced Mutable Allele" *Plant Cell* 3:1337-1348.

Tomizawa, J-I., Ohmori, H., and Bird, R. E.; 1977; "Origin of replication of colicin E1 plasmid DNA"; *Proc. Natl. Acad. Sci.* 74(5):1865-1869.

Triglia, T., Peterson, M. G., and Kemp, D. J.; 1988; "A Procedure for in vitro Amplification of DNA Segments that Lie Outside the Boundaries of Known Sequences"; *Nucl. Acids Res.* 16:8186.

---

That which is claimed:

1. A maize plant comprising event E6611.32.1.38.

2. Maize seed produced by a plant of claim 1, wherein said seed comprises event E6611.32.1.38.

3. A transgenic maize plant, cell, tissue, seed, or DNA-containing part thereof comprising event E6611.32.1.38, wherein the event E6611.32.1.38 is present in a representative seed deposited with the American Type Culture Collection under accession number PTA-9158.

4. A maize plant, or DNA-containing part thereof, comprising DNA of nucleotides 2071 through 11,996 of SEQ ID NO: 1.

5. A maize plant, or DNA-containing part thereof, comprising DNA of nucleotides 2115 through 12,050 of SEQ ID NO: 1.

* * * * *